United States Patent
Zhang et al.

(10) Patent No.: US 11,542,336 B2
(45) Date of Patent: Jan. 3, 2023

(54) GCGR ANTIBODY AND GLP-1 FUSION PROTEIN THEREOF, PHARMACEUTICAL COMPOSITION THEREOF AND APPLICATION THEREOF

(71) Applicant: GMAX BIOPHARM LLC, Hangzhou (CN)

(72) Inventors: Cheng Zhang, Hangzhou (CN); Hua Zhang, Hangzhou (CN); Xiaofeng Wang, Hangzhou (CN); Chenjiang Yao, Hangzhou (CN); Yan Jiang, Hangzhou (CN); Liangliang Bi, Hangzhou (CN); Shuqian Jing, Hangzhou (CN)

(73) Assignee: GMAX BIOPHARM LLC, Hangzhou (CN)

(*) Notice: Subject to any disclaimer, the term of this patent is extended or adjusted under 35 U.S.C. 154(b) by 0 days.

(21) Appl. No.: 17/046,686

(22) PCT Filed: Mar. 19, 2019

(86) PCT No.: PCT/CN2019/078674
§ 371 (c)(1),
(2) Date: Oct. 9, 2020

(87) PCT Pub. No.: WO2019/196603
PCT Pub. Date: Oct. 17, 2019

(65) Prior Publication Data
US 2021/0122827 A1 Apr. 29, 2021

(30) Foreign Application Priority Data
Apr. 10, 2018 (CN) .......................... 201810316473.0

(51) Int. Cl.
*C07K 16/28* (2006.01)
*C07K 14/605* (2006.01)

(52) U.S. Cl.
CPC ........ *C07K 16/2869* (2013.01); *C07K 14/605* (2013.01); *C07K 2317/24* (2013.01); *C07K 2317/94* (2013.01); *C07K 2319/00* (2013.01)

(58) Field of Classification Search
CPC .............. C07K 16/2869; C07K 14/605; C07K 2317/24; C07K 2317/94
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,331,647 A | 5/1982 | Goldenberg |
| 4,496,689 A | 1/1985 | Mitra |
| 4,518,584 A | 5/1985 | Mark et al. |
| 4,640,835 A | 2/1987 | Shimizu et al. |
| 4,670,417 A | 6/1987 | Iwasaki et al. |
| 4,737,462 A | 4/1988 | Mark et al. |
| 4,751,180 A | 6/1988 | Cousens et al. |
| 4,791,192 A | 12/1988 | Nakagawa et al. |
| 4,935,233 A | 6/1990 | Bell et al. |
| 4,946,778 A | 8/1990 | Ladner et al. |
| 5,011,912 A | 4/1991 | Hopp et al. |
| 5,457,035 A | 10/1995 | Baum et al. |
| 6,133,426 A | 10/2000 | Gonzalez et al. |
| 6,210,924 B1 | 4/2001 | Hu et al. |
| 6,696,245 B2 | 2/2004 | Winter et al. |
| 6,703,199 B1 | 3/2004 | Koide |
| 6,846,634 B1 | 1/2005 | Tomlinson et al. |
| 10,668,167 B2* | 6/2020 | McPherson .......... C07J 71/0031 |
| 2003/0039958 A1 | 2/2003 | Holt et al. |
| 2004/0009507 A1 | 1/2004 | Winter et al. |
| 2004/0038291 A2 | 2/2004 | Tomlinson et al. |
| 2004/0202995 A1 | 10/2004 | de Wildt et al. |
| 2005/0202512 A1 | 9/2005 | Tomlinson et al. |
| 2005/0238646 A1 | 10/2005 | Ledbetter et al. |
| 2012/0128679 A1 | 5/2012 | Okamoto et al. |
| 2014/0335091 A1 | 11/2014 | Forgie et al. |

FOREIGN PATENT DOCUMENTS

| | | |
|---|---|---|
| CN | 103314011 A | 9/2013 |
| CN | 104231083 A | 12/2014 |
| CN | 104371019 A | 2/2015 |
| CN | 106084031 A | 11/2016 |
| WO | WO 1993010151 A1 | 5/1993 |
| WO | WO 1994010308 A1 | 10/1993 |
| WO | WO 2007124463 A1 | 11/2007 |
| WO | WO 2008036341 A2 | 3/2008 |
| WO | WO 2008036341 A3 | 3/2008 |
| WO | WO 2009120530 A1 | 10/2009 |
| WO | WO 2011030935 A1 | 3/2011 |

(Continued)

OTHER PUBLICATIONS

Ahren, 2015, "Glucagon—Early breakthroughs and recent discoveries" Peptides, 67:74-81.
Ashkenazi et al., 1991, "Protection against endotoxic shock by a tumor necrosis factor receptor immunoadhesin," Proc. Natl. Acad. Sci. USA, 88(23):10535-10539.
Baron et al., 1995, "Co-regulation of two gene activities by tetracycline via a bidirectional promoter," Nucleic Acids Res., 23(17):3605-3606.
Bauer et al., 1985, "A genetic enrichment for mutations constructed by oligodeoxynucleotide-directed mutagenesis," Gene, 37(1-3):73-81.
Baum et al., 1994, "Molecular characterization of murine and human OX40/OX40 ligand systems: identification of a human OX40 ligand as the HTLV-1-regulated protein gp34," EMBO J., 13(17):3992-4001.
Bird et al., 1988, "Single-chain antigen-binding proteins," Science, 242(4877):423-426.

(Continued)

*Primary Examiner* — Gyan Chandra
(74) *Attorney, Agent, or Firm* — Jones Day

(57) ABSTRACT

Provided herein are a glucagon receptor (GCGR) antibody and its fusion protein with glucagon-like peptide-1 (GLP-1), and a pharmaceutical composition thereof. Also provided herein is a method for using the GCGR antibody and its fusion protein with GLP-1 to treat, prevent or improve one or more symptoms of hyperglycemia, type 2 diabetes, metabolic syndrome or dyslipidemia.

7 Claims, 5 Drawing Sheets

Specification includes a Sequence Listing.

(56) References Cited

FOREIGN PATENT DOCUMENTS

| WO | WO 2012071372 A2 | 5/2012 |
|---|---|---|
| WO | WO 2012071372 A3 | 5/2012 |
| WO | WO 2013059531 A1 | 4/2013 |
| WO | WO 2016045400 A1 | 3/2016 |
| WO | WO 2016161154 A1 | 10/2016 |
| WO | WO 2018044903 A1 | 3/2018 |

OTHER PUBLICATIONS

Bowie et al., 1991, "A method to identify protein sequences that fold into a known three-dimensional structure," Science, 253(5016):164-170.
Brand et al., 1996, "Evidence for a major role for glucagon in regulation of plasma glucose in conscious, nondiabetic, and alloxan-induced diabetic rabbits," Diabetes, 45(8):1076-1083.
Brenner et al., 1997, "Population statistics of protein structures: lessons from structural classifications," Curr. Opin. Struct. Biol., 7(3):369-376.
Byrn et al., 1990, "Biological properties of a CD4 immunoadhesin," Nature, 344(6267):667-670.
Chou et al., 1974, "Conformational parameters for amino acids in helical, beta-sheet, and random coil regions calculated from proteins," Biochemistry, 13(2):211-222.
Chou et al., 1974, "Prediction of protein conformation," Biochemistry, 13(2):222-245.
Chou et al., 1978, "Empirical predictions of protein conformation," Annu. Rev. Biochem., 47:251-276.
Chou et al., 1978, "Prediction of the secondary structure of proteins from their amino acid sequence," Adv. Enzymol. Relat. Areas Mol. Biol., 47:45-148.
Chou et al., 1979, "Prediction of beta-turns," Biophys. J., 26(3):367-383.
Craik, 1985, "Use of Oligonucleotides for Site-Specific Mutagenesis," BioTechnique, 3:12-19.
Crameri et al., 1998, "DNA shuffling of a family of genes from diverse species accelerates directed evolution," Nature, 391(6664):288-291.
De Graaf et al., 2002, "Expression of scFvs and scFv fusion proteins in eukaryotic cells," Methods Mol. Biol., 178:379-387.
English translation of International Search Report and Written Opinion for International Patent Application No. PCT/CN2019/078674 (Pub No. WO 2019196603) dated May 15, 2019 (7 pages).
Fanslow et al., 1994, "Structural characteristics of CD40 ligand that determine biological function," Semin. Immunol., 6(5):267-278.
Gluzman, 1981, "SV40-transformed simian cells support the replication of early SV40 mutants," Cell, 23(1):175-182.
Gribskov et al., 1987, "Profile analysis: detection of distantly related proteins," Proc. Natl. Acad. Sci. USA, 84(13):4355-4358.
Gribskov et al., 1990, "Profile analysis," Methods Enzymol., 183:146-159.
Gu et al., 2009, "Long-term inhibition of the glucagon receptor with a monoclonal antibody in mice causes sustained improvement in glycemic control, with reversible alpha-cell hyperplasia and hyperglucagonemia," J Pharmacol. Exp. Ther., 331(3):871-881.
Harris, 1995, "Processing of C-terminal lysine and arginine residues of proteins isolated from mammalian cell culture," J. Chromatogr. A., 705(1):129-134.
Holliger et al., 1993, ""Diabodies": small bivalent and bispecific antibody fragments," Proc. Natl. Acad. Sci. USA, 90(14):6444-6448.
Holliger et al., 2005, "Engineered antibody fragments and the rise of single domains," Nat. Biotechnol., 23(9):1126-1136.
Holm et al., 1999, "Protein folds and families: sequence and structure alignments," Nucleic Acids Res., 27(1):244-247.
Hopp et al., 1988, "A Short Polypeptide Marker Sequence Useful for Recombinant Protein Identification and Purification," Bio/Technology, 6:1204-1210.
Hoppe et al., 1994, "A parallel three stranded alpha-helical bundle at the nucleation site of collagen triple-helix formation," FEBS Lett., 344(2-3):191-195.
Huston et al., 1988, "Protein engineering of antibody binding sites: recovery of specific activity in an anti-digoxin single-chain Fv analogue produced in *Escherichia coli*," Proc. Natl. Acad. Sci. USA, 85(16):5879-5883.
Jazayeri et al., 2016, "Extra-helical binding site of a glucagon receptor antagonist" Nature, 533(7602):274-277.
Jelinek et al., 1993, "Expression cloning and signaling properties of the rat glucagon receptor," Science, 259(5101):1614-1616.
Jones, 1997, "Progress in protein structure prediction," Curr. Opin. Struct. Biol., 7(3):377-387.
Korndorfer et al., 2003, "Crystallographic analysis of an "anticalin" with tailored specificity for fluorescein reveals high structural plasticity of the lipocalin loop region," Proteins, 53(1):121-129.
Kortt et al., 1997, "Single-chain Fv fragments of anti-neuraminidase antibody NC10 containing five- and ten-residue linkers form dimers and with zero-residue linker a trimer," Protein Eng., 10(4):423-433.
Kortt et al., 2001, "Dimeric and trimeric antibodies: high avidity scFvs for cancer targeting," Biomol. Eng., 18(3):95-108.
Kostic et al., 2018, "A first-in-human pharmacodynamic and pharmacokinetic study of a fully human anti-glucagon receptor monoclonal antibody in normal healthy volunteers," Diabetes Obes. Metab., 20(2):283-291 (Epub 2017).
Kriangkum et al., 2001, "Bispecific and bifunctional single chain recombinant antibodies," Biomol. Eng., 18(2):31-40.
Landschulz et al., 1988, "The leucine zipper: a hypothetical structure common to a new class of DNA binding proteins," Science, 240(4860):1759-1764.
Lee et al., 2016, "Glucagon is the key factor in the development of diabetes," Diabetologia, 59(7):1372-1375.
Li et al., 2018, "Glutazumab, a novel long-lasting GLP-1/anti-GLP-1R antibody fusion protein, exerts anti-diabetic effects through targeting dual receptor binding sites," Biochem. Pharmacol., 150:46-53.
Low et al., 1996, "Mimicking somatic hypermutation: affinity maturation of antibodies displayed on bacteriophage using a bacterial mutator strain," J. Mol. Biol., 260(3):359-368.
Lunde et al., 2002, "Troybodies and pepbodies," Biochem. Soc. Trans., 30(4):500-506.
Maniatis et al., 1987, "Regulation of inducible and tissue-specific gene expression," Science, 236(4806):1237-1245.
Mari et al., 2016, "Differential effects of once-weekly glucagon-like peptide-1 receptor agonist dulaglutide and metformin on pancreatic β-cell and insulin sensitivity during a standardized test meal in patients with type 2 diabetes," Diabetes Obes. Metab., 8(8):834-839.
Marks et al., 1992, "By-passing immunization: building high affinity human antibodies by chain shuffling," Biotechnology (NY), 10(7):779-783.
McMahan et al., 1991, "A novel IL-1 receptor, cloned from B cells by mammalian expression, is expressed in many cell types," EMBO J., 10(10):2821-2832.
Moult, 1996, "The current state of the art in protein structure prediction," Curr. Opin. Biotechnol., 7(4):422-427.
Nisonoff et al., 1960, "Separation of univalent fragments from the bivalent rabbit antibody molecule by reduction of disulfide bonds," Arch. Biochem. Biophys., 89:230-244.
Nygren et al., 1997, "Scaffolds for engineering novel binding sites in proteins," Curr. Opin. Struct. Biol., 7(4):463-469.
Patten et al., 1997, "Applications of DNA shuffling to pharmaceuticals and vaccines," Curr. Opin. Biotechnol., 8(6):724-733.
Pittner et al., 1991, "Activation of membrane protein kinase C by glucagon and Ca(2+)-mobilizing hormones in cultured rat hepatocytes. Role of phosphatidylinositol and phosphatidylcholine hydrolysis," Biochem. J., 277(Pt 2):371-378.
Poljak, 1994, "Production and structure of diabodies," Structure, 2(12):1121-1123.
Porter, 1959, "The hydrolysis of rabbit y-globulin and antibodies with crystalline papain," Biochem. J., 73(1):119-126.

(56) References Cited

OTHER PUBLICATIONS

Rasmussen et al., 1998, "Isolation, characterization and recombinant protein expression in Veggie-CHO: A serum-free CHO host cell line," Cytotechnology, 28(1-3):31-42.

Roque et al., 2004, "Antibodies and genetically engineered related molecules: production and purification," Biotechnol. Prog., 20(3):639-654.

Schier et al., 1996, "Isolation of picomolar affinity anti-c-erbB-2 single-chain Fv by molecular evolution of the complementarity determining regions in the center of the antibody binding site," J. Mol. Biol., 263(4):551-567.

Sippl et al., 1996, "Threading thrills and threats," Structure, 4(1):15-19.

Thompson et al., 1996, "Affinity maturation of a high-affinity human monoclonal antibody against the third hypervariable loop of human immunodeficiency virus: use of phage display to improve affinity and broaden strain reactivity," J. Mol. Biol., 16;256(1):77-88.

Thornton et al., 1991, "Protein structure. Prediction of progress at last," Nature, 354(6349):105-106.

Urlaub et al., 1980, "Isolation of Chinese hamster cell mutants deficient in dihydrofolate reductase activity," Proc. Natl. Acad. Sci. USA, 77(7):4216-4220.

Vaughan et al., 1998, "Human antibodies by design," Nat. Biotechnol., 16(6):535-539.

Voss et al., 1986, "The role of enhancers in the regulation of cell-type-specific transcriptional control," Trends in Biochemical Sciences, 11(7):287-289.

Wakelam et al., 1986, "Activation of two signal-transduction systems in hepatocytes by glucagon," Nature, 323(6083):68-71.

Walder et al., 1986, "Oligodeoxynucleotide-directed mutagenesis using the yeast transformation system," Gene, 42(2):133-139.

Ward et al., 1989, "Binding activities of a repertoire of single immunoglobulin variable domains secreted from *Escherichia coli*" Nature, 341(6242):544-546.

Yang et al., 1995, "CDR walking mutagenesis for the affinity maturation of a potent human anti-HIV-1 antibody into the picomolar range," J. Mol. Biol., 254(3):392-403.

Hai et al., 2009, "Fully Human Monoclonal Antibodies Antagonizing the Glucagon Receptor Improve Glucose Homeostatis in Mice and Monkeys," Journal of Pharmacology and Experimental Therapeutics, American Society for Pharmacology and Experimental Therapeutics, 329(1):102-111.

\* cited by examiner

GCGR ANTIBODY AND GLP-1 FUSION PROTEIN THEREOF, PHARMACEUTICAL COMPOSITION THEREOF AND APPLICATION THEREOF

CROSS-REFERENCE TO RELATED APPLICATIONS

This application is a U.S. national stage of International Patent Application No. PCT/CN2019/078674, filed Mar. 19, 2019, which claims the priority to Chinese Patent Application No. 201810316473.0, filed Apr. 10, 2018, the disclosure of each of which is incorporated by reference herein in its entirety.

SEQUENCE LISTING

This application incorporates by reference in its entirety the Computer Readable Form of a Substitute Sequence Listing in ASCII text format submitted via EFS-Web. The Sequence Listing text file submitted via EFS-Web is entitled "14254-009-999_Sequence_Listing.txt," was created on Oct. 8, 2020 and is 81,969 bytes in size.

FIELD

Provided herein are a glucagon receptor (GCGR) antibody and its fusion protein with glucagon-like peptide-1 (GLP-1), and a pharmaceutical composition thereof. Also provided herein is a method for using the GCGR antibody and its fusion protein with GLP-1 to treat, prevent or improve one or more symptoms of hyperglycemia, type 2 diabetes, metabolic syndrome or dyslipidemia.

BACKGROUND

Human glucagon is an important hormone, that works in coordination with insulin, in adjusting the glucose level in the circulation system of the human body. Glucagon and insulin are both peptide hormones. Glucagon is generated by the α-cells of pancreatic islets, while insulin is generated by β-cells of pancreatic islets. When blood sugar level decreases, glucagon mainly functions through stimulating some targets cells (mainly hepatocytes) to release glucose, counteracting insulin function in adjusting the blood glucose level. When blood glucose level rises, insulin stimulates cells to absorb and store glucose, in order to lower blood glucose level.

Natural human glucagon consists of 29 amino acid residues: His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr.

Glucagon, through interaction with its receptor, activates the downstream signaling pathway. Glucagon receptor ("GCGR" in short) belongs to the G protein-coupled receptor family and secretion receptor subfamily, after ligand-receptor interaction, through the activation of second messenger of adenylate cyclase, to exert its functions. This increases the level of cAMP in hepatocytes, and in turn initiates the gluconeogenesis reaction and glycogenolysis reaction, increasing the blood glucose level. (Wakelam et al., 1986, Nature 323:68-71; Pittner and Fain, 1991, Biochem J. 277:371-8).

Diabetes is a common glucose metabolic disorder, which manifests as hyperglycemia, subcategorized into type 1 diabetes (T1D) with absolute insufficiency in insulin and type 2 diabetes (T2D) with relative insufficiency of insulin. T1D patients show symptoms of hyperglycemia and hypo-insulinemia, and for this type of diabetes the usual countermeasure is to provide insulin. But, in some of the T1D and T2D cases, absolute or relative high level of glucagon results in hyperglycemia. In healthy or diabetic animal models, using selective or specific antibody to eliminate the glucagon in blood circulation can facilitate the decrease of blood glucose level (Brand et al., 1996, Diabetes 45:1076). These studies indicate that inhibiting glucagon or GCGR can be an auxiliary approach for treating the common hyperglycemia in diabetes cases.

Through antibodies that target GCGR, the interaction between glucagon and GCGR can be blocked, which may be used as an approach to control or reduce the blood sugar level and a novel method to treat diabetes (US 2008/036341 A2 and US 2012/0128679 A1). But in practice, animal experiments and clinical studies showed that direct blocking of the glucagon through a GCGR antibody induced notable negative feedback, and caused very high level of glucagon release into blood, transient rising of AST level and α-cell hyperplasia in pancreatic islets (Kostic et al., 2018, Diabetes Obes Metab. 20:283-91; Gu et al., 2009, JPET 331:871-881).

For the fusion protein of GCGR antibody with GLP-1 (GLP-1 fusion protein), in one aspect, the GCGR antibodies moiety, through preventing glucagon from interacting with its receptor, lowers the intracellular level of cAMP and the blood sugar; in another aspect, the GLP-1 moiety is also effective in lowering the blood sugar. In this way, the two parts of the GLP-1 fusion protein, the antibody of GCGR and the part of GLP-1, play the role of lowering blood sugar at the same time. The two have a synergistic effect, which can lower blood sugar more greatly, thereby improving the blood sugar lowering effect.

In addition, on the basis of the synergistic effect, the GCGR antibodies do not need to be at a very high clinical dosage, that is, at a lower dosage, coupled with GLP-1 agonist, the GCGR antibody is able to reduce the blood sugar level significantly. This can reduce blood sugar level to a larger extend than using GCGR antibody alone at high dosage, and thus circumvent the side effects associated with high dose of GCGR antibody, for example, the α-cell hyperplasia in pancreatic islets. Furthermore, GLP-1 agonist induces the release of insulin, which in turn inhibits the generation of more glucagon (Mari et. al., 2016, Diabetes Obes Metab. 18:834-9). The GLP-1 part of the GLP-1 fusion protein can inhibit the leveling up of glucagon concentration and counteract the increase of glucagon level as a result of negative feed of GCGR inhibition by antibody. Thus, the administration of GLP-1 fusion protein can significantly reduce the toxic side effect of the drug.

The sugar lowering effect of the GCGR antibody part of the GLP-1 fusion protein functions synergistically with the GLP-1 part, through their two distinctive mechanisms to treat hyperglycemia, T2D, metabolic syndrome and other syndrome including dyslipidemia. GLP-1 fusion protein lowers the blood sugar level more than using GLP-1 agonist alone, and also it has less toxic side effects than using GCGR antibody alone. GLP-1 fusion protein has a more significant blood sugar lowering effect and is safer as well.

SUMMARY

Provided herein is an antibody specifically binding to GCGR, comprising one, two, three, four, five or six amino acid sequences, where each amino acid sequence is independently selected from the amino acid sequences listed below:

a. Light chain CDR1 amino acid sequence: SEQ ID NO: 1, SEQ ID NO: 4, SEQ ID NO: 7, SEQ ID NO: 10, SEQ ID NO: 13, SEQ ID NO: 16, SEQ ID NO: 18, and SEQ ID NO: 20;

b. Light chain CDR2 amino acid sequence: SEQ ID NO: 2, SEQ ID NO: 5, SEQ ID NO: 8, SEQ ID NO: 11, and SEQ ID NO: 14;

c. Light chain CDR3 amino acid sequence: SEQ ID NO: 3, SEQ ID NO: 6, SEQ ID NO: 9, SEQ ID NO: 12, SEQ ID NO: 15, SEQ ID NO: 17, SEQ ID NO: 19, and SEQ ID NO: 21;

d. Heavy chain CDR1 amino acid sequence: SEQ ID NO: 22, SEQ ID NO: 25, and SEQ ID NO: 28, SEQ ID NO: 31, and SEQ ID NO: 34;

e. Heavy chain CDR2 amino acid sequence: SEQ ID NO: 23, SEQ ID NO: 26, SEQ ID NO: 29, SEQ ID NO: 32, and SEQ ID NO: 35; and f. Heavy chain CDR3 amino acid sequence: SEQ ID NO: 24, SEQ ID NO: 27, SEQ ID NO: 30, SEQ ID NO: 33, and SEQ ID NO: 36.

Provided herein is a GLP-1 fusion protein, comprising an antibody specifically binding to GCGR, and one, two, three, four, five, six, seven or eight GLP-1 fragments; the fusion protein connects the carboxy terminal of a GLP-1 fragment with the amino terminal of a light chain or a heavy chain of a GCGR antibody via a peptide linker.

Further provided herein is a GLP-1 fusion protein, comprising an antibody specifically binding to GCGR, and one, two, three, four, five, six, seven or eight reverse GLP-1 fragments; the fusion protein connects the carboxy terminal of a GLP-1 fragment with the amino terminal of a light chain or a heavy chain of a GCGR antibody via a peptide linker.

Provided herein is a GLP-1 fusion protein, comprising a GCGR antibody and two GLP-1 fragments; the fusion protein connects the carboxy terminal of a GLP-1 fragment with the amino terminal of a GCGR antibody light chain through a peptide linker sequence (Linker): N'-GLP-1-Linker-R-C'; or connects the carboxy terminal of a GLP-1 fragment to the amino terminal of a GCGR antibody heavy chain: N'-GLP-1-Linker-R-C'; wherein: N' represents an amino terminal of a fusion protein polypeptide chain, C' represents a carboxy terminal of a fusion protein polypeptide chain, GLP-1 represents a GLP-1 fragment, R is the amino acid sequence of the light chain or heavy chain of a GCGR antibody, and Linker represents a peptide linker sequence.

Provided herein is a GLP-1 fusion protein comprising a GCGR antibody and two reverse GLP-1 fragments; the fusion protein connects the amino terminal of a reverse GLP-1 fragment with the carboxy terminal of a GCGR antibody light chain: N'-R-Linker-reverse GLP-1-C'; or connects the amino terminal of a reverse GLP-1 fragment through a peptide linker sequence (Linker) with the carboxy terminal of a GCGR antibody heavy chain: N'-R-Linker-reverse GLP-1-C'; wherein: N' represents an amino terminal of a fusion protein polypeptide chain, C' represents the carboxy terminal of a fusion protein polypeptide chain, and the reverse GLP-1 represents a reverse GLP-1 fragment, R is the amino acid sequence of the light chain or heavy chain of a GCGR antibody, and Linker represents a peptide linker sequence.

Provided herein is a polynucleotide acid encoding a GCGR antibody described herein.

Provided herein is a polynucleotide acid encoding a fusion protein of GCGR antibody and GLP-1 described herein.

Provided herein is a vector including a polynucleotide acid encoding a GCGR antibody described herein.

Provided herein is a vector including a polynucleotide acid encoding a fusion protein of GCGR antibody and GLP-1 described herein.

Provided herein is a host cell line comprising a vector described herein.

Provided herein is a pharmaceutical composition comprising a GCGR antibody described herein and a pharmaceutically acceptable carrier.

Provided herein is a pharmaceutical composition comprising a fusion protein of GCGR antibody and GLP-1 described herein and a pharmaceutically acceptable carrier.

Provided herein is the use of a GCGR antibody described herein in the preparation of a medicament for treating, preventing or ameliorating T2D.

Provided herein is the use of a fusion protein of GCGR antibody and GLP-1 described herein in the preparation of a medicament for treating, preventing or ameliorating T2D.

Provided herein is the use of a GCGR antibody described herein in the preparation of a medicament for treating, preventing or ameliorating the complications of T2D.

Provided herein is the use of a fusion protein of GCGR antibody and GLP-1 described herein in the preparation of a medicament for treating, preventing or ameliorating the complications of T2D.

Provided herein is the use of a GCGR antibody described herein in the preparation of a medicament for treating, preventing or ameliorating hyperglycemia.

Provided herein is the use of a fusion protein of GCGR antibody and GLP-1 described herein in the preparation of a medicament for treating, preventing or ameliorating hyperglycemia.

Provided herein is the use of a GCGR antibody described herein in the preparation of a medicament for treating, preventing or ameliorating metabolic syndrome.

Provided herein is the use of a fusion protein of GCGR antibody and GLP-1 described herein in the preparation of a medicament for treating, preventing or ameliorating metabolic syndrome.

Provided herein is the use of a GCGR antibody described herein in the preparation of a medicament for treating, preventing or ameliorating dyslipidemia.

Provided herein is the use of a fusion protein of GCGR antibody and GLP-1 described herein in the preparation of a medicament for treating, preventing or ameliorating dyslipidemia.

Provided herein is the use of a GCGR antibody described herein in the preparation of a medicament for treating, preventing or ameliorating simultaneously two or more diseases of hyperglycemia, T2D, metabolic syndrome or dyslipidemia.

Provided herein is the use of a fusion protein of GCGR antibody and GLP-1 described herein in the preparation of a medicament for treating, preventing or ameliorating simultaneously two or more diseases of hyperglycemia, T2D, metabolic syndrome or dyslipidemia.

Provided herein is a method to treat, prevent, or improve hyperglycemia comprising giving subjects a therapeutically effective dose of a GCGR antibody described herein.

Provided herein is a method to treat, prevent, or improve hyperglycemia comprising giving subjects a therapeutically effective dose of a fusion protein of GCGR antibody and GLP-1 described herein.

Provided herein is a method to treat, prevent, or improve T2D comprising giving subjects a therapeutically effective dose of a GCGR antibody described herein.

Provided herein is a method to treat, prevent, or improve T2D comprising giving subjects a therapeutically effective dose of a fusion protein of GCGR antibody and GLP-1 described herein.

Provided herein is a method to treat, prevent, or improve metabolic syndrome comprising giving subjects a therapeutically effective dose of a GCGR antibody described herein.

Provided herein is a method to treat, prevent, or improve metabolic syndrome comprising giving subjects a therapeutically effective dose of a fusion protein of GCGR antibody and GLP-1 described herein.

Provided herein is a method to treat, prevent, or improve dyslipidemia comprising giving subjects a therapeutically effective dose of a GCGR antibody described herein.

Provided herein is a method to treat, prevent, or improve dyslipidemia comprising giving subjects a therapeutically effective dose of a fusion protein of GCGR antibody and GLP-1 described herein.

Provided herein is a method to treat, prevent, or improve one or more syndromes of hyperglycemia, T2D, metabolic syndrome or dyslipidemia comprising giving subjects a therapeutically effective dose of a GCGR antibody described herein.

Provided herein is a method to treat, prevent, or improve one or more syndromes of hyperglycemia, T2D, metabolic syndrome or dyslipidemia comprising giving subjects a therapeutically effective dose of a fusion protein of GCGR antibody and GLP-1 described herein.

DETAILED DESCRIPTION

Definitions

Figure 1:
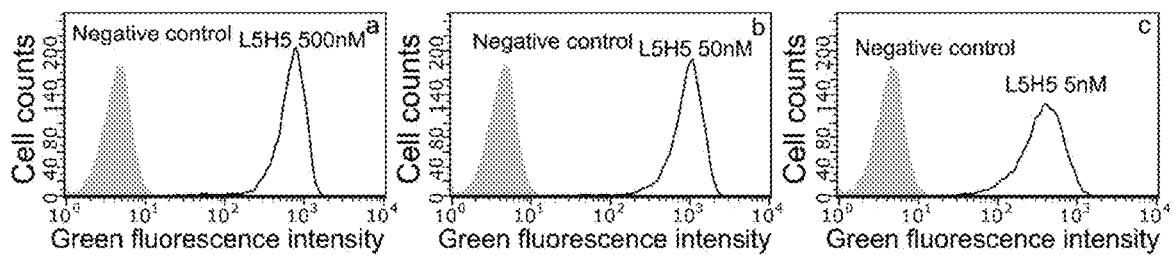
FIG. 1 shows the FACS test of the specific binding of the mouse ascites antibody L5H5 (comprising SEQ ID NO: 85 and SEQ ID NO: 95) to hGCGR, the gray peak is the negative control of 500 nM of the mouse ascites antibody L5H5 binding to the CHO-DHFR–, solid line peaks represent the binding peaks of 500 nM (1a), 50 nM (1b) or 5 nM (1c), respectively, of the mouse ascites antibody L5H5 to CHO-DHFR-hGCGR, their significant right-shift relative to the gray peak indicates that L5H5 has a specific binding to CHO-DHFR-hGCGR.

Unless defined otherwise herein, scientific and technical terms shall have the meanings understood by ordinary technicians in the field. Generally, the nomenclature and techniques related to pharmacology, biology, biochemistry, cell and tissue culture, molecular biology, immunology, microbiology, genetics and protein nucleic acid chemistry, as well as hybridization are well-known and commonly used in the field.

This invention used standard single-letter or three-letter abbreviations to indicate polynucleotide and polypeptide sequences. When the polypeptide sequence is written, the first amino acid residue (N') with the amino group is at the far left and the last amino acid residue (C') with the carboxyl group is at the far right, for example, the GLP-1 fragment sequence involved in this invention: SEQ ID NO:119, SEQ ID NO:120, SEQ ID NO:121, SEQ ID NO:122, and SEQ ID NO:123. Reverse polypeptide sequence refers to a polypeptide sequence wherein amino acids arranged in a reversed order as to the original, for example the reverse GLP-1 fragment sequences converted from the above GLP-1 fragment sequences: SEQ ID NO: 127, SEQ ID NO: 128, SEQ ID NO: 129, SEQ ID NO: 130, and SEQ ID NO: 131. The 5' ends of the upstream chains of single-stranded and double-stranded nucleic acid sequences on the left and their 3' ends are on the right. The specific portion of a polypeptide can be represented by an amino acid residue number, such as amino acids 80 to 130, or represented by the actual residue of the site, such as Lys80 to Lys130. The specific polypeptide or polynucleotide sequence can also be described by explaining its difference from the reference sequence.

The terms "peptide", "polypeptide" and "protein" refer to a molecule containing two or more amino acids that are interlinked by a peptide bond. These terms cover, for example, natural and artificial proteins, and peptide analogues of protein (such as mutant proteins, variants, and fusion proteins) and proteins that are post translational or otherwise covalent or non-covalent modified. A peptide, polypeptide, or protein can be monomeric or a polymer.

The term "polypeptide fragment" refers to a polypeptide that has an amino terminus and/or a carboxyl terminus missing from the corresponding full-length protein. For example, the fragment length can be at least 5, 6, 7, 8, 9, 10, 11, 12, 13, 14, 15, 20, 50, 70, 80, 90, 100, 150 or 200 amino acids. The fragment length can be, for example, up to 1,000, 750, 500, 250, 200, 175, 150, 125, 100, 90, 80, 70, 60, 50, 40, 30, 20, 15, 14, 13, 12, 11, or 10 amino acids. The fragment may further contain one or more additional amino acids at one end or both, such as amino acid sequences from different natural proteins (e. g., Fc or leucine zipper domains) or artificial amino acid sequences (e. g., artificial joint sequences).

The peptides in this invention include peptides modified for any reason, and by any means. For example, by (1) decreasing proteolysis sensitivity, (2) decreasing oxidation sensitivity, (3) altering the affinity for forming protein complexes, (4) altering binding affinity, and (5) conferring or modifying other physicochemical or functional properties. Analogue contains a mutant protein of a polypeptide. For example, can be perform single or multiple amino acid substituted (e.g., conservative amino acid substitutions) in natural sequences (e.g., outside the domain of the polypeptide that forms intramolecular contact). The "conserved amino acid substitution" is the one that does not significantly change the structural characteristics of the parent sequence (e.g., The substitution of amino acids shall not destroy the helices present in the parent sequence, or interfere with other secondary structural types necessary to give the parent sequence its properties or function).

A "mutant" of a polypeptide, wherein an amino acid sequence containing the insertion, deletion, and/or replacement of one or more residues in an amino acid sequence relative to another polypeptide sequence. The variants in this invention included fusion proteins.

A "derivative" of a polypeptide is a chemically modified polypeptide, for example, by binding to other chemical components such as polyethylene glycol, albumin (such as human serum albumin), phosphorylation, and glycosylation.

Unless otherwise stated, the term "antibody" includes antibodies with two full-length heavy chains and two full-length light chains, as well as their derivatives, variants, fragments, and mutated proteins, instances are listed below.

The term "antibody" is a protein that contains the antigen-binding portion and optionally the scaffold or framework portion that allows the antigen-binding portion to adopt a conformation that promotes the binding of the antibody to the antigen. Examples of antibodies include complete antibodies, antibody fragments (such as the antigen-binding portion of an antibody), antibody derivatives, and antibody analogues. For example, the antibody may contain alternative protein scaffolds or artificial scaffolds with transplanted CDRs or derivatives of CDR s. The scaffold includes, but not limited to an antibody-derived scaffold that is introduced, such as one that stabilizes the three-dimensional structure of the antibody, and such as a fully synthetic scaffold for biocompatible polymer. See for example, Korndorfer et al., 2003, *Proteins* 53:121-129; Roque et al., 2004, *Biotechnol. Prog.* 20:639-654. In addition, the antibody may be either a mock peptide antibody ("PAMs") or a scaffold containing mock antibodies, therein use of fibrin ligands as scaffolds.

Antibodies may have structures such as innate immunoglobulin. "Immunoglobulin" is a tetramer molecule. In natural immunoglobulin, each tetramer consists of two identical polypeptide chain pairs, each pair having a "light" chain (approx. 25 k Da) and a "heavy" chain (approx. 50-70 kDa). The amino terminus of each chain includes a variable domain of about 100 to 110 amino acids, which is mainly related to antigen recognition. The carboxyl terminus of each chain determines the constant region mainly associated with the effect of the effectors. The human antibody light chain is divided into κ and λ light chains. The heavy chains were divided into μ, δ, α, or ε, and determined the same type of antigen, such as IgM, IgD, IgG, IgA, and IgE. In light and heavy chains, the variable and constant regions are connected by the "J" region of about 12 or more amino acids, and the heavy chain also includes the "D" region of about 10 more amino acids. Refer to Fundamental Immunology ch.7 (edited by Paul, 2nd edition, Raven Press, 1989). Variable regions of each light/heavy chain pair form antibody binding sites, in this way a complete immunoglobulin has two binding sites.

The innate immunoglobulin chains exhibit the same basic structure of a relatively conservative skeletal region (FR) connected by three highly variable regions, also known as the complementary decision region or CDRs. From the N end to the C end, the light and heavy chains contain the structural domains FR1, CDR1, FR2, CDR2, FR3, CDR3, and FR4. The distribution of amino acids in all structural domains was consistent with Kabat et al. in Sequences of Proteins of Immunological Interest, 5th edition, U.S. Dept. Of Health and Human Services, PHS, NIH, NIH Publication No. 91-3242, 1991.

Unless otherwise specified, "antibody" means either the intact immunoglobulin or the antigen-binding portion of that can compete specifically binding to intact antibody. Antigen-binding portion can be produced by recombinant DNA techniques, enzymatic or chemical cleavage of intact antibodies. Antigen-binding portion includes, in particular, Fab, Fab', F(ab)2, Fv, structural domain antibodies (dAbs), contain complementary decision area (CDRs), single-chain antibody (scFv), chimeric antibody, double chains antibody (diabodies), three chains antibodies (triabodies), four chains (tetrabodies) and a polypeptide that contains at least a portion of the immunoglobulin that binds to a polypeptide-specific antigen.

The Fab fragment is a univalent fragment with $V_L$, $V_H$, $C_L$, and $C_{H1}$ domains; The F(ab')2 fragment is a divalent fragment have two Fab fragments connected by a disulfide bond in the hinge region; Fv fragments have $V_H$ and $V_L$ domains; dAb fragments have $V_H$ domain, $V_L$ domain, or antigen binding fragments of $V_H$ or $V_L$ domain (US patent numbers U.S. Pat. Nos. 6,846,634 and 6,696,245; US patent application public numbers US 2005/0202512, US 2004/0202995, US 2004/0038291, US 2004/0009507, and US 2003/0039958; Ward et al., 1989, *Nature* 341:544-546).

Single-chain antibody (scFv) is a fusion protein in which the $V_L$ and $V_H$ regions are joined by a connector (for example, a synthetic sequence of amino acid residues) to form a continuous protein antibody, therein the connector is long enough to allow the protein chain to fold back to itself and to form a univalent antigen binding site (See, for example, Bird et al., 1988, *Science* 242:423-26; and Huston et al., 1988, *Proc. Natl. Acad. Sci. U.S.A.* 85:5879-83).

A double-chain antibody is a divalent antibody contain two polypeptide chains, each of which contains the $V_H$ and $V_L$ regions connected by a joint that is so short that it does not allow pairing of the two domains on the same chain. Therefore, each domain is allowed to pair with a complementary domain on another polypeptide chain (See, for example, Holliger et al., 1993, *Proc. Natl. Acad. Sci. U.S.A.* 90:6444-48; Poljak et al., 1994, *Structure* 2:1121-23). If the two polypeptide chains of the double-stranded antibody are identical, the double-stranded antibody result from their pairing will have the same antigen-binding site. Polypeptide chains with different sequences can be used to prepare double-stranded antibodies with different antigen binding sites. Similarly, three-chain and four-chain antibodies are the antibody that contain three and four polypeptide chains and form three and four antigen binding sites, which may be the same or different.

In certain embodiments, the method that Kabat et al., described in Sequences of Proteins of Immunological Interest, 5th edition, U.S. Dept. Of Health and Human Services, PHS, NIH, NIH Publication No. 91-3242, 1991, is used to identify the complementary decision region (CDRs) and framework region (FR) of a given antibody. One or more CDRs can be incorporated into a molecule either covalently or noncovalently to make it an antibody. The antibody can incorporate a larger polypeptide chain into the CDR(s). CDR(s) can be covalently attached to another polypeptide chain or can be non-covalently incorporated into CDR(s). CDRs allows antibodies specifically binding to specific associated antigens.

Antibodies can have one or more binding sites. If there is more than one binding site, the binding site can be the same or different from another. For example, natural human immunoglobulin usually has two identical binding sites, while "bi-specific" or "bifunctional" antibodies have two different binding sites.

The term "murine antibody" includes antibodies having one or more variable and constant regions derived from mouse immunoglobulin sequences.

The term "humanized antibody" is an antibody made by transplanting the sequence of complementary decision regions of mouse antibody molecules into the framework of human antibody variable regions.

The terms "antigen-binding domain," "antigen-binding region," or "antigen-binding site" are the parts of an antibody that contain amino acid residues that interact with an antigen and contribute to its specificity and affinity for the antigen. For antibodies that bind specifically to their antigens, this will include at least part of at least one of its CDR domains.

The term "epitope" is the part of a molecule that binds to (for example, by an antibody) the antibody. An epitope may contain a discontinuous part of a molecule (for example, in a polypeptide, the amino acid residues that are discontinuous in the first order of the polypeptide are close enough to each other in the tertiary and quaternary structures of the polypeptide to be bound by an antibody).

The "same percentage" of two polynucleotides or two polypeptide sequences is determined using the GAP computer program's (GCG Wisconsin Package; a part of version 10.3 (Accelrys, San Diego, Calif.)) default parameters comparison sequence.

The terms "polynucleotide", "oligonucleotide" and "nucleic acid" can be used alternatively throughout the full text and include DNA molecules (e.g., cDNA or genomic DNA), RNA molecules (e.g., mRNA), DNA or RNA analogues and their hybrids produced using nucleotide analogues (e.g., peptide nucleic acids and non-natural nucleotide analogues). Nucleic acid molecules can be single or double stranded. In one embodiment, the nucleic acid molecules contained in this invention encode the antibody or its fragments, derivatives, mutant proteins, or variants continuous open reading frame.

If their sequences can be reversed and parallel, two single-stranded nucleotides are "complementary" to each other, so that each nucleotide in one polynucleotide is opposite to the complementary nucleotide in the other, no gaps are introduced and no unpaired nucleotides are found at the 5' or 3' ends of each sequence. If two polynucleotides can interbreed under moderately strict conditions, one polynucleotide is "complementary" to the other. Thus, one polynucleotide may be complementary to another polynucleotide, but not its complementary sequence.

The term "vector" is a nucleic acid that can be used to introduce another nucleic acid connected to it into a cell. One type of vector is a "plasmid", refer to a linear or circular double-stranded DNA molecule that can be attached to an additional nucleic acid segment. Another type of vector is a viral vector (e.g., replication-defective retroviruses, adenoviruses, and adenoviral companion viruses) in which additional DNA segments can be introduced into the viral genome. Some vectors can replicate autonomously in the host cells into which they are introduced (For example, bacterial carriers containing the origin of bacterial replication and the free-type mammalian carriers). Other vectors (for example, non-free-type mammalian vectors) are integrated into the host cell genome when introduced into the host cell and thus replicate with the host genome. "Expression vector" is the type of carrier that can guide the expression of selected polynucleotides.

If the regulatory sequence affects the expression of a nucleotide sequence (for example, expression level, time, or site), then the nucleotide sequence is "operationally linked" to the regulatory sequence. The "regulatory sequence" is the nucleic acid that affects the expression (for example, expression level, time, or site) of the nucleic acid with which it is operationally linked. Regulatory genes, for example, act directly on regulated nucleic acids or through one or more other molecules (e.g., polynucleotides that bind to regulatory sequences and/or nucleic acids). Examples of regulatory sequences include promoters, enhancers, and other expression control elements (e.g., polyadenylation signals). Further examples of regulatory sequences can be described such as Goeddel, 1990, *Gene Expression Technology: Methods in Enzymology*, Volume 185, Academic Press, San Diego, Calif.; And Baron et al., 1995, Nucleic Acids Res. 23:3605-06.

The term "host cell" refers to a cell used to express a nucleic acid such as that provided this article. The host cell may be a prokaryote, such as *E. coli*, or it can be eukaryotes, such as unicellular eukaryotes (yeast or other fungi, for example), plant cells (such as tobacco or tomato plant cells), animal cells (for example, cells, monkey, hamster cells, cells or insect cells of rats and mice) or hybridoma. Usually, the host cell is a culture cell that can be transformed or transfected with a peptide encoding nucleic acid, which can then be expressed in the host cell. The phrase "recombinant host cell" can be used to describe a host cell transformed or transfected with an expected expression of nucleic acid. The host cell may also be a cell that contains the nucleic acid but does not express it at the desired level, unless regulatory sequences are introduced to the host cell so that it is operationally linked to the nucleic acid. It should be understood that the term "host cell" refers to not only the specific subject cell but also to the progeny or possible progeny of that cell. Due to certain modifications occurring in subsequent generations, such as mutations or environmental influences, the progeny may in fact be different from the parent cell but still fall within the scope of the terminology used in this invention.

Glucagon Receptor

Glucagon receptor belongs to type B of the seven-transmembrane G protein-coupled receptor family. The receptor is coupled to one or more intracellular signaling pathways by a heterotrimeric guanine nucleotide-binding protein (G protein) (Jelinek et al., 1993, *Science* 259:1614-16). Up to now, studies show that GCGR is mainly expressed in liver, kidney, brain, fat tissue, pancreas and heart (Ahren et al., 2015, *Peptides* 67:74-81; Jazayeri et al., 2016 *Nature* 533:274-7), and is involved in the glucose metabolism in human, therefore closely related to diabetes, dyslipidemia (Lee et al., 2016, *Diabetologia* 59:1372-5). Both "human GCGR" and "hGCGR" used in this paper refer to human glucagon receptor. "Mouse GCGR" and "mGCGR" used in this paper refer to mouse glucagon receptor.

In one embodiment, the antibody presented here is an antibody specifically binding to human GCGR. In another embodiment, the antibody presented here is an antibody specifically binding to GCGR on the cell membrane, and the antibody can inhibit or block the transduction of glucagon signals in these cells. In another embodiment, the antibody presented here is an antibody specifically binding to human GCGR and can bind to GCGR of other species (e.g., monkeys and mice) and block the glucagon signaling in these species. In a further embodiment, the antibodies presented here is a murine antibody that binds to human GCGR and can bind to GCGR of other species (e.g., monkey).

In one embodiment, the amino acid and polynucleotide sequences of GCGR are listed below, with sequence data from the GeneBank database of the US National center of biotechnology information (NCBI) and the Uniprot database of the European Bioinformatics Institute for biological information.

Human (*Homo sapiens*) polynucleotide (SEQ ID NO:77); accession number: BC104854;
Human (*Homo sapiens*) amino acid (SEQ ID NO:73); accession number: P47871;
Monkey (*Rhesus macaque*) polynucleotide (SEQ ID NO:78); accession number: XM_015120592;
Monkey (*Rhesus macaque*) amino acid (SEQ ID NO:74); accession number: A0A1D5QZY8;
Rat (*Rattus norvegicus*) polynucleotide (SEQ ID NO: 79); accession number: X68692;
Rat (*Rattus norvegicus*) amino acid (SEQ ID NO: 75); accession number: P30082;
Mouse (*Mus musculus*) polynucleotide (SEQ ID NO:80); accession number: BC031885; and
Mouse (*Mus musculus*) amino acid (SEQ ID NO:76); accession number: Q61606.

Glucagon Receptor (GCGR) Antibody

In one embodiment, provided herein is the GCGR antibody. In another embodiment, the GCGR antibody provided herein is the complete GCGR antibody. In another embodiment, the GCGR antibody provided herein is GCGR antibody fragment. In another embodiment, the GCGR antibody provided herein is a derivative of GCGR antibody. In another embodiment, the GCGR antibody provided herein is the GCGR antibody mutant protein. In a further embodiment, the GCGR antibody provided herein is the variant of GCGR antibody.

In one embodiment, the GCGR antibody provided herein comprises one, two, three, four, five, or six amino acid sequences, each of which is independently selected from the amino acid sequences listed below:

a. Light chain CDR1 amino acid sequence: SEQ ID NO: 1, SEQ ID NO: 4, SEQ ID NO: 7, SEQ ID NO: 10, SEQ ID NO: 13, SEQ ID NO: 16, SEQ ID NO: 18, and SEQ ID NO: 20;
b. Light chain CDR2 amino acid sequence: SEQ ID NO: 2, SEQ ID NO: 5, SEQ ID NO: 8, SEQ ID NO: 11, and SEQ ID NO: 14;
c. Light chain CDR3 amino acid sequence: SEQ ID NO: 3, SEQ ID NO: 6, SEQ ID NO: 9, SEQ ID NO: 12, SEQ ID NO: 15, SEQ ID NO: 17, SEQ ID NO: 19, and SEQ ID NO: 21;
d. Heavy chain CDR1 amino acid sequence: SEQ ID NO: 22, SEQ ID NO: 25, and SEQ ID NO: 28, SEQ ID NO: 31, and SEQ ID NO: 34;
e. Heavy chain CDR2 amino acid sequence: SEQ ID NO: 23, SEQ ID NO: 26, SEQ ID NO: 29, SEQ ID NO: 32, and SEQ ID NO: 35; and
f. Heavy chain CDR3 amino acid sequence: SEQ ID NO: 24, SEQ ID NO: 27, SEQ ID NO: 30, SEQ ID NO: 33, and SEQ ID NO: 36.

Table 1 lists the amino acid sequences of light chain CDRs of the GCGR antibody provided herein, as well as the corresponding polynucleotide coding sequences. Table 2 lists the amino acid sequences of heavy chain CDRs of the GCGR antibody provided herein, as well as the corresponding polynucleotides coding sequences.

TABLE 1 light chain CDR amino acid sequences and polynucleotide coding sequences

|  | CDR1 | CDR2 | CDR3 |
|---|---|---|---|
| A-1 Nucleic Acid | agtgccagctcaagtgtaatttacatgtac (SEQ ID NO: 37) | gacacatccaacctggtttct (SEQ ID NO: 38) | cagcagtacagtggttacccgta cacg (SEQ ID NO: 39) |
| A-1 Amino Acid | SASSSVIYMY (SEQ ID NO: 1) | DTSNLVS (SEQ ID NO: 2) | QQYSGYPYT (SEQ ID NO: 3) |
| A-2 Nucleic Acid | aaatctagtcagaggattgtacatagtgatg ggaagacctatttagaa (SEQ ID NO: 40) | aaagtttccaaccgattttct (SEQ ID NO: 41) | tttcaaggttcacatattccgtgg acg (SEQ ID NO: 42) |
| A-2 Amino Acid | KSSQRIVHSDGKTYLE (SEQ ID NO: 4) | KVSNRFS (SEQ ID NO: 5) | FQGSHIPWT (SEQ ID NO: 6) |

TABLE 1-continued light chain CDR amino acid sequences and polynucleotide coding sequences

| | CDR1 | CDR2 | CDR3 |
|---|---|---|---|
| A-3 Nucleic Acid | agagccagcgaaagtgttgataattttggct ttagttttatgaac (SEQ ID NO: 43) | agtgcatccaaccaaggatcc (SEQ ID NO: 44) | cagcaaagtaaggagattcctttcacg (SEQ ID NO: 45) |
| A-3 Amino Acid | RASESVDNFGFSFMN (SEQ ID NO: 7) | SASNQGS (SEQ ID NO: 8) | QQSKEIPFT (SEQ ID NO: 9) |
| A-4 Nucleic Acid | agggcctccggcaacatccacaattacct gacc (SEQ ID NO: 46) | aatgccaaggccctggcc (SEQ ID NO: 47) | ctgcacttttggagcagcccctgacc (SEQ ID NO: 48) |
| A-4 Amino Acid | RASGNIHNYLT (SEQ ID NO: 10) | NAKALA (SEQ ID NO: 11) | LHFWSSPLT (SEQ ID NO: 12) |
| A-5 Nucleic Acid | aagtcctcccagtccctgctgtactccaac aatcagaagaattacctggcc (SEQ ID NO: 49) | tgggcctccacaagggagtc c (SEQ ID NO: 50) | cagcagtactacagctaccccctgacc (SEQ ID NO: 51) |
| A-5 Amino Acid | KSSQSLLYSNNQKNYLA (SEQ ID NO: 13) | WASTRES (SEQ ID NO: 14) | QQYYSYPLT (SEQ ID NO: 15) |
| A-6 Nucleic Acid | agggcctccggcaacatccacaattacct gacc (SEQ ID NO: 46) | aatgccaaggccctggcc (SEQ ID NO: 47) | ctgcacttttggagcagcccctgacc (SEQ ID NO: 48) |
| A-6 Amino Acid | RASGNIHNYLT (SEQ ID NO: 10) | NAKALA (SEQ ID NO: 11) | LHFWSSPLT (SEQ ID NO: 12) |
| A-7 Nucleic Acid | aagtcctcccagtccctgctgtactccaac aatcagaagaattacctggcc (SEQ ID NO: 49) | tgggcctccacaagggagtc c (SEQ ID NO: 50) | cagcagtactacagctaccccctgacc (SEQ ID NO: 51) |
| A-7 Amino Acid | KSSQSLLYSNNQKNYLA (SEQ ID NO: 13) | WASTRES (SEQ ID NO: 14) | QQYYSYPLT (SEQ ID NO: 15) |
| A-8 Nucleic Acid | aagtccagccagagtgttttatatagctcca acaataagaactacttagct (SEQ ID NO: 52) | tgggcctccacaagggagtc c (SEQ ID NO: 50) | cagcaatcttatagtactccgctcact (SEQ ID NO: 53) |
| A-8 Amino Acid | KSSQSVLYSSNNKNYLA (SEQ ID NO: 16) | WASTRES (SEQ ID NO: 14) | QQSYSTPLT (SEQ ID NO: 17) |
| A-9 Nucleic Acid | aagtccagccagagtgttttatacacctcca acaataacaactacttagct (SEQ ID NO: 54) | tgggcctccacaagggagtc c (SEQ ID NO: 50) | cagcaatatttagtactccgatcacc (SEQ ID NO: 55) |
| A-9 Amino Acid | KSSQSVLYTSNNNNYLA (SEQ ID NO: 18) | WASTRES (SEQ ID NO: 14) | QQYFSTPIT (SEQ ID NO: 19) |
| A-10 Nucleic Acid | aagtccagccagagtgttttatacaaccccc aacagtaagaattacttcgct (SEQ ID NO: 56) | tgggcctccacaagggagtc c (SEQ ID NO: 50) | caacaatattatatcactccgtacact (SEQ ID NO: 57) |
| A-10 Amino Acid | KSSQSVLYNPNSKNYFA (SEQ ID NO: 20) | WASTRES (SEQ ID NO: 14) | QQYYITPYT (SEQ ID NO: 21) |

TABLE 2 heavy chain CDR amino acid sequences and polynucleotide coding sequences

| | | CDR1 | CDR2 | CDR3 |
|---|---|---|---|---|
| A-1 | Nucleic Acid | ggattcactttcagtaactttgga atgcac (SEQ ID NO: 58) | tacattagtagaggcagtagcaacatct actatgcagacacagtgaagggc (SEQ ID NO: 59) | accccctatgattacgacggatatt actatgctatggactac (SEQ ID NO: 60) |
| A-1 | Amino Acid | GFTFSNFGMH (SEQ ID NO: 22) | YISRGSSNIYYADTVKG (SEQ ID NO: 23) | TPYDYDGYYYAMDY (SEQ ID NO: 24) |
| A-2 | Nucleic Acid | ggatacgccctcactaactact ggatagat (SEQ ID NO: 61) | aatgtttaccctgaaggtggtfttgtcaa ttacaatgagaactttaagggc (SEQ ID NO: 62) | gattacgacgggtttgacttc (SEQ ID NO: 63) |
| A-2 | Amino Acid | GYALTNYWID (SEQ ID NO: 25) | NVYPEGGFVNYNENFKG (SEQ ID NO: 26) | DYDGFDF (SEQ ID NO: 27) |
| A-3 | Nucleic Acid | ggatacacattcaccagttatatt atgcac (SEQ ID NO: 64) | tatattaatccttacaatgaaggcactaa gtataatgaggcgttcgaagac (SEQ ID NO: 65) | gatactacgataggtgactggtact tcgatgtt (SEQ ID NO: 66) |
| A-3 | Amino Acid | GYTFTSYIMH (SEQ ID NO: 28) | YINPYNEGTKYNEAFED (SEQ ID NO: 29) | DTTIGDWYFDV (SEQ ID NO: 30) |
| A-4 | Nucleic Acid | ggctactcaatcaccagtgatta tgcctggacc (SEQ ID NO: 67) | tacataagtttcactggtaccactagcta cacccatctctcaaaagt (SEQ ID NO: 68) | agtgtgattttactatagactcc (SEQ ID NO: 69) |
| A-4 | Amino Acid | GYSITSDYAWT (SEQ ID NO: 31) | YISFTGTTSYTPSLKS (SEQ ID NO: 32) | SVIFTIDS (SEQ ID NO: 33) |
| A-5 | Nucleic Acid | ggatacacattcactgaataca ccatgcac (SEQ ID NO: 70) | ggtattaatcctgacaatggtggtccta gctacagccagaaattcaagggc (SEQ ID NO: 71) | gaaacacatgattacgacaagttt gcttac (SEQ ID NO: 72) |
| A-5 | Amino Acid | GYTFTEYTMH (SEQ ID NO: 34) | GINPDNGGPSYSQKFKG (SEQ ID NO: 35) | ETHDYDKFAY (SEQ ID NO: 36) |
| A-6 | Nucleic Acid | ggctactcaatcaccagtgatta tgcctggacc (SEQ ID NO: 67) | tacataagtttcactggtaccactagcta cacccatctctcaaaagt (SEQ ID NO: 68) | agtgtgattttactatagactcc (SEQ ID NO: 69) |
| A-6 | Amino Acid | GYSITSDYAWT (SEQ ID NO: 31) | YISFTGTTSYTPSLKS (SEQ ID NO: 32) | SVIFTIDS (SEQ ID NO: 33) |
| A-7 | Nucleic Acid | ggatacacattcactgaataca ccatgcac (SEQ ID NO: 70) | ggtattaatcctgacaatggtggtccta gctacagccagaaattcaagggc (SEQ ID NO: 71) | gaaacacatgattacgacaagttt gcttac (SEQ ID NO: 72) |
| A-7 | Amino Acid | GYTFTEYTMH (SEQ ID NO: 34) | GINPDNGGPSYSQKFKG (SEQ ID NO: 35) | ETHDYDKFAY (SEQ ID NO: 36) |

In one embodiment, the antibody provided herein comprises a sequence different from one of the CDR amino acid sequences listed in Tables 1 and 2 by five, four, three, two or one single amino acid addition, replacement, and/or deletion. In another embodiment, the antibody provided herein contains a sequence different from one of the CDR amino acid sequences listed in Tables 1 and 2 by four, three, two or one single amino acid addition, replacement, and/or deletion.

In another embodiment, the antibody provided herein contains a sequence different from one of the CDR amino acid sequences listed in Tables 1 and 2 by three, two or one single amino acid addition, replacement, and/or deletion.

In another embodiment, the antibody provided herein contains a sequence different from one of the CDR amino acid sequences listed in Tables 1 and 2 by two or one single amino acid addition, replacement, and/or deletion.

In further embodiments, the antibody provided herein contains a sequence that differs from one of the CDR amino acid sequences listed in Tables 1 and 2 by a single amino acid addition, replacement, and/or deletion.

In one embodiment, the GCGR antibody provided herein comprises one or two amino acid sequences, wherein each amino acid sequence is independently selected from the amino acid sequences listed below:

a. Light chain CDR1 amino acid sequences: SEQ ID NO: 1, SEQ ID NO: 4, SEQ ID NO: 7, SEQ ID NO: 10, SEQ ID NO: 13, SEQ ID NO: 16, SEQ ID NO: 18, and SEQ ID NO: 20; and b. Heavy chain CDR1 amino acid sequences: SEQ ID NO: 22, SEQ ID NO: 25, and SEQ ID NO: 28, SEQ ID NO: 31, and SEQ ID NO: 34.

In another embodiment, the GCGR antibody provided herein comprises one or two amino acid sequences, wherein each amino acid sequence is independently selected from the amino acid sequences listed below:
- a. Light chain CDR2 amino acid sequences: SEQ ID NO: 2, SEQ ID NO: 5, SEQ ID NO: 8, SEQ ID NO: 11, and SEQ ID NO: 14; and
- b. Heavy chain CDR2 amino acid sequences: SEQ ID NO: 23, SEQ ID NO: 26, SEQ ID NO: 29, SEQ ID NO: 32, and SEQ ID NO: 35.

In another embodiment, the GCGR antibody provided herein comprises one or two amino acid sequences, wherein each amino acid sequence is independently selected from the amino acid sequences listed below:
- a. Light chain CDR3 amino acid sequences: SEQ ID NO: 3, SEQ ID NO: 6, SEQ ID NO: 9, SEQ ID NO: 12, and SEQ ID NO: 15, SEQ ID NO: 17, SEQ ID NO: 19, and SEQ ID NO: 21; and
- b. Heavy chain CDR3 amino acid sequences: SEQ ID NO: 24, SEQ ID NO: 27, SEQ ID NO: 30, SEQ ID NO: 33, and SEQ ID NO: 36.

In another embodiment, the GCGR antibody provided herein comprises one, two, three or four amino acid sequences, wherein each amino acid sequence is independently selected from the amino acid sequences listed below:
- a. Light chain CDR1 amino acid sequences: SEQ ID NO: 1, SEQ ID NO: 4, SEQ ID NO: 7, SEQ ID NO: 10, SEQ ID NO: 13, SEQ ID NO: 16, SEQ ID NO: 18, and SEQ ID NO: 20;
- b. Heavy chain CDR1 amino acid sequences: SEQ ID NO: 22, SEQ ID NO: 25, and SEQ ID NO: 28, SEQ ID NO: 31, and SEQ ID NO: 34;
- c. Light chain CDR2 amino acid sequences: SEQ ID NO: 2, SEQ ID NO: 5, SEQ ID NO: 8, SEQ ID NO: 11, and SEQ ID NO: 14; and
- d. Heavy chain CDR2 amino acid sequences: SEQ ID NO: 23, SEQ ID NO: 26, SEQ ID NO: 29, SEQ ID NO: 32, and SEQ ID NO: 35.

In another embodiment, the GCGR antibody provided herein comprises one, two, three, or four amino acid sequences, wherein each amino acid sequence is independently selected from the amino acid sequences listed below:
- a. Light chain CDR1 amino acid sequences: SEQ ID NO: 1, SEQ ID NO: 4, SEQ ID NO: 7, SEQ ID NO: 10, SEQ ID NO: 13, SEQ ID NO: 16, SEQ ID NO: 18, and SEQ ID NO: 20;
- b. Heavy chain CDR1 amino acid sequences: SEQ ID NO: 22, SEQ ID NO: 25, and SEQ ID NO: 28, SEQ ID NO: 31, and SEQ ID NO: 34;
- c. Light chain CDR3 amino acid sequences: SEQ ID NO: 3, SEQ ID NO: 6, SEQ ID NO: 9, SEQ ID NO: 12, and SEQ ID NO: 15, SEQ ID NO: 17, SEQ ID NO: 19, and SEQ ID NO: 21; and
- d. Heavy chain CDR3 amino acid sequences: SEQ ID NO: 24, SEQ ID NO: 27, SEQ ID NO: 30, SEQ ID NO: 33, and SEQ ID NO: 36.

In a further embodiment, the GCGR antibody provided herein comprises one, two, three, or four amino acid sequences, wherein each amino acid sequence is independently selected from the amino acid sequences listed below:
- a. Light chain CDR2 amino acid sequences: SEQ ID NO: 2, SEQ ID NO: 5, SEQ ID NO: 8, SEQ ID NO: 11, and SEQ ID NO: 14;
- b. Heavy chain CDR2 amino acid sequences: SEQ ID NO: 23, SEQ ID NO: 26, SEQ ID NO: 29, SEQ ID NO: 32, and SEQ ID NO: 35;
- c. Light chain CDR3 amino acid sequences: SEQ ID NO: 3, SEQ ID NO: 6, SEQ ID NO: 9, SEQ ID NO: 12, and SEQ ID NO: 15, SEQ ID NO: 17, SEQ ID NO: 19, and SEQ ID NO: 21; and
- d. Heavy chain CDR3 amino acid sequences: SEQ ID NO: 24, SEQ ID NO: 27, SEQ ID NO: 30, SEQ ID NO: 33, and SEQ ID NO: 36.

In one embodiment, the GCGR antibody provided herein comprises one, two, or three amino acid sequences, wherein each amino acid sequence is independently selected from the amino acid sequences listed below: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21.

In another embodiment, the GCGR antibody provided herein comprises one, two, or three amino acid sequences, wherein each amino acid sequence is independently selected from the amino acid sequences listed below: SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36.

In one embodiment, the GCGR antibody provided herein comprises a combination of light and heavy chain CDR1 amino acid sequences independently selected from the list below: SEQ ID NO: 1 and SEQ ID NO: 22, SEQ ID NO: 4 and SEQ ID NO: 25, SEQ ID NO: 7 and SEQ ID NO: 28, SEQ ID NO: 10 and SEQ ID NO: 31, SEQ ID NO: 13 and SEQ ID NO: 34, SEQ ID NO: 16 and SEQ ID NO: 34, SEQ ID NO: 18 and SEQ ID NO: 34, and SEQ ID NO: 20 and SEQ ID NO: 34.

In another embodiment, the GCGR antibody provided herein comprises a combination of light and heavy chain CDR2 amino acid sequences independently selected from the list below: SEQ ID NO: 2 and SEQ ID NO: 23, SEQ ID NO: 5 and SEQ ID NO: 26, SEQ ID NO: 8 and SEQ ID NO: 29, SEQ ID NO: 11 and SEQ ID NO: 32, and SEQ ID NO: 14 and SEQ ID NO: 35.

In further embodiments, the GCGR antibody provided herein comprises a combination of light and heavy chain CDR3 amino acid sequences independently selected from the list below: SEQ ID NO: 3 and SEQ ID NO: 24, SEQ ID NO: 6 and SEQ ID NO: 27, SEQ ID NO: 9 and SEQ ID NO: 30, SEQ ID NO: 12 and SEQ ID NO: 33, SEQ ID NO: 15 and SEQ ID NO: 36, SEQ ID NO: 17 and SEQ ID NO: 36, SEQ ID NO: 19 and SEQ ID NO: 36, and SEQ ID NO: 21 and SEQ ID NO: 36.

In one embodiment, the GCGR antibody provided herein comprises:
- a. A combination of light and heavy chain CDR1 amino acid sequences independently selected from the list below: SEQ ID NO: 1 and SEQ ID NO: 22, SEQ ID NO: 4 and SEQ ID NO: 25, SEQ ID NO: 7 and SEQ ID NO: 28, SEQ ID NO: 10 and SEQ ID NO: 31, SEQ ID NO: 13 and SEQ ID NO: 34, SEQ ID NO: 16 and SEQ ID NO: 34, SEQ ID NO: 18 and SEQ ID NO: 34, and SEQ ID NO: 20 and SEQ ID NO: 34; and
- b. A combination of light and heavy chain CDR2 amino acid sequences independently selected from the list below: SEQ ID NO: 2 and SEQ ID NO: 23, SEQ ID NO: 5 and SEQ ID NO: 26, SEQ ID NO: 8 and SEQ
ID NO: 29, SEQ ID NO: 11 and SEQ ID NO: 32, and
SEQ ID NO: 14 and SEQ ID NO: 35.

In another embodiment, the GCGR antibody provided herein comprises:
  a. A combination of light and heavy chain CDR1 amino acid sequences independently selected from the list below: SEQ ID NO: 1 and SEQ ID NO: 22, SEQ ID NO: 4 and SEQ ID NO: 25, SEQ ID NO: 7 and SEQ ID NO: 28, SEQ ID NO: 10 and SEQ ID NO: 31, SEQ ID NO: 13 and SEQ ID NO: 34, SEQ ID NO: 16 and SEQ ID NO: 34, SEQ ID NO: 18 and SEQ ID NO: 34, and SEQ ID NO: 20 and SEQ ID NO: 34; and
  b. A combination of light and heavy chain CDR3 amino acid sequences independently selected from the list below: SEQ ID NO: 3 and SEQ ID NO: 24, SEQ ID NO: 6 and SEQ ID NO: 27, SEQ ID NO: 9 and SEQ ID NO: 30, SEQ ID NO: 12 and SEQ ID NO: 33, SEQ ID NO: 15 and SEQ ID NO: 36, SEQ ID NO: 17 and SEQ ID NO: 36, SEQ ID NO: 19 and SEQ ID NO: 36, and SEQ ID NO: 21 and SEQ ID NO: 36.

In another embodiment, the GCGR antibody provided herein comprises:
  a. A combination of light and heavy chain CDR2 amino acid sequences independently selected from the list below: SEQ ID NO: 2 and SEQ ID NO: 23, SEQ ID NO: 5 and SEQ ID NO: 26, SEQ ID NO: 8 and SEQ ID NO: 29, SEQ ID NO: 11 and SEQ ID NO: 32, and SEQ ID NO: 14 and SEQ ID NO: 35; and
  b. A combination of light and heavy chain CDR3 amino acid sequences independently selected from the list below: SEQ ID NO: 3 and SEQ ID NO: 24, SEQ ID NO: 6 and SEQ ID NO: 27, SEQ ID NO: 9 and SEQ ID NO: 30, SEQ ID NO: 12 and SEQ ID NO: 33, SEQ ID NO: 15 and SEQ ID NO: 36, SEQ ID NO: 17 and SEQ ID NO: 36, SEQ ID NO: 19 and SEQ ID NO: 36, and SEQ ID NO: 21 and SEQ ID NO: 36.

In a further embodiment, the GCGR antibody provided herein comprises:
  a. A combination of light and heavy chain CDR1 amino acid sequences independently selected from the list below: SEQ ID NO: 1 and SEQ ID NO: 22, SEQ ID NO: 4 and SEQ ID NO: 25, SEQ ID NO: 7 and SEQ ID NO: 28, SEQ ID NO: 10 and SEQ ID NO: 31, SEQ ID NO: 13 and SEQ ID NO: 34, SEQ ID NO: 16 and SEQ ID NO: 34, SEQ ID NO: 18 and SEQ ID NO: 34, and SEQ ID NO: 20 and SEQ ID NO: 34;
  b. A combination of light and heavy chain CDR2 amino acid sequences independently selected from the list below: SEQ ID NO: 2 and SEQ ID NO: 23, SEQ ID NO: 5 and SEQ ID NO: 26, SEQ ID NO: 8 and SEQ ID NO: 29, SEQ ID NO: 11 and SEQ ID NO: 32, and SEQ ID NO: 14 and SEQ ID NO: 35; and
  c. A combination of light and heavy chain CDR3 amino acid sequences independently selected from the list below: SEQ ID NO: 3 and SEQ ID NO: 24, SEQ ID NO: 6 and SEQ ID NO: 27, SEQ ID NO: 9 and SEQ ID NO: 30, SEQ ID NO: 12 and SEQ ID NO: 33, SEQ ID NO: 15 and SEQ ID NO: 36, SEQ ID NO: 17 and SEQ ID NO: 36, SEQ ID NO: 19 and SEQ ID NO: 36, and SEQ ID NO: 21 and SEQ ID NO: 36.

In one embodiment, the GCGR antibody provided herein comprises:
  a. A combination of light and heavy chain CDR1, CDR2 and CDR3 amino acid sequences: SEQ ID NO: 1, SEQ ID NO: 2, SEQ ID NO: 3, SEQ ID NO: 22, SEQ ID NO: 23, and SEQ ID NO: 24;
  b. A combination of light and heavy chain CDR1, CDR2 and CDR3 amino acid sequences: SEQ ID NO: 4, SEQ ID NO: 5, SEQ ID NO: 6, SEQ ID NO: 25, SEQ ID NO: 26, and SEQ ID NO: 27;
  c. A combination of light and heavy chain CDR1, CDR2 and CDR3 amino acid sequences: SEQ ID NO: 7, SEQ ID NO: 8, SEQ ID NO: 9, SEQ ID NO: 28, SEQ ID NO: 29, and SEQ ID NO: 30;
  d. A combination of light and heavy chain CDR1, CDR2 and CDR3 amino acid sequences: SEQ ID NO: 10, SEQ ID NO: 11, SEQ ID NO: 12, SEQ ID NO: 31, SEQ ID NO: 32, and SEQ ID NO: 33;
  e. A combination of light and heavy chain CDR1, CDR2 and CDR3 amino acid sequences: SEQ ID NO: 13, SEQ ID NO: 14, SEQ ID NO: 15, SEQ ID NO: 34, SEQ ID NO: 35, and SEQ ID NO: 36;
  f. A combination of light and heavy chain CDR1, CDR2 and CDR3 amino acid sequences: SEQ ID NO: 16, SEQ ID NO: 14, SEQ ID NO: 17, SEQ ID NO: 34, SEQ ID NO: 35, and SEQ ID NO: 36;
  g. A combination of light and heavy chain CDR1, CDR2 and CDR3 amino acid sequences: SEQ ID NO: 18, SEQ ID NO: 14, SEQ ID NO: 19, SEQ ID NO: 34, SEQ ID NO: 35, and SEQ ID NO: 36; and
  h. A combination of light and heavy chain CDR1, CDR2 and CDR3 amino acid sequences: SEQ ID NO: 20, SEQ ID NO: 14, SEQ ID NO: 21, SEQ ID NO: 34, SEQ ID NO: 35, and SEQ ID NO: 36.

In one embodiment, the GCGR antibody provided herein comprises one or two amino acid sequences, wherein each amino acid sequence is independently selected from the amino acid sequences listed below:
  a. Light chain variable domain amino acid sequences: SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, and SEQ ID NO: 90; and an amino acid sequence that is at least 80%, 85%, 90% or 95% identical to any above sequence, and
  b. Heavy chain variable domain amino acid sequences: SEQ ID NO: 91, SEQ ID NO: 92, SEQ ID NO: 93, SEQ ID NO: 94, SEQ ID NO: 95, SEQ ID NO: 96, and SEQ ID NO: 97; and amino acid sequences at least 80%, at least 85%, at least 90% or at least 95% identical to any above sequence.

In another embodiment, a polynucleotide coding sequence for the GCGR antibody provided herein comprises one or two polynucleotide coding sequences, wherein each polynucleotide coding sequence is independently selected from the polynucleotide sequences listed below:
  a. Light chain variable domain polynucleotide coding sequences: SEQ ID NO: 98, SEQ ID NO: 99, SEQ ID NO: 100, and SEQ ID NO: 101, SEQ ID NO: 102, SEQ ID NO: 103, and SEQ ID NO: 104, SEQ ID NO: 105, SEQ ID NO: 106, and SEQ ID NO: 107; and polynucleotide sequences that is at least 80%, at least 85%, at least 90% or at least 95% identical to any above sequence, and
  b. Heavy chain variable domains polynucleotide coding sequences: SEQ ID NO: 108, SEQ ID NO: 109, SEQ ID NO: 110, SEQ ID NO: 111, SEQ ID NO: 112, SEQ ID NO: 113, and SEQ ID NO: 114; and polynucleotide sequences that is at least 80%, at least 85%, at least 90% or at least 95% identical to any above sequence.

In one embodiment, the GCGR antibodies provided herein comprises an amino acid sequence independently selected from the list below: SEQ ID NO: 81, SEQ ID NO:

82, SEQ ID NO: 83, SEQ ID NO: 84, SEQ ID NO: 85, SEQ ID NO: 86, SEQ ID NO: 87, SEQ ID NO: 88, SEQ ID NO: 89, and SEQ ID NO: 90.

In another embodiment, the GCGR antibodies provided herein comprises an amino acid sequence independently selected from the list below: SEQ ID NO: 91, SEQ ID NO: 92, SEQ ID NO: 93, SEQ ID NO: 94, SEQ ID NO: 95, SEQ ID NO: 96, and SEQ ID NO: 97.

In one embodiment, the GCGR antibodies provided herein comprises a combination of amino acid sequences independently selected from the of light and heavy chain variable domain amino acid sequences listed below: SEQ ID NO: 81 and SEQ ID NO: 91, SEQ ID NO: 82 and SEQ ID NO: 92, SEQ ID NO: 83 and SEQ ID NO: 93, SEQ ID NO: 84 and SEQ ID NO: 94, SEQ ID NO: 85 and SEQ ID NO: 95, SEQ ID NO: 86 and SEQ ID NO: 96, SEQ ID NO: 87 and SEQ ID NO: 97, SEQ ID NO: 88 and SEQ ID NO: 97, SEQ ID NO: 89 and SEQ ID NO: 97, and SEQ ID NO: 90 and SEQ ID NO: 97.

In one embodiment, the GCGR antibodies provided herein comprises an amino acid sequence independently selected from the list below: SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 91, SEQ ID NO: 92, SEQ ID NO: 94, SEQ ID NO: 95, SEQ ID NO: 96, and SEQ ID NO: 97.

In another embodiment, the GCGR antibodies provided herein comprises a combination of amino acid sequences independently selected from the light and heavy chain variable domain amino acid sequences listed below: SEQ ID NO: 81 and SEQ ID NO: 91(L1H1), SEQ ID NO: 82 and SEQ ID NO: 92(L2H2), SEQ ID NO: 84 and SEQ ID NO: 94(L4H4), SEQ ID NO: 85 and SEQ ID NO: 95(L5H5), SEQ ID NO: 86 and SEQ ID NO: 96(L6H6), SEQ ID NO: 87 and SEQ ID NO: 97(L7H7), SEQ ID NO: 88 and SEQ ID NO: 97(L8H7), and SEQ ID NO: 89 and SEQ ID NO: 97(L9H7).

The symbol "LxHy" can also be used herein to refer to the GCGR antibody provided herein, wherein "x" corresponds to the light chain variable region sequence code and "y" corresponds to the heavy chain variable region sequence code. For example, L2H2 is a complete antibody with a light chain variable region comprising the amino acid sequence of SEQ ID NO: 82 (L2) and a heavy chain variable region comprising the amino acid sequence of SEQ ID NO: 92 (H2).

In one embodiment, the GCGR antibody provided herein comprises one or two amino acid sequences, wherein each amino acid sequence is independently selected from the amino acid sequence listed below:
 a. Light chain constant amino acid sequences: SEQ ID NO: 115 and SEQ ID NO: 116; and
 b. Heavy chain constant amino acid sequences: SEQ ID NO: 117 and SEQ ID NO: 118.

In one embodiment, the GCGR antibody provided herein comprises one or two amino acid sequences, wherein each amino acid sequence is independently selected from the amino acid sequences listed below:
 a. Light chain constant region amino acid sequence: SEQ ID NO: 115, SEQ ID NO: 116, SEQ ID NO: 132, and SEQ ID NO: 133; and
 b. Heavy chain constant region amino acid sequence: SEQ ID NO: 117 and SEQ ID NO: 118.

In one embodiment, the GCGR antibody provided herein comprises one or two amino acid sequences, wherein each amino acid sequence is independently selected from a combination of light chain and heavy chain constant amino acid sequences listed below: SEQ ID NO: 115 and SEQ ID NO: 117, SEQ ID NO: 115 and SEQ ID NO: 118, SEQ ID NO: 116 and SEQ ID NO: 117, and SEQ ID NO: 116 and SEQ ID NO: 118.

In another embodiment, the GCGR antibody provided herein comprises one or two amino acid sequences, wherein each amino acid sequence is independently selected from a combination of light chain and heavy chain constant amino acid sequences listed below: SEQ ID NO: 115 and SEQ ID NO: 117, SEQ ID NO: 115 and SEQ ID NO: 118, SEQ ID NO: 116 and SEQ ID NO: 117, SEQ ID NO: 116 and SEQ ID NO: 118, SEQ ID NO: 132 and SEQ ID NO: 117, SEQ ID NO: 132 and SEQ ID NO: 118, SEQ ID NO: 133 and SEQ ID NO: 117, and SEQ ID NO: 133 and SEQ ID NO: 118.

In one embodiment, the GCGR antibodies provided herein comprise the light and heavy chain CDRs listed herein, and the amino acid sequences of the FRs (framework). The amino acid sequences of FRs are contained in the light chain or the heavy chain variable domain and are not separately displayed. In one embodiment, the antibody comprises a light chain CDR1 sequence listed herein. In another embodiment, the antibody comprises a light chain CDR2 sequence listed herein. In another embodiment, the antibody comprises a light chain CDR3 sequence listed herein. In another embodiment, the antibody comprises a heavy chain CDR1 sequence listed herein. In another embodiment, the antibody comprises a heavy chain CDR2 sequence listed herein. In another embodiment, the antibody comprises a heavy chain CDR3 sequence listed herein. In another embodiment, the antibody comprises a light chain FR1 sequence herein. In another embodiment, the antibody comprises a light chain FR2 sequence herein. In another embodiment, the antibody comprises a light chain FR3 sequence herein. In another embodiment, the antibody comprises a light chain FR4 sequence herein. In another embodiment, the antibody comprises a heavy chain FR1 sequence herein. In another embodiment, the antibody comprises a heavy chain FR2 sequence herein. In another embodiment, the antibody comprises a heavy chain FR3 sequence herein. In a further embodiment, the antibody comprises a heavy chain FR4 sequence herein.

In one embodiment, a light chain CDR3 sequence of the antibody differs from SEQ ID NO: 12, SEQ ID NO: 15, SEQ ID NO: 17, SEQ ID NO: 19, and SEQ ID NO: 21 of the light chain CDR3 sequences illustrated above by no more than six, five, four, three, two, or one amino acid addition(s), substitution(s), and/or deletion(s). In another embodiment, a heavy chain CDR3 sequence of the antibody differs from SEQ ID NO: 33 or SEQ ID NO: 36 of the heavy chain CDR3 sequences illustrated above by no more than six, five, four, three, two or one amino acid addition(s), substitution(s), and/or deletion(s). In a further embodiment, a light chain CDR3 sequence of the antibody differs from SEQ ID NO: 12, SEQ ID NO: 15, SEQ ID NO: 17, SEQ ID NO: 19, and SEQ ID NO: 21 of the light chain CDR3 sequences illustrated above by no more than six, five, four, three, two or one amino acid addition(s), substitution(s), and/or deletion(s), in addition, and a heavy chain CDR3 sequence of the antibody differs from SEQ ID NO: 33 or SEQ ID NO: 36 of the heavy chain CDR3 sequences illustrated above by no more than six, five, four, three, two, or one amino acid addition(s), substitution(s), and/or deletion(s). In another embodiment, the antibody further comprises a combination of one, two, three, four, five, or six of light and heavy chain CDR sequences illustrated above.

In one embodiment, the GCGR antibody provided herein comprises a light chain variable domain amino acid sequence selected from L1 (SEQ ID NO: 81), L2 (SEQ ID NO: 82), L4 (SEQ ID NO: 84), L5 (SEQ ID NO: 85), L6 (SEQ ID NO: 86), L7 (SEQ ID NO: 87), L8 (SEQ ID NO: 88), and L9 (SEQ ID NO: 89) light chain variable domain sequences listed herein. In one embodiment, the amino acid sequence of the light chain variable domain of the GCGR antibody differs from the amino acid sequence of one light chain variable domain of L1 (SEQ ID NO: 81), L2 (SEQ ID NO: 82), L4 (SEQ ID NO: 84), L5 (SEQ ID NO: 85), L6 (SEQ ID NO: 86), L7 (SEQ ID NO: 87), L8 (SEQ ID NO: 88), and L9 (SEQ ID NO: 89) by fifteen, fourteen, thirteen, twelve, eleven, ten, nine, eight, seven, six, five, four, three, two or one amino acid difference, wherein the difference in each sequence is independently a deletion, insertion, and/or substitution of an amino acid residue. In another embodiment, the light chain variable domain of the GCGR antibody comprises an amino acid sequence at least 70%, at least 75%, at least 80%, at least 85%, at least 90%, at least 95%, at least 97%, or at least 99% identical to the amino acid sequence of one light chain variable domain of L1 (SEQ ID NO: 81), L2 (SEQ ID NO: 82), L4 (SEQ ID NO: 84), L5 (SEQ ID NO: 85), L6 (SEQ ID NO: 86), L7 (SEQ ID NO: 87), L8 (SEQ ID NO: 88), and L9 (SEQ ID NO: 89). In another embodiment, the polynucleotide coding sequence of the light chain variable domain of the GCGR antibody comprises a nucleotide coding sequence at least 70%, at least 75%, at least 80%, at least 85%, at least 90%, at least 95%, at least 97% or at least 99% identical to one of the polynucleotide coding sequence of L1 (SEQ ID NO: 81), L2 (SEQ ID NO: 82), L4 (SEQ ID NO: 84), L5 (SEQ ID NO: 85), L6 (SEQ ID NO: 86), L7 (SEQ ID NO: 87), L8 (SEQ ID NO: 88), and L9 (SEQ ID NO: 89). In another embodiment, the polynucleotide coding sequence of the light chain variable domain of that GCGR antibody comprises polynucleotide sequences hybridized under moderate conditions with one complementary polynucleotide coding sequences of L1 (SEQ ID NO: 81), L2 (SEQ ID NO: 82), L4 (SEQ ID NO: 84), L5 (SEQ ID NO: 85), L6 (SEQ ID NO: 86), L7 (SEQ ID NO: 87), L8 (SEQ ID NO: 88), and L9 (SEQ ID NO: 89). In a further embodiment, the polynucleotide coding sequence of the light chain variable domain of the GCGR antibody comprises a polynucleotide sequence hybridized under stringent conditions with a complementary polynucleotide coding sequence of one light chain variable domain of L1 (SEQ ID NO: 81), L2 (SEQ ID NO: 82), L4 (SEQ ID NO: 84), L5 (SEQ ID NO: 85), L6 (SEQ ID NO: 86), L7 (SEQ ID NO: 87), L8 (SEQ ID NO: 88), and L9 (SEQ ID NO: 89).

In one embodiment, the GCGR antibodies provided herein comprises a heavy chain variable domain amino acid sequence selected from H1 (SEQ ID NO: 91), H2 (SEQ ID NO: 92), H4 (SEQ ID NO: 94), H5 (SEQ ID NO: 95), H6 (SEQ ID NO: 96), and H7 (SEQ ID NO: 97) heavy chain variable domain sequences listed herein. In another embodiment, the heavy chain variable domain amino acid sequence of the antibody differs from one heavy chain variable domain sequence of H1 (SEQ ID NO: 91), H2 (SEQ ID NO: 92), H4 (SEQ ID NO: 94), H5 (SEQ ID NO: 95), H6 (SEQ ID NO: 96) and H7(SEQ ID NO: 97) by fifteen, fourteen, thirteen, twelve, eleven, ten, nine, eight, seven, six, five, four, three, two or one amino acid, wherein the difference in each sequence is independently a deletion, insertion or substitution of one amino acid residue. In another embodiment, the heavy chain variable domain of the GCGR antibody comprises an amino acid sequence at least 70%, at least 75%, at least 80%, at least 85%, at least 90%, at least 95%, at least 97%, or at least 99% identical to one heavy chain sequence of H1 (SEQ ID NO: 91), H2 (SEQ ID NO: 92), H4 (SEQ ID NO: 94), H5 (SEQ ID NO: 95), H6 (SEQ ID NO: 96), and H7 (SEQ ID NO: 97). In another embodiment, the heavy chain variable domain of the GCGR antibody comprises a polynucleotide coding sequence at least 70%, at least 75%, at least 80%, at least 85%, at least 90%, at least 95%, at least 97% or at least 99% identical to one heavy chain variable domain polynucleotide coding sequence of H1 (SEQ ID NO: 91), H2 (SEQ ID NO: 92), H4 (SEQ ID NO: 94), H5 (SEQ ID NO: 95), H6 (SEQ ID NO: 96), and H7(SEQ ID NO: 97). In another embodiment, the polynucleotide coding sequence of the GCGR antibody heavy chain variable domain comprises a polynucleotide hybridized under moderate conditions with a complementary polynucleotide coding sequence of one heavy chain variable domains of H1 (SEQ ID NO: 91), H2 (SEQ ID NO: 92), H4 (SEQ ID NO: 94), H5 (SEQ ID NO: 95), H6 (SEQ ID NO: 96), and H7(SEQ ID NO: 97). In a further embodiment, the polynucleotide coding sequence of the GCGR antibody heavy chain variable domain comprises a polynucleotide hybridized under stringent conditions with complementary polynucleotide coding sequences of one heavy chain variable domain of H1 (SEQ ID NO: 91), H2 (SEQ ID NO: 92), H4 (SEQ ID NO: 94), H5 (SEQ ID NO: 95), H6 (SEQ ID NO: 96), and H7(SEQ ID NO: 97).

In an embodiment, the antibody provided herein is an antibody comprising a combination of L1H1(SEQ ID NO: 81 and SEQ ID NO: 91), L2H2(SEQ ID NO: 82 and SEQ ID NO: 92), L3H3(SEQ ID NO: 83 and SEQ ID NO: 93), L4H4(SEQ ID NO: 84 and SEQ ID NO: 94), L5H5(SEQ ID NO: 85 and SEQ ID NO: 95), L6H6(SEQ ID NO: 86 and SEQ ID NO: 96), L7H7(SEQ ID NO: 87 and SEQ ID NO: 97), L8H7(SEQ ID NO: 88 and SEQ ID NO: 97), L9H7 (SEQ ID NO: 89 and SEQ ID NO: 97) or L10H7(SEQ ID NO: 90 and SEQ ID NO: 97), or of a desired phenotype (for example, IgA, IgG1, IgG2a, IgG2b, IgG3, IgM, IgE, or IgD), or a Fab or F(ab')2 fragment thereof.

In an embodiment, the antibody provided herein is an antibody comprising a combination of L1H1(SEQ ID NO: 81 and SEQ ID NO: 91), L2H2(SEQ ID NO: 82 and SEQ ID NO: 92), L4H4(SEQ ID NO: 84 and SEQ ID NO: 94), L5H5(SEQ ID NO: 85 and SEQ ID NO: 95), L6H6(SEQ ID NO: 86 and SEQ ID NO: 96), L7H7(SEQ ID NO: 87 and SEQ ID NO: 97), L8H6(SEQ ID NO: 88 and SEQ ID NO: 97) or L9H7(SEQ ID NO: 89 and SEQ ID NO: 97), or of a desired phenotype (for example, IgA, IgG1, IgG2a, IgG2b, IgG3, IgM, IgE, or IgD), or a Fab or F(ab')2 fragment thereof.

The antibodies provided herein can comprise any of the known constant regions of the field. The light chain constant region can be, for example, κ or λ light chain constant region, such as a mouse κ or λ light chain constant region. The heavy chain constant region can be, for example, an α, δ, ε, γ, or μ heavy chain constant region, such as the mouse α, δ, ε, γ, or μ heavy chain constant region. In an embodiment, the light or heavy chain constant region is a fragment, derivative, variant, or mutant of the natural constant region.

In an embodiment, the antibody provided herein further comprises a human light chain κ or λ constant domain or fragment thereof. The amino acid sequence of the light chain constant region is as follows:

Human κ light chain constant domain amino acid sequence: (SEQ ID NO: 115); and

Human λ light chain constant domain amino acid sequence: (SEQ ID NO: 116).

In one embodiment, the antibodies provided herein further comprise a human light chain constant domain or fragment thereof.

The amino acid sequence of the heavy chain constant region is as follows:

Human κ light chain constant region amino acid sequence: (SEQ ID NO: 132); and

Human λ light chain constant region amino acid sequence: (SEQ ID NO: 133).

In one embodiment, the antibody provided herein further comprises a constant domain of heavy chain, or a fragment thereof. The heavy chain constant region amino acid sequences are provided as follows:

Human heavy chain constant domain (IgG2) amino acid sequence: (SEQ ID NO: 117), and Human heavy chain constant domain (IgG4) amino acid sequence (SEQ ID NO: 118).

In one embodiment, the GCGR antibodies provided herein are selected from mouse-derived antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, quadruple-chain antibodies, Fab fragments, F(ab')x fragments, structural domain antibodies, IgD antibodies, IgE antibodies, IgM antibodies, IgG1 antibodies, IgG2 antibodies, IgG3 antibodies, or IgG4 antibodies.

In one embodiment, the GCGR antibody provided herein is a GCGR monoclonal antibody.

In another embodiment, the GCGR antibody provided herein is a monoclonal antibody comprising a combination of amino acid sequences selected from the list below: SEQ ID NO: 81 and SEQ ID NO: 91, SEQ ID NO: 82 and SEQ ID NO: 92, SEQ ID NO: 83 and SEQ ID NO: 93, SEQ ID NO: 84 and SEQ ID NO: 94, SEQ ID NO: 85 and SEQ ID NO: 95, SEQ ID NO: 86 and SEQ ID NO: 96, SEQ ID NO: 87 and SEQ ID NO: 97, SEQ ID NO: 88 and SEQ ID NO: 97, SEQ ID NO: 89 and SEQ ID NO: 97, and SEQ ID NO: 90 and SEQ ID NO: 97.

In one embodiment, the GCGR antibody provided herein is a mouse GCGR antibody. In another embodiment, the GCGR antibody provided herein is a humanized GCGR antibody.

In one embodiment, the GCGR antibody provided herein reduces the human glucagon signal transduction with an $IC_{50}$ value of about 1 nM to 300 nM or about 1 nM to 150 nM.

Antibodies and Antibody Fragments

In one embodiment, the antibody provided herein is a full-length antibody (including polyclonal, monoclonal, chimeric, humanized, or human antibody with full length heavy and/or light chains). In another embodiment, the antibody provided herein is an antibody fragment, for example, F(ab')2, Fab, Fab', Fv, Fc, or Fd fragment, and can be incorporated into single domain antibodies, single-chain antibodies, maxibodies, minibodies, intrabodies, double-chain antibodies, triple-chain antibodies, tetra-chain antibodies, v-NAR and bis-scFv (see e.g., Hollinger and Hudson, 2005, *Nature Biotechnology*, 23:1126-1136). In another embodiment, the antibody provided herein also includes antibody polypeptides such as those disclosed in U.S. Pat. No. 6,703,199, including fibronectin polypeptide monobodies. In another embodiment, the antibody provided herein also includes other antibody polypeptides disclosed in U. S. Patent Publication 2005/0238646, which are single-chain polypeptides.

In one embodiment, the variable regions of the IgG gene expressing a monoclonal antibody of interest in a hybridoma are amplified using nucleotide primers. These primers can be synthesized by one of ordinary skill in the art, or can be purchased from commercially available vendors, which synthesizes primers for mouse and human variable regions including, among others, primers for $V_{Ha}$, $V_{Hb}$, $V_{Hc}$, $V_{Hd}$, $C_{H1}$, $V_L$ and $C_L$ regions. These primers can be used to amplify heavy or light chain variable regions, which can then be inserted into vectors such as IMMUNOZAP™H or IMMUNOZAP™L (Stratagene), respectively. These vectors can then be introduced into *E. coli*, yeast, or mammalian-based systems for expression. Large amounts of a single-chain protein containing a fusion of the $V_H$ and $V_L$ regions can be produced using these methods (see Bird et al., 1988, *Science* 242:423-426).

It should be understood by one skilled in the art that certain proteins, such as antibodies, can undergo a variety of post-translational modifications. The types and extents of these modifications often depend on the host cell lines used to express the protein as well as the culture conditions. Such modifications can include variations in glycosylation, methionine oxidation, diketopiperizine formation, aspartate isomerization and asparagine deamidation. A frequent modification is the loss of a carboxyl-terminal basic residue (such as lysine or arginine) due to the action of carboxypeptidases (as described in Harris, 1995, *Journal of Chromatography* 705:129-134).

A common method for production of a murine monoclonal antibody is by hybridoma cells. Monoclonal antibodies can be isolated and purified by a variety of well-established techniques. Such isolation techniques include affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). A monoclonal antibody can be purified by affinity chromatography using an appropriate ligand selected based on particular properties of the antibody (e.g., heavy or light chain isotype, binding specificity, etc.). Examples of suitable ligands immobilized on a solid support include Protein A, Protein G, an anti-constant region (light chain or heavy chain) antibody, an anti-idiotype antibody, and a TGF-β binding protein, or a fragment or variant thereof.

Molecular evolution of the complementarity determining regions (CDRs) in the center of the antibody binding site also has been used to isolate antibodies with increased affinities, for example, antibodies having increased affinities for c-erbB-2, as described by Schier et al., 1996, *J. Mol. Biol.* 263:551-567. Accordingly, such techniques are useful in preparing antibodies of human GCGR.

Antibodies against human GCGR can be used, for example, in assays to detect the presence of GCGR, either in vitro or in vivo.

Antibodies can also be prepared by any of the conventional techniques. For example, they can be purified from cells that naturally express them (e.g., an antibody can be purified from a hybridoma that produces it) or produced in recombinant expression systems using any technique known in the art. See, for example, Monoclonal Antibodies, Hybridomas: A New Dimension in Biological Analyses, Kennet et al. (eds), Plenum Press, New York (1980); and Antibodies: A Laboratory Manual, Harlow and Land (eds.), Cold Spring Harbor Laboratory Press, Cold Spring Harbor, NY, (1988). This is discussed in the nucleic acid section below.

Antibodies can be prepared and screened for desired properties by any known techniques. Some techniques relate to the isolation of nucleic acids encoding polypeptide chains (or portions thereof) of related antibodies (e.g., GCGR antibodies) and manipulation of nucleic acid. Nucleic acids can be fused with another relevant nucleic acid or modified by recombinant DNA techniques (e.g., induced mutations or other conventional techniques) to add, delete or replace one or more amino acid residues.

Where it is desired to improve the affinity of antibodies according to the invention containing one or more of the above-mentioned CDRs, such antibodies can be obtained by a number of affinity maturation protocols, including maintaining the CDRs (Yang et al., 1995, *J. Mol. Biol.*, 254:392-403), chain shuffling (Marks et al., 1992, *Bio/Technology*, 10:779-783), use of mutation strains of *E. coli*. (Low et al., 1996, *J. Mol. Biol.*, 250:350-368), DNA shuffling (Patten et al., 1997, *Curr. Opin. Biotechnol.*, 8:724-733), phage display (Thompson et al., 1996, *J. Mol. Biol.*, 256:7-88) and additional PCR techniques (Crameri et al., 1998, *Nature*, 391:288-291). All of these methods or affinity maturation are discussed in Vaughan et al., 1998, *Nature Biotechnology*, 16:535-539).

In one embodiment, fragments of the GCGR antibody are provided herein. Such fragments can comprise entirely antibody-derived sequences or additional sequences. Examples of antigen binding fragments include Fab, F(ab')2, single chain antibodies, diabodies, tribodies, tetrabodies, and domain antibodies. Other examples are provided in Lunde et al., 2002, *Biochem. Soc. Trans.* 30:500-06.

Single chain antibodies can be formed by linking heavy and light chain variable domain (Fv region) fragments via an amino acid bridge (short peptide linker), resulting in a single polypeptide chain. Such single-chain Fvs (scFvs) have been prepared by fusion DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, *Biomol. Eng.* 18:95-108). By combining different $V_L$ and $V_H$-comprising polypeptides, multimeric scFvs that bind to different epitopes can be formed (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544; de Graaf et al., 2002, *Methods Mol. Biol.* 178:379-87. Single chain antibodies derived from antibodies provided herein including, but not limited to, scFvs comprising the variable domain combination L1H1, are encompassed by the present invention.

Antibodies derived from an antibody can also be obtained, for example, by proteolytic hydrolysis of the antibody, for example, pepsin or papain digestion of a whole antibody according to conventional methods. By way of example, antibody fragments can be produced by enzymatic cleavage of antibodies with pepsin to provide a SS fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoffet et al., 1960, *Arch. Biochem. Biophys.* 89:230; Porter, 1959, *Biochem. J.* 73:119; Edelman et al., Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A. 1-2.10A.5. Other methods for cleaving antibodies, such as separating heavy chains to form monovalent light-heavy chain fragments (Fd), further cleaving of fragments, or other enzymatic, chemical, or genetic techniques can also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDRs. Such polynucleotides are prepared, for example, by using the polymerase chain reaction to synthesize the variable region using mRNA or antibody-producing cells as a template (see, for example, Larrick et al., 1991, Methods: A Companion to Methods in Enzymology 2:106; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression or Antibodies," in Monoclonal Antibodies: Principles and Applications, Birch et al., (eds.), page 137 (Wiley-Liss, Inc. 1995). The antibody fragment further can comprise at least one variable region domain of an antibody described herein. Thus, for example, the V region domain can be monomeric and be a $V_H$ or $V_L$ domain, which can bind to GCGR with an affinity of $1 \times 10^{-7}$ M or less as described below.

The variable region domain can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain can be covalently attached at a C-terminal amino acid to at least one other antibody domain or a fragment thereof. Thus, for example, a $V_H$ domain that is present in the variable region domain can be linked to an immunoglobulin $C_{H1}$ domain or a fragment thereof. Similarly, a $V_L$ domain can be linked to a $C_K$ domain or a fragment thereof. In this way, for example, the antibody can be a Fab fragment, wherein the antigen binding domain contains associated $V_H$ and $V_L$ domains covalently linked at their C-termini to a $C_{H1}$ and $C_\kappa$ domain, respectively. The $C_{H1}$ domain can be extended with further amino acids, for example to provide a hinge region or a portion of a hinge region domain as found in a Fab' fragment, or to provide further domains, such as antibody $C_{H2}$ and $C_{H3}$ domains.

Derivatives and Variants of Antibodies

The nucleotide sequences of L1 and H1, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, *Gene* 42:133; Bauer et al., 1985, *Gene* 37:73; Craik, 1985, *BioTechniques,* 3:12-19; Smith et al., 1981, Genetic Engineering: Principles and Methods, Plenum Press; and U.S. Pat. Nos. 4,518,584 and 4,737,462. These and other methods can be used to make, for example, derivatives of GCGR antibodies that have a desired property, for example, an increase in affinity, avidity, or specificity for an GCGR or in vivo or in vitro stability, or reduced in vivo side-effects as compared to the underivatized antibody.

Other derivatives of anti-GCGR antibodies within the scope or this invention include covalent or aggregative conjugates or anti-GCGR antibodies, or fragments thereof, with other proteins or polypeptides, such as by expression or recombinant fusion proteins comprising heterologous polypeptides fused to the N-terminus or C-terminus or an anti-GCGR antibody polypeptide. For example, the conjugated peptide can be a heterologous signal (or leader) polypeptide, e.g., the yeast alpha-factor leader or a peptide such as an epitope tag. An antibody containing fusion proteins can comprise peptides added to facilitate purification or identification of antigen binding protein (e.g., poly-His). An antibody also can be linked to the FLAG peptide as described in Hopp et al., 1988, *Bio/Technology* 6:1204, and U.S. Pat. No. 5,011,912. The FLAG peptide is highly antigenic and provides an epitope reversibly bound by a specific monoclonal antibody (mAb), enabling rapid assay and facile purification of an expressed recombinant protein. Reagents useful for preparing fusion proteins in which the FLAG peptide is fused to a given polypeptide are commercially available (Sigma, St. Louis, Mo.). In another embodiment, oligomers that contain one or more antibodies can be employed as GCGR antagonists. Oligomers can be in the form of covalently linked or non-covalently linked dimers, trimers, or higher oligomers. Oligomers comprising two or more antibodies are contemplated for use, with one example being a homodimer. Other oligomers include heterodimers, homotrimers, heterotrimers, homotetramers, heterotetramers, etc.

One embodiment is directed to oligomers comprising multiple antibodies joined via covalent or non-covalent interactions between peptide moieties fused to the antibodies. Such peptides can be peptide linkers (spacers), or peptides that have the property of promoting oligomerization. Leucine zippers and certain polypeptides derived from antibodies are among the peptides that can promote oligomerization of antibodies attached thereto, as described in more detail below.

In particular embodiments, the oligomers comprise from two to four antibodies. The antibodies of the oligomer can be in any form, such as any of the forms described above, e.g., variants or fragments. Preferably, the oligomers comprise antibodies that show GCGR binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *PNAS USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11. One embodiment provided herein is directed to a dimer comprising two fusion proteins created by fusing a GCGR binding fragment of an anti-GCGR antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-GCGR antibody can be substituted for the variable portion of an antibody heavy and/or light chain.

Alternatively, the oligomer is a fusion protein comprising multiple antibodies, with or without peptide linkers (spacer peptides). Among the suitable peptide linkers are those described in U.S. Pat. Nos. 4,751,180 and 4,935,233.

Another method for preparing oligomeric antibodies involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one method, recombinant fusion proteins comprising an anti-GCGR antibody fragment or derivative fused to a leucine zipper peptide are expressed in suitable host cells, and the soluble oligomeric anti-GCGR antibody fragments or derivatives that form are recovered from the culture supernatant.

In another embodiment, the antibody derivatives can comprise at least one of the CDRs disclosed herein. For example, one or more CDR can be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides can be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody provided herein can have at least one amino acid substitution, providing that the antibody retains binding specificity. Therefore, modifications to the antibody structures are encompassed within the scope of the invention. These can include amino acid substitutions, which may be conservative or non-conservative, that do not destroy the human GCGR binding capability of an antibody. Conservative amino acid substitutions may encompass non-naturally occurring amino acid residues, which are typically incorporated by chemical peptide synthesis rather than by synthesis in biological systems. This include peptidomimetics and other reversed or inverted forms of amino acid moieties. A conservative amino acid substitution can also involve a substitution of a native amino acid residue with a normative residue such that there is little or no effect on the polarity or charge of the amino acid residue at that position. Non-conservative substitutions can involve the exchange of a member of one class of amino acids or amino acid mimetics for a member from another class with different physical properties (e.g., size, polarity, hydrophobicity, charge).

Moreover, one skilled in the art may generate variants to be tested, which contain a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

One skilled in the art will be able to determine suitable variants of the polypeptide as set forth herein using well-known techniques. In certain embodiments, one skilled in the art may identify suitable areas of the molecule that may be changed without destroying activity by targeting regions not to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult, 1996, *Curr. Op. Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276 and Chou et al., *Biophys. J.* 26:367-384. Moreover, computer programs are currently available to assist with predicting secondary structure. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within the structure of a polypeptide or protein. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (see Holm, supra (1999), and Brenner, supra (1997)). In certain embodiments, variants of antibodies include glycosylation variants, wherein the number and/or type of glycosylation sites have been altered compared to the amino acid sequences of a parent polypeptide. In certain embodiments, variants comprise a greater or lesser number of N-linked glycosylation sites than the native protein. Alternatively, elimination of such a sequence by substitutions removes an existing N-linked carbohydrate chain. Also provided is a rearrangement of N-linked carbohydrate chains, wherein one or more N-linked glycosylation sites (typically those that are naturally occurring) are eliminated and one or more new N-linked sites are created. Additional preferred antibody variants include cysteine variants, wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human GCGR, or to increase or decrease the affinity of the antibodies to human GCGR described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically cannot substantially change the structural characteristics of the parent sequence (e.g., a replacement amino acid should not break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (Branden and Tooze, Eds., Garland Publishing, New York, NY (1991)); and Thornton et al., 1991, *Nature* 354: 105, each of which is incorporated herein by reference.

In certain embodiments, antibodies of the invention can be chemically bonded with polymers, lipids, or other moieties.

The antigen binding agents can comprise at least one of the CDRs described herein incorporated into a biocompatible framework structure. In one embodiment, the biocompatible framework structure comprises a polypeptide or portion thereof that is sufficient to form a conformationally stable structural support, or framework, or scaffold, which is able to present one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains can be used (see, e.g., Nygren and Uhlen, 1997, *Current Opinion in Structural Biology* 7:463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, light chain CDR1, CDR2 and CDR3 can have at least one amino acid substitution, provided that the antibody retains the binding specificity of the non-substituted CDR. The non-CDR portion of the antibody can be a non-protein molecule, wherein the binding agent cross-blocks the binding of an antibody disclosed herein to human GCGR and/or inhibits the activity of glucagon signaling through the receptor. The non-CDR portion of the antibody can be a non-protein molecule in which the antibody exhibits a similar binding pattern to human GCGR peptides in a competition binding assay as that exhibited by at least one of antibodies L4H4/L5H5, and/or neutralizes the activity of glucagon. The non-CDR portion of the antibody can be composed of amino acids, wherein the antibody is a recombinant binding protein or a synthetic peptide, and the recombinant binding protein cross-blocks the binding of an antibody disclosed herein to human GCGR and/or neutralizes glucagon activity in vitro or in vivo. The non-CDR portion of the antibody can be composed of amino acids, wherein the antibody is a recombinant antibody, and the recombinant antibody exhibits a similar binding pattern to human GCGR peptides in a competition binding assay as exhibited by at least one of the antibodies L4H4/L5H5, and/or neutralizes glucagon signaling.

Fusion Protein of GCGR Antibody and GLP-1

In one embodiment, provided herein is a fusion protein of GCGR antibody and GLP-1, comprising an antibody that binds specifically to GCGR, and one, two, three, four, five, six, seven, or eight GLP-1 fragments or reverse GLP-1 fragments, wherein the fusion protein connects the carboxy terminus of GLP-1 fragment to the amino terminus of the light or heavy chain of GCGR antibody through a peptide linker sequence (Linker), or connects the amino terminus of reverse GLP-1 fragment to the carboxy terminus of the light or heavy chain of GCGR antibody.

In another embodiment, provided herein is a fusion protein of GCGR antibody and GLP-1, comprising an antibody that binds specifically to GCGR, and one, two, three, four, five, six, seven, or eight GLP-1 fragments; the fusion protein connects the carboxyl end of a GLP-1 fragment with the amino end of a GCGR antibody light chain or heavy chain through a peptide linker sequence (Linker), or connects the amino terminus of a reverse GLP-1 fragment to the carboxy terminus of a GCGR antibody light chain or heavy chain.

In another embodiment, provided herein is a fusion protein of GCGR antibody and GLP-1, comprising an antibody that binds specifically to GCGR, and one, two, three, four, five, six, seven, or eight reverse GLP-1 fragments; the fusion protein connects the amino terminus of a reverse GLP-1 fragment to the carboxy terminus of a GCGR antibody light chain or heavy chain.

In another embodiment, provided herein is a fusion protein of GCGR antibody and GLP-1, comprising an antibody that binds specifically to GCGR, and one, two, three, or four GLP-1 fragments; the fusion protein connects the carboxyl end of a GLP-1 fragment with the amino end of a GCGR antibody light chain or heavy chain through a peptide linker sequence (Linker).

In another embodiment, provided herein is a fusion protein of GCGR antibody and GLP-1, comprising an antibody that binds specifically to GCGR, and one, two, three, or four reverse GLP-1 fragments; the fusion protein connects the amino terminus of a reverse GLP-1 fragment to the carboxy terminus of a GCGR antibody light chain or heavy chain.

In another embodiment, provided herein is a fusion protein of GCGR antibody and GLP-1, comprising an antibody that binds specifically to GCGR, and two GLP-1 fragments; the fusion protein connects the carboxyl end of a GLP-1 fragment with the amino end of a GCGR antibody light chain or heavy chain through a peptide linker sequence (Linker).

In another embodiment, provided herein is a fusion protein of GCGR antibody and GLP-1, comprising an antibody that specifically binds to GCGR, and two reverse GLP-1 fragments; the fusion protein connects the amino terminus of a reverse GLP-1 fragment to the carboxy terminus of a GCGR antibody light chain or heavy chain.

In another embodiment, provided herein is a GLP-1 fusion protein comprising a GCGR antibody and two GLP-1 fragments; the fusion protein connects the carboxyl end of a GLP-1 fragment with the amino end of a GCGR antibody light chain or heavy chain through a peptide linker sequence (Linker): N'-GLP-1-Linker-R-C'; or connects the carboxy terminus of a GLP-1 fragment to the amino terminus of a GCGR antibody heavy chain: N'-GLP-1-Linker-R-C'; wherein: N' represents the amino terminus of the fusion protein polypeptide chain, C' represents the carboxy terminus of the fusion protein polypeptide chain, GLP-1 represents GLP-1 fragment, R represents the amino acid sequence of a light chain or heavy chain of GCGR antibody, and Linker represents a peptide linker sequence.

In another embodiment, provided herein is a GLP-1 fusion protein comprising GCGR antibody and two reverse GLP-1 fragments; the fusion protein connects the amino terminus of a reverse GLP-1 fragment to the carboxy terminus of a GCGR antibody light chain or heavy chain: N'-R-Linker-reverse GLP-1-C'; or connects the amino terminus of a reverse GLP-1 fragment through a peptide linker sequence (Linker) to the carboxy terminus of a GCGR antibody heavy chain: N'-R-Linker-reverse GLP-1-C'; wherein: N' represents the amino terminal of the fusion protein polypeptide chain, C' represents the carboxy terminal of the fusion protein polypeptide chain, and the reverse GLP-1 represents a reverse GLP-1 fragment, R represents the amino acid sequence of the light chain or heavy chain of a GCGR antibody, and Linker represents a peptide linker sequence.

In a further embodiment, provided herein is a GLP-1 fusion protein comprising a GCGR antibody and two GLP-1 fragments; the fusion protein connects the carboxy terminus of a GLP-1 fragment through a peptide linker sequence (Linker) to the amino terminal of a GCGR antibody light chain: N'-GLP-1-Linker-R-C'; wherein: N' represents the amino terminal of the fusion protein polypeptide chain, C' represents the carboxy terminal of the fusion protein polypeptide chain, GLP-1 represents a GLP-1 fragment, R represents the amino acid sequence of a GCGR antibody light chain, and Linker represents a peptide linker sequence.

In one embodiment, in the GLP-1 fusion protein provided herein, wherein the GLP-1 fragment is independently selected from one of the following amino acid sequences: SEQ ID NO: 119, SEQ ID NO: 120, SEQ ID NO: 121, SEQ ID NO: 122, and SEQ ID NO: 123. In one embodiment, in the GLP-1 fusion protein provided herein, wherein the reverse GLP-1 fragment is independently selected from one of the following amino acid sequences: SEQ ID NO: 127, SEQ ID NO: 128, SEQ ID NO: 129, SEQ ID NO: 130, and SEQ ID NO: 131.

In one embodiment, in the GLP-1 fusion protein provided herein, wherein the peptide linker (Linker) sequence independently comprises from 1 to 200 amino acid residues, from 2 to 100 amino acid residues, from 5 to 50 amino acid residues, from 6 to 25 amino acid residues, or from 10 to 20 amino acid residues.

In another embodiment, in the GLP-1 fusion protein provided herein, wherein the peptide linker (Linker) sequence is independently selected from the following amino acid sequences: SEQ ID NO: 124, SEQ ID NO: 125, and SEQ ID NO: 126.

Nucleic Acids

In one aspect, the present invention provides isolated nucleic acid molecules that encode the antibodies provided herein. The nucleic acids comprise, for example, polynucleotides that encode all or part of an antibody or GLP-1 fusion protein, for example, one or both chains of an antibody of the invention, or a fragment, derivative, mutein, or variant thereof; polynucleotides sufficient for use as hybridization probes; PCR primers or sequencing primers for identifying, analyzing, mutating or amplifying a polynucleotide encoding a polypeptide; anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) can be isolated from B-cells of mice that have been immunized with GCGR antigen. The nucleic acid of the antibody or GLP-1 fusion protein can be isolated by conventional procedures such as polymerase chain reaction (PCR).

Nucleic acid sequences encoding the variable regions of the heavy and light chain are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antibody or GLP-1 fusion protein provided herein.

The invention further provides nucleic acids that hybridize to other nucleic acids (e.g., nucleic acids comprising a nucleotide sequence of any of A-1/A-2) under particular hybridization conditions. Methods for hybridizing nucleic acids are well-known in the art. See, e.g., Current Protocols in Molecular Biology, John Wiley & Sons, N. Y. (1989), 6. 3. 1-6. 3. 6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, NY, chapters 9 and 11; and Current Protocols in Molecular Biology, 1995, Ausubel et al., Eds., John Wiley & Sons, Inc., sections 2. 10 and 6. 3-6. 4) and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antibody) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. No matter how it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, nucleotide sequences provided herein for L1 to L10 and H1 to H7 or the GLP-1 fusion protein, or fragments, variants, or derivatives thereof, are mutated such that they encode amino acid sequences provided herein for L1 to L10 and H1 to H7 or the GLP-1 fusion proteins, comprising one or more deletions or substitutions of amino acid residues to result in sequences bearing two or more different amino acid residues. In another embodiment, the mutagenesis inserts an amino acid adjacent to one or more amino acid residues shown herein for L1 to L10 and H1 to H7 or the GLP-1 fusion protein to result in sequences with two or more different amino acid residues. Alternatively, one or more mutations can be introduced into a nucleic acid that selectively change the biological activity. (e.g., binding to GCGR) of a polypeptide that it encodes. For example, the mutation can quantitatively or qualitatively change the biological activity. Examples of quantitative changes include increasing, reducing or eliminating the activity. Examples of qualitative changes include changing the antigen specificity of the antibody or GLP-1 fusion protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a GCGR binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the vectors provided herein comprise a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors provided herein can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, *Science* 236:1237, the disclosure of each of which is incorporated by reference herein in its entirety), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see Id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram negative or gram-positive organisms, for example, *E. coli* or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, *Cytotechnology* 28:31) or CHO strain DXB-11, which is deficient in DHFR (see Urlaub et al., 1980, *Proc. Natl. Acad. Sci. USA* 77:4216-20). Additional CHO cell lines include CHO-K1 (ATCC #CCL-61), EM9 (ATCC #CRL-1861), and W20 (ATCC #CRL-1862). Additional host cells include the COS-7 line of monkey kidney cells (ATCC #CRL-1651) (see Gluzman et al., 1981, *Cell* 23:175), L cells, C127 cells, 3T3 cells (ATCC CCL-163), AM-1/D cells (described in U.S. Pat. No. 6,210,924), HeLa cells, BHK (ATCC CRL-10) cell lines, the CV1/EBNA cell line derived from the African green monkey kidney cell line CV1 (ATCC CCL-70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, NY, 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of a polypeptide, and the polypeptide recovered by conventional protein purification procedures. One such purification procedure is described in the Examples below. Polypeptides contemplated for use herein include substantially homogeneous recombinant mammalian GCGR antibody or GLP-1 fusion protein polypeptides substantially free of contaminating endogenous materials.

Activity of GCGR Antibody

The activity of GCGR antibody refers to the effect of the antibody provided herein in binding specifically to GCGR, inhibiting or blocking glucagon signaling, thereafter demonstrating a therapeutic biological effect, for example, in treating hyperglycemia, T2DM, metabolic syndrome, and dyslipidemia. The term "decreasing the biological activity of glucagon signaling" or "inhibiting or blocking a biological activity of glucagon signaling" refers to an effect of GCGR antibody or its GLP-1 fusion protein thereof in inhibiting or blocking the downstream cellular responses to glucagon by binding to GCGR in vivo. Those responses include but not limited to lowering the output of glycogen from liver, lowering the blood glucose level, as well as variation of fat metabolism. In one embodiment, a mouse antibody or humanized antibody provided herein specifically binds to human GCGR. Such antibodies comprise antagonistic or neutralizing antibodies that reduce or neutralize glucagon signaling.

In one embodiment, the $K_d$ of the antibody provided herein binding to human GCGR is ranging approximately from 0.01 nM to 1000 nM, from 0.1 nM to 500 nM, from 0.5 nM to 200 nM, from 1 nM to 200 nM, or from 10 nM to 100 nM. In another embodiment, the $K_d$ of the antibody provided herein binding to human GCGR is approximately from 1 nM to 200 nM. In another embodiment, the $K_d$ of the antibodies provided herein binding to human GCGR is approximately from 1 nM to 100 nM. In another embodiment, the $K_d$ of the antibodies provided herein binding to human GCGR is approximately 1 nM, 2 nM, 5 nM, 10 nM, 20 nM, 30 nM, 40 nM, 50 nM, 60 nM, 70 nM, 80 nM, 90 nM, or 100 nM. In another embodiment, the $K_d$ of the antibodies provided herein binding to human GCGR is approximately 100 nM, 110 nM, 120 nM, 130 nM, 140 nM, 150 nM, 160 nM, 170 nM, 180 nM, 190 nM or 200 nM.

In one embodiment, the $IC_{50}$ of the antibody provided herein in antagonizing glucagon signaling is approximately from 0.01 nM to 500 nM, from 0.1 nM to 200 nM, from 0.5 nM to 200 nM, from 1 nM to 200 nM, or from 10 nM to 100 nM. In another embodiment, the $IC_{50}$ of the antibody provided herein in antagonizing glucagon signaling is approximately from 1 nM to 200 nM. In another embodiment, the IC50 of the antibody provided herein in antagonizing glucagon signaling is approximately from 10 nM to 100 nM. In another embodiment, the IC50 of the antibody provided herein in antagonizing glucagon signaling is approximately 1 nM, 2 nM, 5 nM, 10 nM, 20 nM, 30 nM, 40 nM, 50 nM, 60 nM, 70 nM, 80 nM, 90 nM or 100 nM. In another embodiment, the IC50 of the antibody provided herein in antagonizing glucagon signaling is approximately 100 nM, 110 nM, 120 nM, 130 nM, 140 nM, 150 nM, 160 nM, 170 nM, 180 nM, 190 nM or 200 nM.

In one embodiment, the GCGR antibody provided herein specifically binds to human GCGR with one or more following properties:
   a. providing the substantially similar Kd as a reference antibody in binding to human GCGR;
   b. providing the substantially similar IC50 as a reference antibody in antagonizing GCGR activated by glucagon; and
   c. cross-competing binding with a reference antibody to human GCGR.

In one embodiment, the reference antibody comprises a combination of light chain variable domain amino acid sequence SEQ ID NO: 87 and heavy chain variable domain amino acid sequence SEQ ID NO: 97. In another embodiment, the reference antibody is monoclonal antibody L4H4, L5H5 or L7H7.

As used herein, the term "substantially similar" means comparable to, or approximately 200%, 180%, 160%, 150%, 140%, 130%, 120%, 110%, 100%, 99%, 98%, 97%, 95%, 90%, 85%, 80%, 75%, 70%, 65%, or 50% of the IC50 or Kd of a reference antibody. In one embodiment, the reference antibody is, for example, an antibody comprising a heavy chain combination SEQ ID NO: 97 and light chain SEQ ID NO: 87. In another embodiment, the reference antibody includes GCGR antibodies, L4H4, L5H5, or L7H7.

Biological Activity of the Fusion Protein of GCGR Antibody and GLP-1

The biological activity of the fusion protein of GCGR antibody and GLP-1 comprises the biological activity of GLP-1 and the activity of GCGR antibody. The activity of GCGR antibody is as described above. "The biological activity of GLP-1" refers to the biological activity of the fusion protein of GCGR antibody and GLP-1 that binds in vivo and activates GLP-1 receptor and causes cellular signaling response, and shows therapeutically effects, such as hyperglycemia, T2DM, metabolic syndrome and other related syndromes including dyslipidemia. Combining the biological activities of GLP-1 and GCGR antibodies, the GLP-1 fusion protein provided herein can be used to treat various diseases and disorders associated with GLP-1R and GCGR. The fusion protein exerts its biological effect by acting on GLP-1R and/or GCGR, so the GLP-1 fusion protein treatment provided herein can be used to treat subjects whose disease or symptom will benefit from "increasing GLP-1R signaling" or "decreasing GCGR signaling". These subjects are referred to as subjects who "need GLP-1R stimulation therapy" or "need to reduce GCGR stimulation", including hyperglycemia, T2D, metabolic syndrome and other related syndromes.

In one embodiment, the biological activity changes of the GCGR antibody or its fusion protein with GLP-1 are detected using a direct cAMP assay, quantifying the function of GCGR antibody or the GLP-1 fusion protein in inhibiting GCGR in vitro.

Pharmaceutical Compositions

In one embodiment, a pharmaceutical composition provided herein comprises a GCGR antibody provided herein and one or more pharmaceutically acceptable carriers.

In another embodiment, a pharmaceutical composition provided herein comprises a fusion protein of GCGR antibody and GLP-1 provided herein, and one or more pharmaceutically acceptable carriers.

The term "carrier" as used herein comprises a carrier, a pharmaceutical excipient, or a stabilizer that is harmless by exposing cells or mammals to it at the dosage and concentration used.

Treatment Methods

In one embodiment, provided herein is a method of treating, preventing, or ameliorating T2D, wherein comprising administration to a subject a therapeutically effective dose of the GCGR antibody provided herein or a pharmaceutical composition thereof.

In another embodiment, provided herein is a methods of treating, preventing or ameliorating T2D, wherein comprising administration to a subject a therapeutically effective dosage of a fusion protein of the GCGR antibody provided herein and GLP-1, or a pharmaceutical composition thereof.

In one embodiment, provided herein is a method of treating, preventing or ameliorating the complications of T2D, wherein comprising administration to a subject a therapeutically effective dose of GCGR antibody provided herein or a pharmaceutical composition thereof.

In another embodiment, provided herein is a methods of treating, preventing or ameliorating the complications of T2D, wherein comprising administration to a subject a therapeutically effective dose of fusion protein of GCGR antibody provided herein and GLP-1, or a pharmaceutical composition thereof.

In another embodiment, provided herein is a method of treating, preventing or ameliorating hyperglycemia, wherein comprising administration to a subject a therapeutically effective dose of GCGR antibody provided herein or a pharmaceutical composition thereof.

In another embodiment, provided herein is a method of treating, preventing or ameliorating hyperglycemia, wherein comprising administration to a subject a therapeutically effective dose of fusion protein of GCGR antibody provided herein and GLP-1, or a pharmaceutical composition thereof.

In another embodiment, provided herein is a method of treating, preventing or ameliorating metabolic syndrome, wherein comprising administration to a subject a therapeutically effective dose of GCGR antibody provided herein or a pharmaceutical composition thereof.

In another embodiment, provided herein is a method of treating, preventing or ameliorating metabolic syndrome, wherein comprising administration to a subject a therapeutically effective dose of fusion protein of GCGR antibody provided herein and GLP-1, or a pharmaceutical composition thereof.

In another embodiment, provided herein is a method of treating, preventing or ameliorating dyslipidemia, wherein comprising administration to a subject a therapeutically effective dose of GCGR antibody provided herein or a pharmaceutical composition thereof.

In a further embodiment, provided herein is a method of treating, preventing or ameliorating dyslipidemia, wherein comprising administration to a subject a therapeutically effective dose of fusion protein of GCGR antibody provided herein and GLP-1, or a pharmaceutical composition thereof.

In any of the uses provided herein, the pharmaceutical composition provided herein is for intravenous or subcutaneous injection.

In any of the uses provided herein, it further includes administrating a therapeutically effective dose of fusion protein of GLP-1R antibody provided herein and GLP-1 to the subject.

In one embodiment, provided herein is a fusion protein of GLP-1R antibody and GLP-1 comprising
  a. Light chain CDR1 amino acid sequence: SEQ ID NO: 134;
  b. Light chain CDR2 amino acid sequence: SEQ ID NO: 135;
  c. Light chain CDR3 amino acid sequence: SEQ ID NO: 136;
  d. Heavy chain CDR1 amino acid sequence: SEQ ID NO: 137;
  e. Heavy chain CDR2 amino acid sequence: SEQ ID NO: 138; and
  f. Heavy chain CDR3 amino acid sequence: SEQ ID NO: 139.

In another embodiment, the fusion protein of GLP-1R antibody provided herein and GLP-1 includes the combination of light and heavy chain variable domain amino acid sequences: SEQ ID NO: 140 and SEQ ID NO: 141.

In this invention, the term "subject" means mammals, including human, it is used interchangeably with the term "patient".

The term "treatment" compasses alleviation or prevention of at least one symptom or other aspect of a disorder, or reduction of disease severity. A GCGR antibody or fusion protein of GCGR antibody and GLP-1 provided herein needs not to provide a complete cure, or to eradicate every symptom or manifestation of a disease, to be an effective therapeutic agent. As is recognized in the pertinent field, therapeutic agents can reduce the severity of a given disease state but need not to abolish every manifestation of the disease to be effective. Similarly, a prophylactic agent needs not to prevent the onset of a condition completely in order to be effective. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antibody in an amount and for a time sufficient to induce a sustained improvement over baseline of an indicator that reflects the severity of a particular disorder.

A pharmaceutical composition of a GCGR antibody or fusion protein of GCGR antibody and GLP-1 can be administered by any suitable technique, including, but not limited to, parenterally, topically, or by inhalation. If injected, the pharmaceutical composition can be administered, for example, via an intra-articular, intravenous, intramuscular, intralesional, intraperitoneal or subcutaneous route, by bolus injection or continuous infusion. It is considered, for example, localized administration at the disease or injury site, such as transdermal administration and sustained release of an implant. Delivery by inhalation includes, for example, nasal or oral inhalation, use of a nebulizer, inhalation of an antibody in aerosol form, and the like. Other alternatives include oral preparations, including pills, syrups, or lozenges.

Advantageously, the GCGR antibodies or fusion protein of GCGR antibody provided herein, is administered in a composition comprising one or more additional components such as a physiologically acceptable carrier, excipient, or diluent. The composition additionally comprises one or more physiologically active agents as described below. In many particular embodiments, the composition comprises one, two, three, four, five, or six physiologically active agents in addition to one or more antibodies (e.g., murine antibodies or humanized antibodies) or GLP-1 fusion protein provided herein.

In one embodiment, the pharmaceutical composition comprises a murine antibody or humanized antibody or GLP-1 fusion protein provided herein together with one or more substances selected from the group consisting of a buffer suitable for the antibody at a suitable pH, an antioxidant such as ascorbic acid, a low molecular weight polypeptide (such as those having fewer than 10 amino acids), a protein, an amino acid, a carbohydrate such as dextrin, a chelating agent such as EDTA, glutathione, a stabilizer, and an excipient. In accordance with appropriate industry standards, preservatives can also be added. The composition can be formulated as a lyophilizate using appropriate excipient solutions as diluents. Suitable components are nontoxic to recipients at the dosages and concentrations employed. Further examples of components that can be employed in pharmaceutical formulations are presented in Remington's Pharmaceutical Sciences, 16th Ed. (1980) and 20th Ed. (2000). Mack Publishing Company kits for use by medical practitioners are provided, including one or more antibodies or GLP-1 fusion protein of the invention and a label or other instructions for use in treating any of the conditions discussed herein. In one embodiment, the kit includes a sterile preparation of one or more human antibodies or GLP-1 fusion proteins, which can be in the form of a composition as disclosed above and can be in one or more vials.

Dosages and the frequency of administration can vary according to such factors as the route of administration, the particular antibody or GLP-1 fusion protein employed, the nature and severity of the disease to be treated, whether the condition is acute or chronic, and the size and general condition of the subject. Appropriate dosages can be determined by procedures known in the pertinent art, e.g. in clinical trials that can involve dose escalation studies.

The antibody or GLP-1 fusion protein provided herein can be administered, for example, once or more than once, e.g., at regular intervals over a period of time. In particular embodiments, the murine antibody or humanized antibody or GLP-1 fusion protein is administered once over a period of at least a month or longer, e.g., for one, two, or three months or even indefinitely. For treating chronic conditions, long-term treatment is generally most effective. However, for treating acute conditions, administration for shorter periods, e.g., from one to six weeks, can be sufficient. In general, the humanized antibody is administered until the patient manifests a medically relevant degree of improvement over baseline for the chosen indicator or indicators.

An example of the treatment regimen provided herein includes subcutaneous injection of the antibody or GLP-1 fusion protein at an appropriate dosage once a week or longer, to treat syndromes caused by hyperglycemia, T2D, metabolic syndrome or dyslipidemia. The antibody or GLP-1 fusion protein can be administered weekly or monthly until the desired result is achieved, for example, the patient's symptoms subside. Treatment can be renewed as needed, or, alternatively, a maintenance dose can be given.

The patient's blood glucose concentration and body weight can be monitored before, during and/or after treatment with an antibody or a GLP-1 fusion protein, such as the humanized antibody or GLP-1 fusion protein, to detect any change in their pressure. For certain conditions, changes in blood glucose can vary with factors such as disease progression. The blood glucose concentration can be determined using known techniques.

Specific embodiments of the methods and compositions herein involve the use of, for example, the antibody or GLP-1 fusion protein, and one or more glucagon antagonists, two or more antibodies or GLP-1 fusion proteins provided herein, or the antibody or GLP-1 fusion proteins provided herein and one or more other glucagon antagonists. In a further embodiment, the antibody or GLP-1 fusion protein is administered alone or in combination with other agents used to treat symptoms that are painful for the patient. Examples of these agents include both protein and non-protein drugs. When multiple drugs are administered in combination, the dosage should be adjusted accordingly as is well known in the art. "Combined administration" combination therapy is not limited to simultaneous administration, but also includes treatment regimens in which the antigen and protein are administered at least once during the course of administration involving the administration of at least one other therapeutic agent to the patient.

On the other hand, provided herein is a method for preparing a medicament for treating hyperglycemia, T2D, metabolic syndrome, dyslipidemia and related disorders, which comprises a mixture of the antibody or GLP-1 fusion protein provided herein and a pharmaceutically acceptable excipient for the treatment of the related diseases of the above diseases. The pharmaceutical preparation method is as described above.

Further provided herein are compositions, kits, and methods related to antibodies or GLP-1 fusion proteins that can specifically bind to human GCGR. Nucleic acid molecules and derivatives and fragments thereof are also provided, wherein comprising polynucleotides encoding all or part of a polypeptide that binds to GCGR, for example, nucleic acids encoding all or part of a GCGR antibody, antibody fragment or antibody derivative or GLP-1 fusion protein. Further provided herein are vectors and plasmids containing such nucleic acids and cells and cell lines containing such nucleic acids and/or vectors and plasmids. Methods provided herein comprise, for example, methods for preparing, identifying, or isolating antibodies or GLP-1 fusion proteins that bind to human GCGR, a method to determine whether the antibody or GLP-1 fusion protein binds to GCGR, and a method of administering the antibody or GLP-1 fusion protein that binds to GCGR into an animal model.

The technical solutions described herein will be further understood by the following examples.

If not specified, the starting materials and equipment described herein are commercially available or commonly used in the art. The methods in the following examples, unless otherwise specified, are all conventional methods in the art.

1: Preparation of Antigen for Immunization

CHO-DHFR– cells were seeded into a 6-well plate. After 24 hours (hrs), the cells were transfected with a pTM15 plasmid containing hGCGR (human GCGR) gene (see SEQ ID NO: 77 for the nucleotide sequence, and SEQ ID NO: 73 for the amino acid sequence). The transfection was carried out by using Lipofectamine 2000 (Invitrogen) following the manufacturer's recommended protocol. 48 hrs after transfection, the medium was replaced with a complete medium containing 10 nM methotrexate (MTX). The medium was changed every 3 days. For about two weeks of culturing, the stable clones were visible. The dispersed cell colonies were detached and continually subcultured. After cells reached 50% confluence, the concentration of MTX was gradually increased up to 300 µM for pressure selection. After about 2 weeks, stably growing clones appeared. The dispersed cell colonies were detached from the plate and passaged to continue culturing until the cells reach 100% confluence. The constructed stable cell lines were analyzed by FACS using a monoclonal antibody (Life Technologies) against V5 tag to verify positive clones after pressure selection. A large amount of cell-surface hGCGR expression was detected on the selected CHO-DHFR-hGCGR cells. Finally, two high-hGCGR-expressing stable cell lines were identified by sub-cloning and further verification. These cell lines were used to produce immunogens for antibody preparation (see Example 2). In addition, in some embodiments, the fusion protein of extracellular domain of hGCGR and hIgG Fc can also be used as immunogen for antibody preparation. The preparation method is the following: subcloning fusion protein gene of hGCGR extracellular domain, hIgG2 Fc and the peptide linker into the pTM5 plasmid. Cell supernatant was generated by mass transiently expression using suspended HEK293 cells, and then the hGCGR extracellular domain fusion protein was obtained by affinity chromatography purification.

2: Preparation of Antibodies

The immunogen and aluminum hydroxide adjuvant were mixed, and BALB/c mice (6-8 weeks) was subcutaneously injected and boosted once a week. After 6-round immunization in total, blood samples were collected from the tail veins and the serum was separated by centrifugation, then the serum titer was analyzed by FACS. After the highest titers were achieved, the mice were sacrificed, and their spleen cells were harvested under aseptic conditions. SP2/0 cells in the logarithmic growth phase were collected, centrifuged, and the cell pellets were resuspended with serum-free culture medium, then centrifuged, resuspended for a second time and counted. Spleen cells and SP2/0 cells were mixed at ratio of SP2/0 cells:spleen cells≥1:1, followed by 3-round of washing-centrifugation. After the pellets from the last centrifugation were flicked, pre-warmed PEG-1500 was added dropwise, pipette-mixed, and 30 mL of the pre-warmed serum-free medium was added slowly to terminate the PEG fusion. The cell pellets were resuspended in the fusion culture medium. Spleen cells and feeder layer cells in 100 µL were plated into each well of 96-well plates. Fused hybridoma cells and feeder layer cells were co-cultured in 96-well plates with HAT (sarcine, amethopterin and thymidine) selection to remove non-fused cells. After 10 days, the supernatants of the hybridoma cells in the culture plates were collected for ELISA analysis.

3: ELISA Screening of Antibodies

CHO-DHFR-hGCGR cells over-expressing hGCGR and CHO-DHFR– blank cells were separately transferred into a 96-well plate and allowed to reach 90% confluent. The supernatant of the culture medium was removed and attached cells were washed twice with PBS, and 100% methanol was added to fix the cells at 4° C. Then 100 µL freshly made 0.6% $H_2O_2$—PBS was added, and after incubation at room temperature for 20 min, the cells were washed twice with PBS. After blocking with 1% BSA solution (dissolved in PBS), the hybridoma supernatant was added and incubated for 90 min at 4° C. After several washes, 100 µL of the secondary antibody GxM-HRP-Fc (Sigma-Aldrich) was added into each well and incubated at 37° C. for 0.5 h. After washing five times, 100 µL of TMB chromogenic substrate was and incubated at 37° C. for 15 min, and then 50 µL of 2M H2SO4 was added to terminate the reaction before reading at 450 nm. Furthermore, in certain embodiments, a fusion protein of the N-terminal extracellular domain of hGCGR and hFc is used as the coating antigen. After blocking with 1% BSA (dissolved in PBS), the supernatant of hybridoma cells was added and incubated at 4° C. for 90 min. The subsequent steps are the same as the above ELISA method to screen anti-hGCGR monoclonal antibodies. The positive control was the mouse serum after immunization; the negative control was the cell culture supernatant. After preliminary screening by ELISA, several positive hybridoma cell lines secreted anti-hGCGR antibodies were obtained. These hybridoma cell lines secreting hGCGR antibodies were selected and subcloned by limiting dilution. Finally, the supernatant of positive hybridoma cells was verified by FACS analysis (referring Example 10).

4: Cloning and Subcloning of Antibody Genes

Hybridoma cells secreting antibodies were collected. Hybridoma mRNA was extracted according to the manufacturer protocol of QIAGEN mRNA extraction kit. Then the extracted mRNA was transcribed reversely into cDNA. The reverse transcription primers were specific primers for murine light and heavy chain constant regions, specifically the heavy chain reverse transcription primer was (5'-TTTG-GRGGGAAGATGAAGAC-3'), the light chain reverse transcription primers were (5'-TTAACACTCTCCCCTGTT-GAA-3') and (5'-TTAACACTCATTCCTGTTGAA-3'). RT-PCR reaction conditions were listed as following: 25° C. for 5 min, 50° C. for 60 min, and 70° C. for 15 min. Reversely transcribed cDNA was diluted with 0.1 mM TE to 500 µL, added into the ultrafiltration centrifuge tube (Amicon Ultra-0.5) and centrifuged at 2,000 g for 10 min. The filtrate was removed, 500 µL of 0.1 mM TE were added and centrifuged at 2,000 g for 10 min. The filtrate was removed, and the preparation tube was placed in inversion to the new centrifugal tube and centrifuged at 2,000 g for 10 min to obtain the purified cDNA. Purified cDNA (10 µL) was taken as a template, followed by addition of 4 µL 5× tailing buffer (Promega), 4 µL dATP (1 mM) and 10 U terminal transferase (Promega), mixing uniformly, and incubation at 37° C. for 5 min and then at 65° C. for 5 min. The PolyA tail cDNA was used as a template and PCR was performed to amplify light and heavy chain variable region genes of antibodies. Upstream primers were all oligodT, with heavy chain downstream primers being (5'-TGGACAGG-GATCCAGAGTTCC-3') and (5'-TGGACAGGGCTCCAT-AGTTCC-3') and light chain downstream primer being (5'-ACTCGTCCTTGGTCAACGTG-3'). The PCR reaction conditions were: 95° C. for 5 min; 95° C. for 30 s, 56° C. for 30 s, 72° C. for 1 min, 40 cycles; and 72° C. for 7 min. The PCR products were connected to the PMD 18-T vector (Takara Bio) for sequencing. PCR primers were designed based on the DNA sequences of the antibodies, thus the complete light chain, heavy chain signal peptides and variable domains and mouse IgG1 constant region were ligated into expression vector pTM5.

5: Antibody Humanization and Optimization

First of all, the sequences of light and heavy chain variable regions of the mouse antibodies were used as input in a search with NCBI online antibody variable region sequence alignment tool to find the germline gene sequences of a human antibody (Ig Germline Gene sequence) homologous to the mouse antibodies variable region sequence for humanization, and the human gene sequence with highest homology excluding the CDR sequences was used as a template for CDR grafting to obtain humanized antibody variable region sequences. The humanized antibody light and heavy chain variable regions genes were synthesized and combined with the human IgG2 or IgG4 constant region sequence to obtain full-length recombinant humanized antibody sequences. The recombinant antibodies were expressed according to Example 8, and their affinities to GCGR was analyzed by FACS as described in Example 10 to select the antibody with the best affinity. The variable region sequence of the humanized antibody was engineered by site-specific mutagenesis to further improve its affinity for GCGR.

6: Subcloning of Genes of Humanized hGCGR Antibodies

The heavy and light chain variable region gene sequences of optimized humanized antibodies were synthesized by outsourcing. During the process, two restriction sites, NheI at the 5'-end and SalI at the 3'-end were introduced into heavy chain variable region sequence. The complete heavy chain variable region was ligated with a heavy chain constant region in an expression vector of pTM5. Similarly, by introducing NheI at the 5'-end and BsiwI at the 3'-end, the light chain variable region was ligated with a light chain constant region in the expression vector of pTM5.

7: Construct of the Fusion Protein of Humanized hGCGR Antibody and GLP-1

Optimized humanized antibody was fused with GLP-1 or its derivative sequences, via the N-terminus or C-terminus of the light chain to form a GLP-1 fusion protein, and the sequences of the two are connected by the peptide linker sequence (Linker) as a bridge. Nucleotide sequence of the signal peptide-GLP-1-Linker is synthesized by Genscript Biotechnology Co., Ltd. Using the synthetic gene as the template, the sequence of the part "signal peptide-GLP1-Linker" was amplified using PCR. In addition, using the nucleotide sequence of the humanized antibody as template, the sequence of the antibody of the fusion protein sequence is amplified. Then through overlapping PCR, the part "signal peptide-GLP-1-peptide linker" of the nucleic acid sequence of the fusion protein is connected with the antibody part, introducing two restriction enzyme sites NheI and NotI to both ends of the primers, and thus complete fusion protein sequence and the expression vector pTM5 are linked together.

8: Transient Expression of GCGR Antibody and GLP-1 Fusion Protein

HEK293 or CHO suspension cells ($5 \times 10^5$/mL) was inoculated into a shaker flask. After rotating at 37° C. for 24 hr, the cells density reached $1 \times 10^6$/mL and were used for transfection. Polyethylenimine (PEI) is used as a transfection reagent, and it is mixed with DNA. The mixture of PEI/DNA was added into the cell culture after 15 minutes of incubation. After receiving the mixture of PEI/DNA, the cells were continuously cultured at 37° C., 5% CO2 for 24 hr. Then tryptone was added into the cell culture as a supplement for expression. Finally, after the protein expression was completed (more than 96 hr), the cell supernatant was collected for antibody purification.

9: Purification of GCGR Antibody and GLP-1 Fusion Protein

The supernatant obtained from Example 8 was centrifuged (8000 rpm) to remove cells and cell debris, and the supernatant was filtered through a 0.22 μm filter. The clarified supernatant is used for purification. The purification process was completed through chromatograph. The supernatant first flows through the protein A/G affinity column, during which the antibody within bounded to the A/G proteins and remained in the column. The antibodies were then eluted from the chromatography column using an elution buffer with a low pH (less than or equal to 3.0). The low pH eluent was neutralized immediately with 1M Tris-HCl. The purified antibody was then dialyzed against PBS or other buffer systems.

10: FACS Analysis of GCGR Antibody

Figure 2:
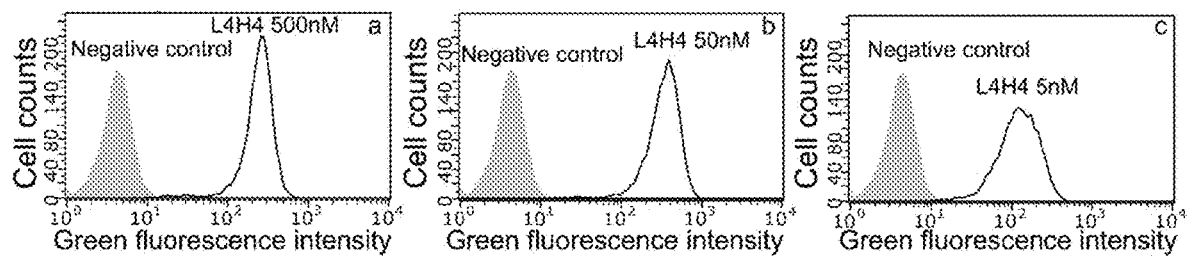
FIG. 2 shows the FACS test of the specific binding of the mouse ascites antibody L4H4 (comprising SEQ ID NO: 84 and SEQ ID NO: 94) to hGCGR, the gray peak is the negative control of 500 nM of the mouse ascites antibody L4H4 binding to the CHO-DHFR–, solid line peaks represent the binding peaks of 500 nM (2a), 50 nM (2b) or 5 nM (2c), respectively, of the mouse ascites antibody L4H4 to CHO-DHFR-hGCGR, their significant right-shift relative to the gray peak indicates that L4H4 has a specific binding to CHO-DHFR-hGCGR.

PBS containing 10 mM EDTA was used to detach the CHO-DHFR-hGCGR cells and $10^5$ cells/tube was dispensed into 1.5 mL EP tubes, and the supernatant was removed after centrifugation, The negative control sample was resuspended with a loading buffer (PBS, 2% FBS). For the positive control, 200 μL hGCGR antibody solution of specific concentrations was added to the cells and incubated at room temperature; after incubation, the cells were then centrifuged at 1500 rpm to remove the supernatant, washed with a FACS loading buffer and centrifuged again. The cells were resuspended with addition (200 μL/well) of a FITC labeled goat anti-mouse fluorescent antibody at 1:50 dilution (BD Pharmingen) and incubated at room temperature for 30 min in the dark. The supernatant was removed after centrifugation, and cells were washed with FACS loading buffer, centrifuged again, and resuspended with the loading buffer for FACS analysis. The recombinant anti-hGCGR functional antibody specifically binds to GCGR-expressing CHO-DHFR-hGCGR cells. In the experimental results shown in FIG. 1, grey peak was negative control, corresponding to 500 nM of antibody L5H5 generated from murine ascites binding to the blank cells of CHO-DHFR, the solid line peaks, corresponding to 500 nM(1a), 50 nM(1b), and 5 nM(1c) of antibody L5H5 generated by murine ascites, show a significant right-shift to prove the specific binding to the CHO-DHFR-hGCGR cells, respectively. In FIG. 2, grey peak was the negative control, corresponding to 500 nM antibody L4H4 generated by murine ascites binding to the blank cells of CHO-DHFR, the solid line peaks, corresponding to 500 nM(2a), 50 nM(2b), and 5 nM(2c) of antibody L4H5 generated by murine ascites, show a significant right-shift to prove the specific binding to the CHO-DHFR-hGCGR cells, respectively.

Figure 3:
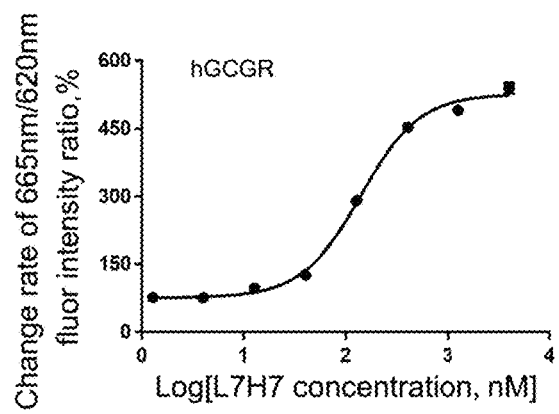
FIG. 3 shows the concentration inhibition curve of antibody L7H7 (comprising SEQ ID NO: 87 and SEQ ID NO: 97) antagonizing glucagon activation of hGCGR signaling pathway ($IC_{50}$=139 nM, $R^2$=0.99), as determined by direct cAMP assay.

11: cAMP Assay Test of hGCGR Antibody or GCGR Antibody and GLP-1 Fusion Protein for its In Vitro Antagonistic Activity of GCGR CHO-DHFR- cells stably expressing human GCGR were seeded with 30,000 cells per well into 96-well plate, placed in a 37° C., 5% $CO_2$ incubator for overnight. The next day the supernatant was removed and the hybridoma supernatant or serially diluted antibody of 45 μL per well was added. The cells were left at room temperature for 30 min, then glucagon peptide (Phoenix Pharmaceuticals, 50 pM) was added at 45 μL/well. Then the 96-well plate was placed in a 37° C., 5% $CO_2$ incubator for 30 minutes, 10 μL/well of 10% Triton X-100 were added to lyse the cells at room temperature, and lysate was mixed evenly with the pipette. The cAMP kit (CisBio) was used to detect the cAMP produced in the experiment. The above 10 μL/well cell lysate were transferred into a white 384-well plate, 5 μt/well of 1:20 diluted cAMP-d2 was added, and finally 5 μL/well of 1:20 diluted Anti-cAMP-Eu3±cryptate was added, and the plate was incubated at room temperature for 1 hr. The time-resolved fluorescence 665 nm/620 nm signal ratio was read on the Envision 2103 microplate reader, and then Prism5.0 was used to calculate the $IC_{50}$ value. FIG. 3 shows that hGCGR antibody L7H7 antagonizes GCGR activated by glucagon in a dose-dependent curve ($IC_{50}$=139 nM, $R^2$=0.99) in a direct cAMP assay.

Figure 4:
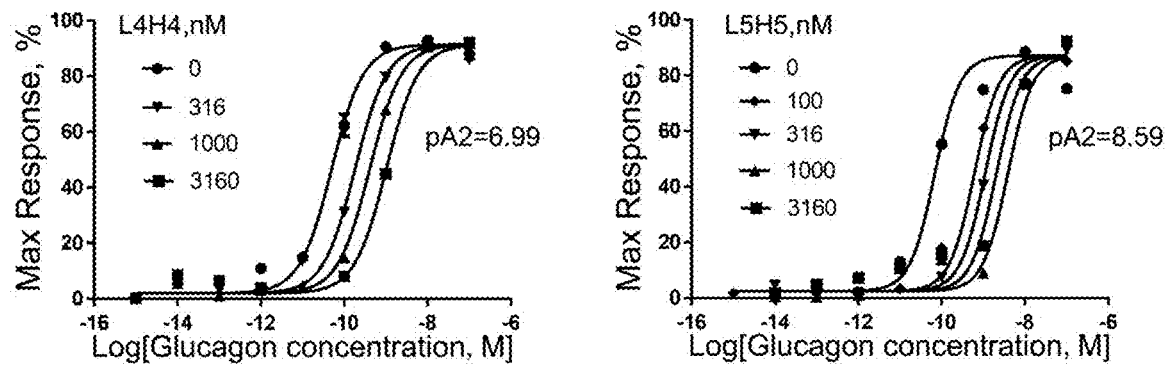
FIG. 4 shows the Schild analysis of mouse ascites GCGR antibodies (L4H4 and L5H5) antagonizing serial diluted glucagon activation of hGCGR signaling pathway. As the GCGR antibody concentration increases, the S shaped curves of hGCGR activation by glucagon show notable right-shifts.

Schild Analysis: in a direct cAMP assay described above, fix the anti-GCGR antibodies (L4H4 and L5H5) at 3160 nM, 1000 nM, 316 nM, 0 nM, serially dilute glucagon (100 nM to 1 fM), and increasing concentrations of GCGR antibody induced 2 times parallel rightward shifts of the glucagon dose-response curves, which were was termed as pA2 of the antibody using Prims 5.0 software. FIG. 4 shows the Schild analysis of direct cAMP assay to detect mouse ascites GCGR antibody, which antagonizes the activation of hGCGR signaling pathway by gradient dilution of glucagon. As the concentration of anti-GCGR antibody increases, the S-curve of glucagon activation of its receptor shifts to the right.

Figure 5:
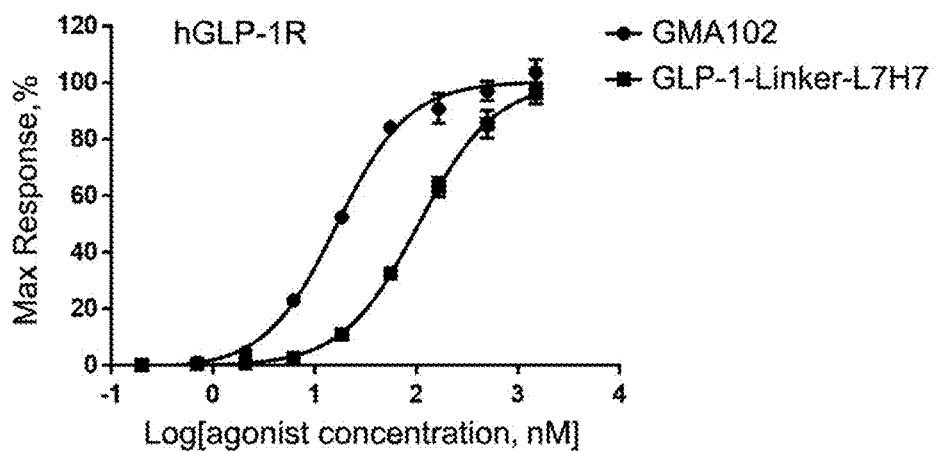
FIG. 5 shows the activation curves of hGLP-1R signaling pathway by the fusion protein of GCGR antibody with GLP-1, GLP-1-Linker-L7H7, and GMA102 ($EC_{50}$ are 106 pM 和 16 pM, respectively, $R^2$=0.99).

12: Reporter Gene Assay Test of hGCGR Antibody and GLP-1 Fusion Protein for its In Vitro Activation of GLP-1R CHO-DHFR- cells co-expressing hGLP1R and CRE-Luciferase were seeded into a 96-well cell culture plate with 40000 cells per well and cultured at 37° C. overnight. The next day the culture supernatant was removed. The cells were washed twice with serum free medium and residual liquid was removed as well. Then add 100 μL of serum free medium containing serially diluted antibodies or GMA102 and incubate at 37° C. for 4 hr. After the stimulation, 100 μL of Bright Glo chemiluminescence substrate (Promega) was added. Finally, the cell lysates were transferred into a white 96-well plate, and the relative luminous intensity was recorded in SpectraMax L microplate reader (Molecular Devices). FIG. 5 shows that GLP-1-Linker-L7H7 and GMA102 activate hGLP-1R ($EC_{50}$ was 106 pM and 16 pM respectively). Among the reagents, GMA102 is a long-acting GLP-1 agonist developed by the inventors of disclosure (Li et al., Biochem Pharmacol. 2018, 150:46-53; CN 201410349725), it can activate the cAMP signaling pathway, significantly reduce the blood glucose and body weight of mice and is under development in phase II clinical trial.

13: In Vivo Efficacy Study of GCGR Antibody L4H4 Alone or in Combination with GMA102 (Proprietary Fusion Protein of GLP-1R Antibody and GLP-1) in Normal ICR Mice Animals in each group were fasted overnight (water ad libitum), blood was collected from the tail tip, and blood glucose level was measured with a Roche superior blood glucose meter (the same below) (0 min), and then administered by subcutaneous injection (0.1 mL/10 g weight, normal control PBS, administration group: L4H4 alone use 2.5, 5, 10 mg/kg, or combined with GMA102 doses of 2.5, 5 mg/kg, respectively, GMA102 is a humanized antibody fusion protein, there are anti-drug antibodies in mice, therefore the drug is given once every two days, and the mouse-derived L4H4 is given only once), and the glucose solution of each group of animals was given intragastrically (2 g/kg, 0.1 mL/10 g body weight) 30 min after subcutaneous injection, and after the glucose load blood was collected from the tail tip at 30, 60, and 120 minutes to determine blood glucose levels. On the second day of administration, in order to reduce the irritation to the animals, only the blood glucose levels of the animals in each group were measured after 5 hours of fasting (free drinking) (0 min) and 30 min after glucose load. After that, the blood glucose level after glucose load was continuously measured for four days, six days, eight days, ten days and twelve days after administration.

After the combined injection of GMA102 and GCGR antibody L4H4, Table 3 shows that from 2nd day to 8th day, GMA102, L4H4 alone, and the combination of GMA102 and L4H4 significantly reduced the oral glucose tolerance of mice, and the combined use effect is more obvious than the single-use effect of both, and it has a synergistic effect. Expressed in AUC (mean±SD), N=6.

TABLE 3

AUC values of the OGTT blood sugar time curves, after a single dose of subcutaneous administration of L4H4, GMA102, or the combination of the two into healthy ICR mice, at different time points

| Groups | Day 1 | Day 2 | Day 4 | Day 6 | Day 8 |
|---|---|---|---|---|---|
| PBS | 1,158.3 ± 160.9 | 314.8 ± 34.8 | 842.8 ± 104.3 | 854.3 ± 104.6 | 989.0 ± 88.0 |
| L4H4 - 2.5 mg/kg | 1,109.0 ± 154.9 | 262.8 ± 33.2** | 633.3 ± 75.8** | 693.0 ± 121.2 | 907.8 ± 80.7 |
| L4H4 - 5 mg/kg | 1,145.0 ± 74.6 | 260.0 ± 39.3** | 653.0 ± 57.4** | 577.3 ± 84.3* | 630.8 ± 78.3** |
| L4H4 - 10 mg/kg | 1,109.8 ± 101.1 | 248.0 ± 31.0** | 559.3 ± 64.3** | 562.0 ± 76.3** | 579.5 ± 48.5** |
| GMA102 - 5 mg/kg | 809.5 ± 102.8** | 191.8 ± 16.8** | 612.0 ± 73.6** | 583.8 ± 110.9* | 765.0 ± 108.8* |
| L4H4 (2.5 mg/kg) + GMA102 (5 mg/kg) | 945.0 ± 88.4**##X | 195.8 ± 14.8**## | 522.3 ± 30.2**##X | 482.3 ± 26.4** | 657.3 ± 28.5**## |
| L4H4 (5 mg/kg) + GMA102 (5 mg/kg) | 950.8 ± 72.7ΔΔX | 182.0 ± 20.3ΔΔ | 540.3 ± 24.1ΔΔ | 477.5 ± 27.8 | 574.5 ± 25.9** |
| L4H4 (10 mg/kg) + GMA102 (5 mg/kg) | 883.5 ± 58.2☆☆ | 170.5 ± 19.3☆☆ | 507.8 ± 80.6X | 423.3 ± 52.3 | 554.0 ± 56.2**X |
| L4H4 (5 mg/kg) + GMA102 (2.5 mg/kg) | 900.3 ± 62.7ΔΔ | 180.3 ± 18.5ΔΔ | 518.5 ± 62.3ΔΔ | 459.8 ± 32.9 | 581.8 ± 46.6** |

Note:
vs PBS, *, P < 0.05, **, P < 0.01;
vs L4H4 - 2.5 mg/kg, #, P < 0.05, ##, P < 0.01;
vs L4H4 - 5 mg/kg, Δ, P < 0.05, ΔΔ, P < 0.01;
vs L4H4 - 10 mg/kg, ☆, P < 0.05, ☆☆, P < 0.01;
vs GMA102 - 5 mg/kg, X, P < 0.05, XX, P < 0.01.

Figure 6:
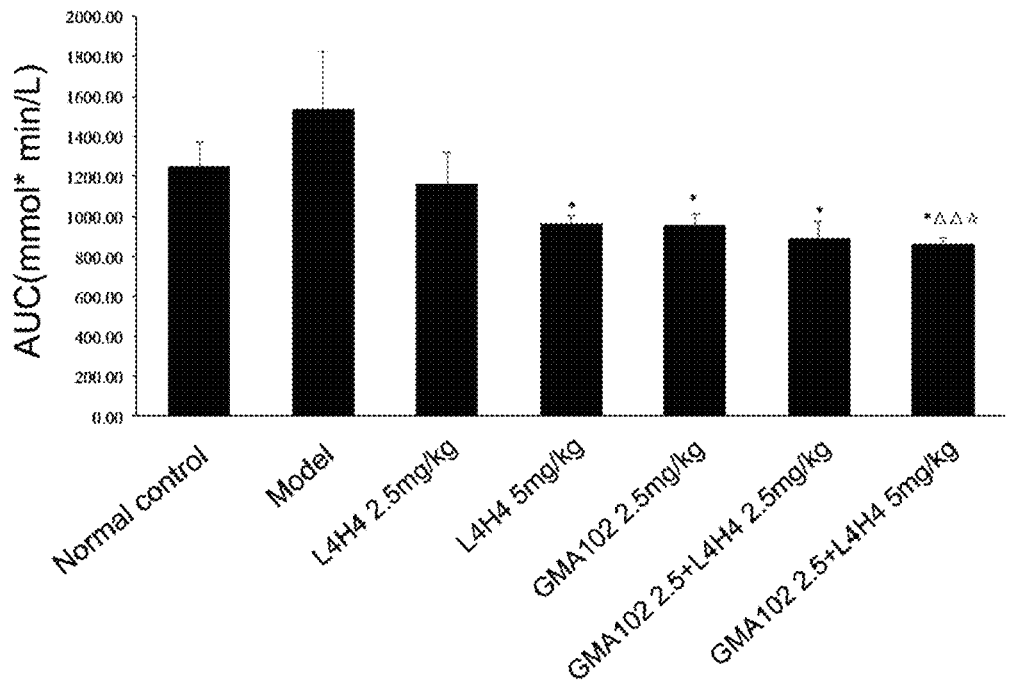
FIG. 6 show the oral glucose tolerance test results on high-fat diet induced obese C57BL/6 mice, 14 days after administrations of single subcutaneous dose of L4H4, GMA102 (given every other day), and a combination of both.

14: In vivo efficacy study of L4H4 alone or in combination with GMA102 (proprietary fusion Protein of GLP-1R Antibody and GLP-1) in High-Fat Diet-Induced C57BL/6 Obese Mice 60% high fat diet induced C57BL/6 mice obesity model (DIO mice) was established. After the mice were purchased and fed with a normal diet for a week, randomly selected a certain number of mice as the normal control group to give ordinary mice diet, and the remaining animals were fed with high-fat diet. All animals were continuously fed for 8 weeks, and the body weight and food intake were assessed once a week. Subsequently, the mice fed with high-fat diet were randomly divided based on body weight. All mice were fasted (water ad libitum) overnight and blood-sampled through tail vein puncture and blood sugar level (0 min) thereof was measured by Roche Accu-Chek blood glucose meter, after which, the animals were administrated subcutaneously with drug substances (0.1 mL per 10 g of body weight, normal control group with PBS, experimental groups with L4H4 alone at 2.5, 5 mg/kg, GMA102 alone at 2.5 mg/kg or L4H4 in combination with low or high dose of GMA102, mouse L4H4 was administrated weekly, GMA102 was administrated once every the other day). Body weight, food intake, random blood sugar level, fasting blood sugar level, OGTT and HbA1c were monitored. FIG. 6 shows that high fat induced C57BL/6 obese mice, after receiving single dose administration of L4H4, GMA102 or combination of GMA102 and L4H4, all had a reduced oral glucose tolerance, and more so in combination group than in group given single substance, indicating a synergistic effect between the two substances. Two weeks after single dose, L4H4 still retained significant blood sugar lowering effect, demonstrating its apparent long-acting effect. Note: vs PBS, *, P<0.05, **, P<0.01; vs L4H4-5 mg/kg, Δ, P<0.05, ΔΔ, P<0.01; vs GMA102-2.5 mg/kg, ☆, P<0.05, ☆☆, P<0.01.

15: Pharmacokinetic Study of the Fusion Protein of GCGR Antibody and GLP-1 in Cynomolgus Monkeys.

A total of 6 cynomolgus monkeys (3 male and 3 female) received a single subcutaneous injection of the fusion protein of GCGR antibody and GLP-1 at 2 mg/kg dose, and 0.6 mL whole blood sample was collected each at pre-administration (0 min), post-administration 2 hr, 4 hr, 8 hr, 12 hr, 24 hr, 2 d, 4 d, 6 d, 8 d, 10 d, 12 d, 18 d, 28 d via the forelimb vein at the body side same to the administration site and placed in a centrifuge tube on ice, after natural coagulation, the blood samples were then centrifuged to separate the sera and stored at a low temperature (−80° C.) until use. The GCGR antibody part and GLP-1 part of the fusion protein in the serum samples were quantified separately by ELISA, and the half-lives of both in the cynomolgus monkey was determined through software analysis.

16, Pharmacokinetic Study of the Fusion Protein of GCGR Antibody and GLP-1 on Rhesus Macaques.

2 rhesus macaques (equal number for each gender) received a single subcutaneous injection of the fusion protein of GCGR antibody and GLP-1 at 2 mg/kg dose, and 0.6 mL whole blood sample was collected each at pre-administration (0 min), post-administration 2 hr, 4 hr, 8 hr, 12 hr, 24 hr, 2 d, 4 d, 6 d, 8 d, 10 d, 12 d, 18 d, 28 d via the forelimb vein at the body side same to the administration site and placed in a centrifuge tube on ice, after natural coagulation, the blood samples were then centrifuged to separate the sera and stored at a low temperature (−80° C.) until use. The GCGR antibody part and GLP-1 part of fusion protein in the serum samples were quantified separately by ELISA, and the half-lives of both in the cynomolgus monkey was determined through software analysis.

Figure 7:
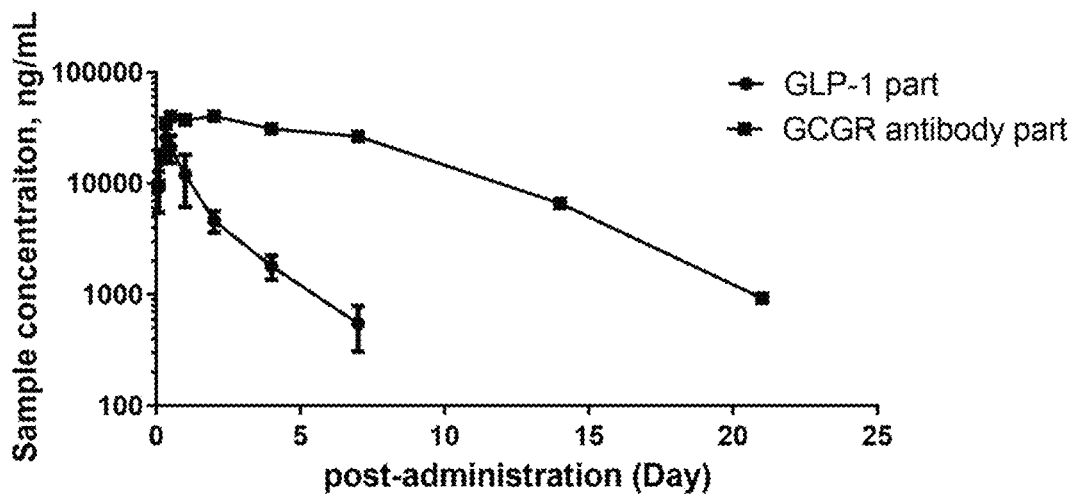
FIG. 7 shows the PK study of the fusion protein of hGCGR antibody and GLP-1, GLP-1-Linker-L7H7, in healthy rhesus macaques.

PK studies indicate that the half-life ($T_{1/2}$) of the GLP-1 part is about 38 h, while the antibody part of GLP-1-Linker-L7H7 has a half-life ($T_{1/2}$) of 131 h. The PK curves and parameters were shown in FIG. 7 and Table 4.

TABLE 4

The parameters of fusion protein of GCGR antibody and GLP-1 (GLP-1-Linker-L7H7) of the PK studies

|  |  | GLP-1 part | Antibody Part |
|---|---|---|---|
| $T_{1/2}$ | h | 38 ± 6 | 131 ± 40 |
| Tmax | h | 8 | 12 – 48 |
| Cmax | ng/mL | 25585 ± 5537 | 43743 ± 503 |

17, Intravenous Glucose Tolerance Test (IVGTT) of Single Dose Administration of the Fusion Protein of GCGR Antibody and GLP-1 on Healthy Rhesus Macaques.

4 rhesus macaques (equal number for each gender) were administrated subcutaneously with single dose of GLP-1-Linker-L7H7 and positive control GMA102 (proprietary fusion protein of GLP-1R antibody and GLP-1), the dose was 2 mg/kg. All the test subjects were fasted overnight (14-16 h) starting from the previous night, on the day of test, the test subjects were anesthetized and then infused through lower limb vein with 50% glucose solution (0.25 g/kg), at the following time points, 0.8 mL of blood samples were withdrawn from their forearm veins: 5 and 3 min pre-glucose infusion, 3, 5, 7, 10, 20 and 30 min post-glucose infusion, EDTA2K were added to prevent coagulation, the serum were extracted from the blood sample through centrifugation and used in tests of insulin and blood sugar levels.

Figure 8:
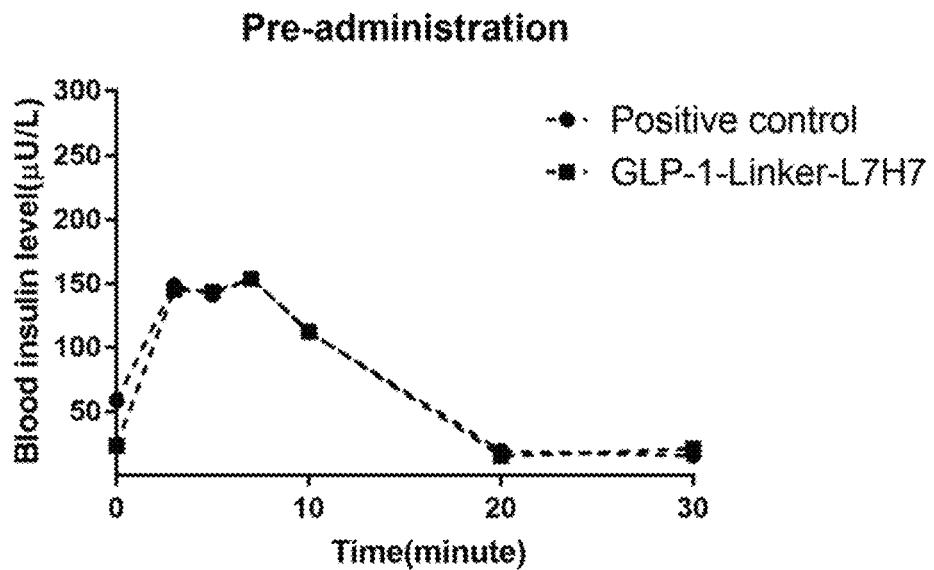
FIG. 8 shows the insulin level time curve of the healthy rhesus macaques before subcutaneous injection of single dose of positive control and the fusion protein of hGCGR antibody and GLP-1, GLP-1-Linker-L7H7, in an intravenous glucose tolerance test (IVGTT).
Figure 9:
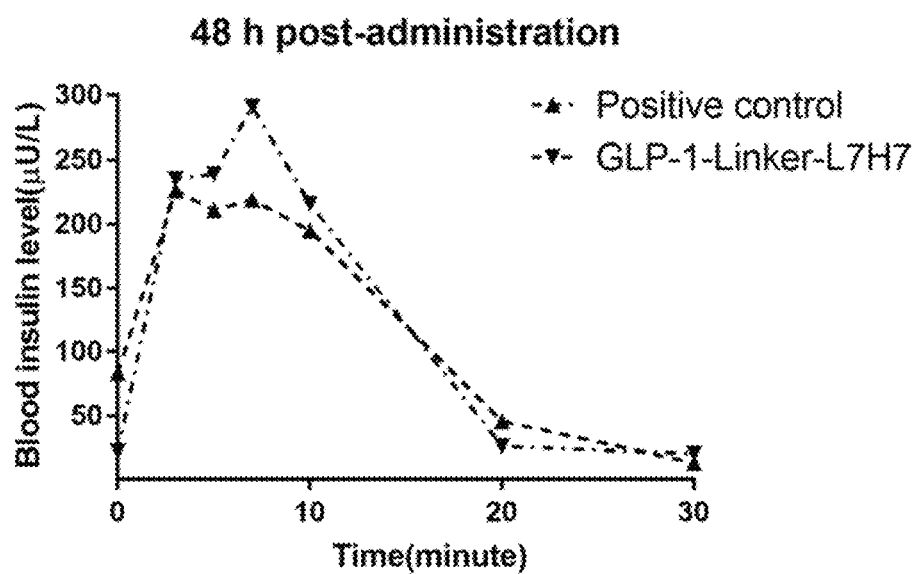
FIG. 9 shows the insulin level time curve of the healthy rhesus macaques 48 h after subcutaneous injection of single dose of positive control and fusion protein of hGCGR antibody and GLP-1, GLP-1-Linker-L7H7, in an intravenous glucose tolerance test (IVGTT).
Figure 10:
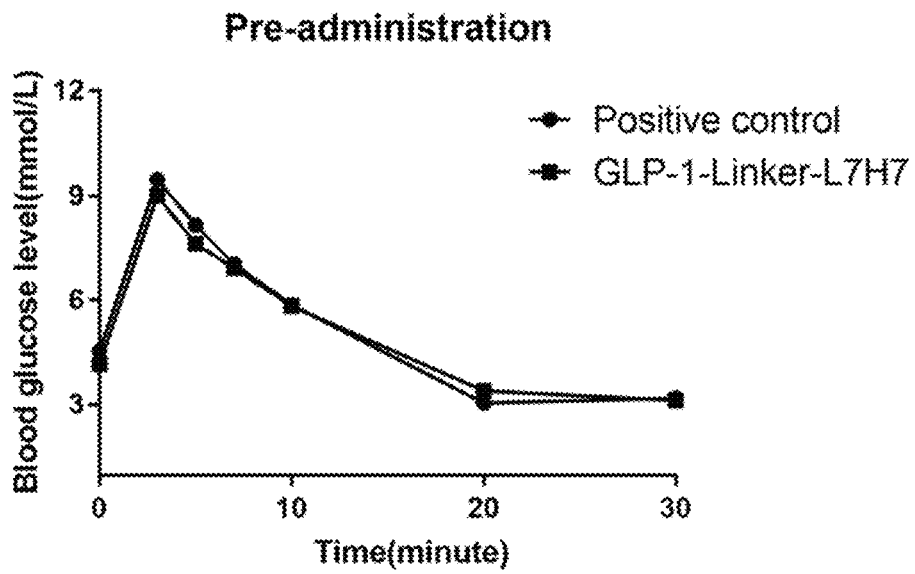
FIG. 10 shows the blood sugar level time curve of the healthy rhesus macaques before subcutaneous infusion of single dose of positive control and fusion protein of hGCGR antibody and GLP-1, GLP-1-Linker-L7H7, in an intravenous glucose tolerance test (IVGTT).
Figure 11:
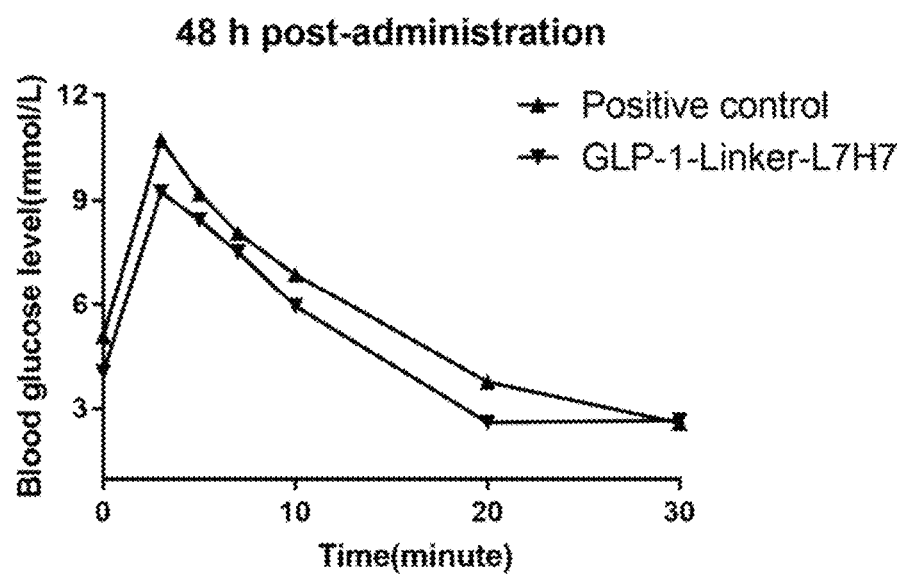
FIG. 11 shows the blood sugar level time curve of the healthy rhesus macaques 48 h after subcutaneous infusion of single dose of positive control and fusion protein of hGCGR antibody and GLP-1, GLP-1-Linker-L7H7, in an intravenous glucose tolerance test (IVGTT).

The insulin levels (μU/mL) in the blood samples were determined using Roche cobas 6000 analyzer series E601. The results were shown in FIG. 8 and FIG. 9, before administration, two groups of animals secreted equal amount of endogenous insulin, while 48 h post-administration, the group taken GLP-1-Linker-L7H7 secreted more insulin than the positive control group. The blood glucose levels (mmol/L) of the blood samples were analyzed using Roche cobas 6000 analyzer series C501, the results were shown in FIG. 10 and FIG. 11, before administration, the blood glucose levels of the two groups were substantially comparable, while 48 h post-administration, the group taken GLP-1-Linker-L7H7 had lower levels of blood glucose than the positive control group.

The above embodiments are meant to fully disclose and explain how to make and use the claimed embodiments to one of ordinary skill in the art, and they are not meant to limit the scope of this disclosure. Modifications obvious to those skilled in the art are within the scope of the claims herein. All the publications, patents and patent applications cited in the specifications were incorporated herein as references, just as each of them was specifically and independently incorporated herein as a reference.

What is claimed is:

1. An antibody specifically binding to human GCGR, wherein the antibody comprises:
    a. a light chain CDR1 amino acid sequence: SEQ ID NO: 13;
    b. a light chain CDR2 amino acid sequence: SEQ ID NO: 14;
    c. a light chain CDR3 amino acid sequence: SEQ ID NO: 15;
    d. a heavy chain CDR1 amino acid sequence: SEQ ID NO: 34;
    e. a heavy chain CDR2 amino acid sequence: SEQ ID NO: 35; and
    f. a heavy chain CDR3 amino acid sequence: SEQ ID NO: 36.

2. A GLP-1 fusion protein, comprising the antibody of claim 1, and a GLP-1 fragment or reverse GLP-1 fragment; wherein either the carboxy terminal of the GLP-1 fragment is connected with the amino terminal of a light chain or a heavy chain of the antibody via a peptide linker, or the amino terminal of the reverse GLP-1 fragment is connected with the carboxy terminal of a light chain or a heavy chain of the antibody via a peptide linker.

3. The GLP-1 fusion protein of claim 2, wherein the antibody comprises a combination of light chain and heavy chain variable domain amino acid sequences SEQ ID NO: 87 and SEQ ID NO: 97.

4. The GLP-1 fusion protein of claim 2, wherein the GLP-1 fragment comprises an amino acid sequence selected from the group consisting of: SEQ ID NO: 119, SEQ ID NO: 120, SEQ ID NO: 121, SEQ ID NO: 122, and SEQ ID NO: 123.

5. The GLP-1 fusion protein of claim 2, wherein the reverse GLP-1 fragment comprises an amino acid sequence selected from the group consisting of: SEQ ID NO: 127, SEQ ID NO: 128, SEQ ID NO: 129, SEQ ID NO: 130, and SEQ ID NO: 131.

6. The GLP-1 fusion protein of claim 2, wherein the peptide linker comprises an amino acid sequence selected from the group consisting of: SEQ ID NO: 124, SEQ ID NO: 125, and SEQ ID NO: 126.

7. The antibody of claim 1, wherein the antibody comprises a combination of light chain and heavy chain variable domain amino acid sequences SEQ ID NO: 87 and SEQ ID NO: 97.

* * * * *

SEQUENCE LISTING

```
<160> NUMBER OF SEQ ID NOS: 141

<210> SEQ ID NO 1
<211> LENGTH: 10
<212> TYPE: PRT
<213> ORGANISM: Mus musculus

<400> SEQUENCE: 1

Ser Ala Ser Ser Ser Val Ile Tyr Met Tyr
1               5                   10

<210> SEQ ID NO 2
<211> LENGTH: 7
<212> TYPE: PRT
<213> ORGANISM: Mus musculus
```

```
<400> SEQUENCE: 2

Asp Thr Ser Asn Leu Val Ser
1               5

<210> SEQ ID NO 3
<211> LENGTH: 9
<212> TYPE: PRT
<213> ORGANISM: Mus musculus

<400> SEQUENCE: 3

Gln Gln Tyr Ser Gly Tyr Pro Tyr Thr
1               5

<210> SEQ ID NO 4
<211> LENGTH: 16
<212> TYPE: PRT
<213> ORGANISM: Mus musculus

<400> SEQUENCE: 4

Lys Ser Ser Gln Arg Ile Val His Ser Asp Gly Lys Thr Tyr Leu Glu
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Ile Pro Trp Thr
1               5

<210> SEQ ID NO 7
<211> LENGTH: 15
<212> TYPE: PRT
<213> ORGANISM: Mus musculus

<400> SEQUENCE: 7

Arg Ala Ser Glu Ser Val Asp Asn Phe Gly Phe Ser Phe Met Asn
1               5                   10                  15

<210> SEQ ID NO 8
<211> LENGTH: 7
<212> TYPE: PRT
<213> ORGANISM: Mus musculus

<400> SEQUENCE: 8

Ser Ala Ser Asn Gln Gly Ser
1               5

<210> SEQ ID NO 9
<211> LENGTH: 9
<212> TYPE: PRT
<213> ORGANISM: Mus musculus

<400> SEQUENCE: 9
```

Gln Gln Ser Lys Glu Ile Pro Phe Thr
1               5

<210> SEQ ID NO 10
<211> LENGTH: 11
<212> TYPE: PRT
<213> ORGANISM: Mus musculus

<400> SEQUENCE: 10

Arg Ala Ser Gly Asn Ile His Asn Tyr Leu Thr
1               5                   10

<210> SEQ ID NO 11
<211> LENGTH: 6
<212> TYPE: PRT
<213> ORGANISM: Mus musculus

<400> SEQUENCE: 11

Asn Ala Lys Ala Leu Ala
1               5

<210> SEQ ID NO 12
<211> LENGTH: 9
<212> TYPE: PRT
<213> ORGANISM: Mus musculus

<400> SEQUENCE: 12

Leu His Phe Trp Ser Ser Pro Leu Thr
1               5

<210> SEQ ID NO 13
<211> LENGTH: 17
<212> TYPE: PRT
<213> ORGANISM: Mus musculus

<400> SEQUENCE: 13

Lys Ser Ser Gln Ser Leu Leu Tyr Ser Asn Asn Gln Lys Asn Tyr Leu
1               5                   10                  15

Ala

<210> SEQ ID NO 14
<211> LENGTH: 7
<212> TYPE: PRT
<213> ORGANISM: Mus musculus

<400> SEQUENCE: 14

Trp Ala Ser Thr Arg Glu Ser
1               5

<210> SEQ ID NO 15
<211> LENGTH: 9
<212> TYPE: PRT
<213> ORGANISM: Mus musculus

<400> SEQUENCE: 15

Gln Gln Tyr Tyr Ser Tyr Pro Leu Thr
1               5

<210> SEQ ID NO 16
<211> LENGTH: 17
<212> TYPE: PRT
<213> ORGANISM: Homo sapiens

<400> SEQUENCE: 16

```
Lys Ser Ser Gln Ser Val Leu Tyr Ser Ser Asn Asn Lys Asn Tyr Leu
1               5                   10                  15
Ala

<210> SEQ ID NO 17
<211> LENGTH: 9
<212> TYPE: PRT
<213> ORGANISM: Homo sapiens

<400> SEQUENCE: 17

Gln Gln Ser Tyr Ser Thr Pro Leu Thr
1               5

<210> SEQ ID NO 18
<211> LENGTH: 17
<212> TYPE: PRT
<213> ORGANISM: Homo sapiens

<400> SEQUENCE: 18

Lys Ser Ser Gln Ser Val Leu Tyr Thr Ser Asn Asn Asn Asn Tyr Leu
1               5                   10                  15
Ala

<210> SEQ ID NO 19
<211> LENGTH: 9
<212> TYPE: PRT
<213> ORGANISM: Homo sapiens

<400> SEQUENCE: 19

Gln Gln Tyr Phe Ser Thr Pro Ile Thr
1               5

<210> SEQ ID NO 20
<211> LENGTH: 17
<212> TYPE: PRT
<213> ORGANISM: Homo sapiens

<400> SEQUENCE: 20

Lys Ser Ser Gln Ser Val Leu Tyr Asn Pro Asn Ser Lys Asn Tyr Phe
1               5                   10                  15
Ala

<210> SEQ ID NO 21
<211> LENGTH: 9
<212> TYPE: PRT
<213> ORGANISM: Homo sapiens

<400> SEQUENCE: 21

Gln Gln Tyr Tyr Ile Thr Pro Tyr Thr
1               5

<210> SEQ ID NO 22
<211> LENGTH: 10
<212> TYPE: PRT
<213> ORGANISM: Mus musculus

<400> SEQUENCE: 22

Gly Phe Thr Phe Ser Asn Phe Gly Met His
1               5                   10

<210> SEQ ID NO 23
<211> LENGTH: 17
```

```
<212> TYPE: PRT
<213> ORGANISM: Mus musculus

<400> SEQUENCE: 23

Tyr Ile Ser Arg Gly Ser Ser Asn Ile Tyr Tyr Ala Asp Thr Val Lys
1               5                   10                  15
Gly

<210> SEQ ID NO 24
<211> LENGTH: 14
<212> TYPE: PRT
<213> ORGANISM: Mus musculus

<400> SEQUENCE: 24

Thr Pro Tyr Asp Tyr Asp Gly Tyr Tyr Tyr Ala Met Asp Tyr
1               5                   10

<210> SEQ ID NO 25
<211> LENGTH: 10
<212> TYPE: PRT
<213> ORGANISM: Mus musculus

<400> SEQUENCE: 25

Gly Tyr Ala Leu Thr Asn Tyr Trp Ile Asp
1               5                   10

<210> SEQ ID NO 26
<211> LENGTH: 17
<212> TYPE: PRT
<213> ORGANISM: Mus musculus

<400> SEQUENCE: 26

Asn Val Tyr Pro Glu Gly Gly Phe Val Asn Tyr Asn Glu Asn Phe Lys
1               5                   10                  15
Gly

<210> SEQ ID NO 27
<211> LENGTH: 7
<212> TYPE: PRT
<213> ORGANISM: Mus musculus

<400> SEQUENCE: 27

Asp Tyr Asp Gly Phe Asp Phe
1               5

<210> SEQ ID NO 28
<211> LENGTH: 10
<212> TYPE: PRT
<213> ORGANISM: Mus musculus

<400> SEQUENCE: 28

Gly Tyr Thr Phe Thr Ser Tyr Ile Met His
1               5                   10

<210> SEQ ID NO 29
<211> LENGTH: 17
<212> TYPE: PRT
<213> ORGANISM: Mus musculus

<400> SEQUENCE: 29

Tyr Ile Asn Pro Tyr Asn Glu Gly Thr Lys Tyr Asn Glu Ala Phe Glu
1               5                   10                  15
Asp
```

<210> SEQ ID NO 30
<211> LENGTH: 11
<212> TYPE: PRT
<213> ORGANISM: Mus musculus

<400> SEQUENCE: 30

Asp Thr Thr Ile Gly Asp Trp Tyr Phe Asp Val
1               5                   10

<210> SEQ ID NO 31
<211> LENGTH: 11
<212> TYPE: PRT
<213> ORGANISM: Mus musculus

<400> SEQUENCE: 31

Gly Tyr Ser Ile Thr Ser Asp Tyr Ala Trp Thr
1               5                   10

<210> SEQ ID NO 32
<211> LENGTH: 16
<212> TYPE: PRT
<213> ORGANISM: Mus musculus

<400> SEQUENCE: 32

Tyr Ile Ser Phe Thr Gly Thr Thr Ser Tyr Thr Pro Ser Leu Lys Ser
1               5                   10                  15

<210> SEQ ID NO 33
<211> LENGTH: 8
<212> TYPE: PRT
<213> ORGANISM: Mus musculus

<400> SEQUENCE: 33

Ser Val Ile Phe Thr Ile Asp Ser
1               5

<210> SEQ ID NO 34
<211> LENGTH: 10
<212> TYPE: PRT
<213> ORGANISM: Mus musculus

<400> SEQUENCE: 34

Gly Tyr Thr Phe Thr Glu Tyr Thr Met His
1               5                   10

<210> SEQ ID NO 35
<211> LENGTH: 17
<212> TYPE: PRT
<213> ORGANISM: Mus musculus

<400> SEQUENCE: 35

Gly Ile Asn Pro Asp Asn Gly Gly Pro Ser Tyr Ser Gln Lys Phe Lys
1               5                   10                  15

Gly

<210> SEQ ID NO 36
<211> LENGTH: 10
<212> TYPE: PRT
<213> ORGANISM: Mus musculus

<400> SEQUENCE: 36

Glu Thr His Asp Tyr Asp Lys Phe Ala Tyr
1               5                   10

<210> SEQ ID NO 37
<211> LENGTH: 30
<212> TYPE: DNA
<213> ORGANISM: Mus musculus

<400> SEQUENCE: 37
agtgccagct caagtgtaat ttacatgtac                                        30

<210> SEQ ID NO 38
<211> LENGTH: 21
<212> TYPE: DNA
<213> ORGANISM: Mus musculus

<400> SEQUENCE: 38
gacacatcca acctggtttc t                                                 21

<210> SEQ ID NO 39
<211> LENGTH: 27
<212> TYPE: DNA
<213> ORGANISM: Mus musculus

<400> SEQUENCE: 39
cagcagtaca gtggttaccc gtacacg                                           27

<210> SEQ ID NO 40
<211> LENGTH: 48
<212> TYPE: DNA
<213> ORGANISM: Mus musculus

<400> SEQUENCE: 40
aaatctagtc agaggattgt acatagtgat gggaagacct atttagaa                    48

<210> SEQ ID NO 41
<211> LENGTH: 21
<212> TYPE: DNA
<213> ORGANISM: Mus musculus

<400> SEQUENCE: 41
aaagtttcca accgattttc t                                                 21

<210> SEQ ID NO 42
<211> LENGTH: 27
<212> TYPE: DNA
<213> ORGANISM: Mus musculus

<400> SEQUENCE: 42
tttcaaggtt cacatattcc gtggacg                                           27

<210> SEQ ID NO 43
<211> LENGTH: 45
<212> TYPE: DNA
<213> ORGANISM: Mus musculus

<400> SEQUENCE: 43
agagccagcg aaagtgttga taattttggc tttagtttta tgaac                       45

<210> SEQ ID NO 44
<211> LENGTH: 21
<212> TYPE: DNA
<213> ORGANISM: Mus musculus

<400> SEQUENCE: 44

```
agtgcatcca accaaggatc c                                              21

<210> SEQ ID NO 45
<211> LENGTH: 27
<212> TYPE: DNA
<213> ORGANISM: Mus musculus

<400> SEQUENCE: 45
cagcaaagta aggagattcc tttcacg                                        27

<210> SEQ ID NO 46
<211> LENGTH: 33
<212> TYPE: DNA
<213> ORGANISM: Mus musculus

<400> SEQUENCE: 46
agggcctccg gcaacatcca caattacctg acc                                 33

<210> SEQ ID NO 47
<211> LENGTH: 18
<212> TYPE: DNA
<213> ORGANISM: Mus musculus

<400> SEQUENCE: 47
aatgccaagg ccctggcc                                                  18

<210> SEQ ID NO 48
<211> LENGTH: 27
<212> TYPE: DNA
<213> ORGANISM: Mus musculus

<400> SEQUENCE: 48
ctgcactttt ggagcagccc cctgacc                                        27

<210> SEQ ID NO 49
<211> LENGTH: 51
<212> TYPE: DNA
<213> ORGANISM: Mus musculus

<400> SEQUENCE: 49
aagtcctccc agtccctgct gtactccaac aatcagaaga attacctggc c             51

<210> SEQ ID NO 50
<211> LENGTH: 21
<212> TYPE: DNA
<213> ORGANISM: Mus musculus

<400> SEQUENCE: 50
tgggcctcca caagggagtc c                                              21

<210> SEQ ID NO 51
<211> LENGTH: 27
<212> TYPE: DNA
<213> ORGANISM: Mus musculus

<400> SEQUENCE: 51
cagcagtact acagctaccc cctgacc                                        27

<210> SEQ ID NO 52
<211> LENGTH: 51
<212> TYPE: DNA
<213> ORGANISM: Homo sapiens

<400> SEQUENCE: 52
```
aagtccagcc agagtgtttt atatagctcc aacaataaga actacttagc t    51

<210> SEQ ID NO 53
<211> LENGTH: 27
<212> TYPE: DNA
<213> ORGANISM: Homo sapiens

<400> SEQUENCE: 53
cagcaatctt atagtactcc gctcact    27

<210> SEQ ID NO 54
<211> LENGTH: 51
<212> TYPE: DNA
<213> ORGANISM: Homo sapiens

<400> SEQUENCE: 54
aagtccagcc agagtgtttt atacacctcc aacaataaca actacttagc t    51

<210> SEQ ID NO 55
<211> LENGTH: 27
<212> TYPE: DNA
<213> ORGANISM: Homo sapiens

<400> SEQUENCE: 55
cagcaatatt ttagtactcc gatcacc    27

<210> SEQ ID NO 56
<211> LENGTH: 51
<212> TYPE: DNA
<213> ORGANISM: Homo sapiens

<400> SEQUENCE: 56
aagtccagcc agagtgtttt atacaacccc aacagtaaga attacttcgc t    51

<210> SEQ ID NO 57
<211> LENGTH: 27
<212> TYPE: DNA
<213> ORGANISM: Homo sapiens

<400> SEQUENCE: 57
caacaatatt atatcactcc gtacact    27

<210> SEQ ID NO 58
<211> LENGTH: 30
<212> TYPE: DNA
<213> ORGANISM: Mus musculus

<400> SEQUENCE: 58
ggattcactt tcagtaactt tggaatgcac    30

<210> SEQ ID NO 59
<211> LENGTH: 51
<212> TYPE: DNA
<213> ORGANISM: Mus musculus

<400> SEQUENCE: 59
tacattagta gaggcagtag caacatctac tatgcagaca cagtgaaggg c    51

<210> SEQ ID NO 60
<211> LENGTH: 42
<212> TYPE: DNA
<213> ORGANISM: Mus musculus

<400> SEQUENCE: 60
accccctatg attacgacgg atattactat gctatggact ac                42

<210> SEQ ID NO 61
<211> LENGTH: 30
<212> TYPE: DNA
<213> ORGANISM: Mus musculus

<400> SEQUENCE: 61
ggatacgccc tcactaacta ctggatagat                              30

<210> SEQ ID NO 62
<211> LENGTH: 51
<212> TYPE: DNA
<213> ORGANISM: Mus musculus

<400> SEQUENCE: 62
aatgtttacc ctgaaggtgg ttttgtcaat tacaatgaga actttaaggg c       51

<210> SEQ ID NO 63
<211> LENGTH: 21
<212> TYPE: DNA
<213> ORGANISM: Mus musculus

<400> SEQUENCE: 63
gattacgacg ggtttgactt c                                       21

<210> SEQ ID NO 64
<211> LENGTH: 30
<212> TYPE: DNA
<213> ORGANISM: Mus musculus

<400> SEQUENCE: 64
ggatacacat tcaccagtta tattatgcac                              30

<210> SEQ ID NO 65
<211> LENGTH: 51
<212> TYPE: DNA
<213> ORGANISM: Mus musculus

<400> SEQUENCE: 65
tatattaatc cttacaatga aggcactaag tataatgagg cgttcgaaga c       51

<210> SEQ ID NO 66
<211> LENGTH: 33
<212> TYPE: DNA
<213> ORGANISM: Mus musculus

<400> SEQUENCE: 66
gatactacga taggtgactg gtacttcgat gtt                          33

<210> SEQ ID NO 67
<211> LENGTH: 33
<212> TYPE: DNA
<213> ORGANISM: Mus musculus

<400> SEQUENCE: 67
ggctactcaa tcaccagtga ttatgcctgg acc                          33

<210> SEQ ID NO 68
<211> LENGTH: 48
<212> TYPE: DNA
<213> ORGANISM: Mus musculus -continued
<210> SEQ ID NO 68
<211> LENGTH: 48
<212> TYPE: DNA
<213> ORGANISM: Mus musculus

<400> SEQUENCE: 68
tacataagtt tcactggtac cactagctac accccatctc tcaaaagt                48

<210> SEQ ID NO 69
<211> LENGTH: 24
<212> TYPE: DNA
<213> ORGANISM: Mus musculus

<400> SEQUENCE: 69
agtgtgattt ttactataga ctcc                                          24

<210> SEQ ID NO 70
<211> LENGTH: 30
<212> TYPE: DNA
<213> ORGANISM: Mus musculus

<400> SEQUENCE: 70
ggatacacat tcactgaata caccatgcac                                    30

<210> SEQ ID NO 71
<211> LENGTH: 51
<212> TYPE: DNA
<213> ORGANISM: Mus musculus

<400> SEQUENCE: 71
ggtattaatc ctgacaatgg tggtcctagc tacagccaga aattcaaggg c             51

<210> SEQ ID NO 72
<211> LENGTH: 30
<212> TYPE: DNA
<213> ORGANISM: Mus musculus

<400> SEQUENCE: 72
gaaacacatg attacgacaa gtttgcttac                                    30

<210> SEQ ID NO 73
<211> LENGTH: 477
<212> TYPE: PRT
<213> ORGANISM: Homo sapiens

<400> SEQUENCE: 73

Met Pro Pro Cys Gln Pro Gln Arg Pro Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
    370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Ser Lys Glu Leu
        435                 440                 445

Gln Phe Gly Arg Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475

<210> SEQ ID NO 74
<211> LENGTH: 491
<212> TYPE: PRT
<213> ORGANISM: Rhesus macaque

<400> SEQUENCE: 74

Met Pro Pro Cys Gln Pro Arg Arg Pro Leu Leu Leu Leu Leu Leu Leu
1               5                   10                  15

Leu Ala Cys Gln Pro Gln Ala Pro Ser Ala Gln Val Met Asp Phe Leu
            20                  25                  30

Phe Glu Lys Trp Lys Leu Tyr Gly Asp Gln Cys His His Asn Leu Ser

```
                35                  40                  45
Leu Leu Pro Pro Pro Thr Glu Leu Val Cys Asn Arg Thr Phe Asp Lys
 50                  55                  60

Tyr Ser Cys Trp Pro Asp Thr Pro Ala Asn Thr Ala Asn Ile Ser
 65                  70                  75                  80

Cys Pro Trp Tyr Leu Pro Trp His His Lys Val Gln His Arg Phe Val
                     85                  90                  95

Phe Lys Arg Cys Gly Pro Asp Gly Gln Trp Val Arg Gly Pro Arg Gly
                100                 105                 110

Gln Pro Trp Arg Asp Ala Ser Gln Cys Gln Met Asp Gly Glu Glu Leu
                115                 120                 125

Glu Val Gln Lys Glu Val Ala Lys Met Tyr Ser Ser Phe Gln Val Met
            130                 135                 140

Tyr Thr Val Gly Tyr Ser Leu Ser Leu Gly Ala Leu Leu Leu Ala Leu
145                 150                 155                 160

Ala Val Leu Gly Gly Ile Ser Lys Leu His Cys Thr Arg Asn Ala Ile
                165                 170                 175

His Ala Asn Leu Phe Val Ser Phe Val Leu Lys Ala Ser Ser Val Leu
                180                 185                 190

Val Ile Asp Gly Leu Leu Arg Thr Arg Tyr Ser Gln Lys Ile Gly Asp
            195                 200                 205

Asp Leu Ser Val Ser Ile Trp Leu Ser Asp Gly Ala Val Ala Gly Cys
210                 215                 220

Arg Val Ala Ala Val Phe Met Gln Tyr Gly Val Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
                260                 265                 270

Gly Ala Pro Met Leu Phe Ile Ile Pro Trp Val Val Arg Cys Leu
                275                 280                 285

Phe Glu Asn Ile Gln Cys Trp Thr Ser Asn Asp Asn Met Gly Phe Trp
290                 295                 300

Trp Ile Leu Arg Phe Pro Val Phe Leu Ala Ile Leu Ile Asn Phe Phe
305                 310                 315                 320

Ile Phe Ile Arg Ile Val His Leu Leu Val Ala Lys Leu Arg Ala Arg
                325                 330                 335

Glu Met His His Thr Asp Tyr Lys Phe Arg Leu Ala Lys Ser Thr Leu
                340                 345                 350

Thr Leu Ile Pro Leu Leu Gly Val His Glu Val Val Phe Ala Phe Val
            355                 360                 365

Thr Asp Glu His Ala Gln Gly Thr Leu Arg Phe Ala Lys Leu Phe Phe
            370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg His Trp His
                405                 410                 415

Arg Trp Arg Leu Gly Lys Val Leu Gln Glu Arg Gly Thr Ser Asn
                420                 425                 430

His Lys Ala Pro Ser Ala Pro Gly Gln Gly Leu Pro Gly Lys Lys Leu
            435                 440                 445

Gln Ser Gly Arg Gly Gly Gly Ser Gln Asp Ser Ser Ala Glu Ile Pro
450                 455                 460
```

Leu Ala Gly Gly Leu Pro Arg Leu Ala Glu Ser Pro Phe Ser Thr Leu
465                 470                 475                 480

Leu Gly Pro Gln Leu Gly Leu Asp Ser Gly Thr
            485                 490

<210> SEQ ID NO 75
<211> LENGTH: 485
<212> TYPE: PRT
<213> ORGANISM: Rattus norvegicus

<400> SEQUENCE: 75

Met Leu Leu Thr Gln Leu His Cys Pro Tyr Leu Leu Leu Leu Leu Val
1               5                   10                  15

Val Leu Ser Cys Leu Pro Lys Ala Pro Ser Ala Gln Val Met Asp Phe
            20                  25                  30

Leu Phe Glu Lys Trp Lys Leu Tyr Ser Asp Gln Cys His His Asn Leu
        35                  40                  45

Ser Leu Leu Pro Pro Thr Glu Leu Val Cys Asn Arg Thr Phe Asp
50                  55                  60

Lys Tyr Ser Cys Trp Pro Asp Thr Pro Pro Asn Thr Thr Ala Asn Ile
65                  70                  75                  80

Ser Cys Pro Trp Tyr Leu Pro Trp Tyr His Lys Val Gln His Arg Leu
                85                  90                  95

Val Phe Lys Arg Cys Gly Pro Asp Gly Gln Trp Val Arg Gly Pro Arg
            100                 105                 110

Gly Gln Ser Trp Arg Asp Ala Ser Gln Cys Gln Met Asp Asp Asp Glu
        115                 120                 125

Ile Glu Val Gln Lys Gly Val Ala Lys Met Tyr Ser Ser Tyr Gln Val
130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
            180                 185                 190

Leu Val Ile Asp Trp Leu Leu Lys Thr Arg Tyr Ser Gln Lys Ile Gly
        195                 200                 205

Asp Asp Leu Ser Val Ser Val Trp Leu Ser Asp Gly Ala Val Ala Gly
210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Ile
                245                 250                 255

Thr Thr Phe Ser Glu Lys Ser Phe Phe Ser Leu Tyr Leu Cys Ile Gly
            260                 265                 270

Trp Gly Ser Pro Leu Leu Phe Val Ile Pro Trp Val Val Val Lys Cys
        275                 280                 285

Leu Phe Glu Asn Val Gln Cys Trp Thr Ser Asn Asp Asn Met Gly Phe
290                 295                 300

Trp Trp Ile Leu Arg Ile Pro Val Leu Leu Ala Ile Leu Ile Asn Phe
305                 310                 315                 320

Phe Ile Phe Val Arg Ile Ile His Leu Leu Val Ala Lys Leu Arg Ala
                325                 330                 335

His Gln Met His Tyr Ala Asp Tyr Lys Phe Arg Leu Ala Arg Ser Thr

```
                    340               345               350
Leu Thr Leu Ile Pro Leu Leu Gly Val His Glu Val Phe Ala Phe
            355               360               365
Val Thr Asp Glu His Ala Gln Gly Thr Leu Arg Ser Thr Lys Leu Phe
    370                   375               380
Phe Asp Leu Phe Phe Ser Ser Phe Gln Gly Leu Leu Val Ala Val Leu
385                 390               395                 400
Tyr Cys Phe Leu Asn Lys Glu Val Gln Ala Glu Leu Leu Arg Arg Trp
                405               410               415
Arg Arg Trp Gln Glu Gly Lys Ala Leu Gln Glu Glu Arg Met Ala Ser
            420               425               430
Ser His Gly Ser His Met Ala Pro Ala Gly Thr Cys His Gly Asp Pro
            435               440               445
Cys Glu Lys Leu Gln Leu Met Ser Ala Gly Ser Ser Gly Thr Gly
            450               455               460
Cys Glu Pro Ser Ala Lys Thr Ser Leu Ala Ser Ser Leu Pro Arg Leu
465                 470               475                 480
Ala Asp Ser Pro Thr
                485

<210> SEQ ID NO 76
<211> LENGTH: 485
<212> TYPE: PRT
<213> ORGANISM: Mus musculus

<400> SEQUENCE: 76

Met Pro Leu Thr Gln Leu His Cys Pro His Leu Leu Leu Leu Leu
1               5                   10                  15
Val Leu Ser Cys Leu Pro Glu Ala Pro Ser Ala Gln Val Met Asp Phe
                20                  25                  30
Leu Phe Glu Lys Trp Lys Leu Tyr Ser Asp Gln Cys His His Asn Leu
            35                  40                  45
Ser Leu Leu Pro Pro Pro Thr Glu Leu Val Cys Asn Arg Thr Phe Asp
    50                  55                  60
Lys Tyr Ser Cys Trp Pro Asp Thr Pro Pro Asn Thr Thr Ala Asn Ile
65              70                  75                  80
Ser Cys Pro Trp Tyr Leu Pro Trp Tyr His Lys Val Gln His Arg Leu
                85                  90                  95
Val Phe Lys Arg Cys Gly Pro Asp Gly Gln Trp Val Arg Gly Pro Arg
                100                 105                 110
Gly Gln Pro Trp Arg Asn Ala Ser Gln Cys Gln Leu Asp Asp Glu Glu
            115                 120                 125
Ile Glu Val Gln Lys Gly Val Ala Lys Met Tyr Ser Ser Gln Gln Val
    130                 135                 140
Met Tyr Thr Val Gly Tyr Ser Leu Ser Leu Gly Ala Leu Leu Leu Ala
145                 150                 155                 160
Leu Val Ile Leu Leu Gly Leu Arg Lys Leu His Cys Thr Arg Asn Tyr
                165                 170                 175
Ile His Gly Asn Leu Phe Ala Ser Phe Val Leu Lys Ala Gly Ser Val
                180                 185                 190
Leu Val Ile Asp Trp Leu Leu Lys Thr Arg Tyr Ser Gln Lys Ile Gly
            195                 200                 205
Asp Asp Leu Ser Val Ser Val Trp Leu Ser Asp Gly Ala Met Ala Gly
    210                 215                 220
```

```
Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Leu
            245                 250                 255

Ala Thr Phe Ser Glu Arg Ser Phe Phe Ser Leu Tyr Leu Gly Ile Gly
        260                 265                 270

Trp Gly Ala Pro Leu Leu Phe Val Ile Pro Trp Val Val Lys Cys
    275                 280                 285

Leu Phe Glu Asn Val Gln Cys Trp Thr Ser Asn Asp Asn Met Gly Phe
    290                 295                 300

Trp Trp Ile Leu Arg Ile Pro Val Phe Leu Ala Leu Leu Ile Asn Phe
305                 310                 315                 320

Phe Ile Phe Val His Ile Ile His Leu Leu Val Ala Lys Leu Arg Ala
                325                 330                 335

His Gln Met His Tyr Ala Asp Tyr Lys Phe Arg Leu Ala Arg Ser Thr
            340                 345                 350

Leu Thr Leu Ile Pro Leu Leu Gly Val His Glu Val Val Phe Ala Phe
        355                 360                 365

Val Thr Asp Glu His Ala Gln Gly Thr Leu Arg Ser Thr Lys Leu Phe
370                 375                 380

Phe Asp Leu Phe Leu Ser Ser Phe Gln Gly Leu Leu Val Ala Val Leu
385                 390                 395                 400

Tyr Cys Phe Leu Asn Lys Glu Val Gln Ala Glu Leu Met Arg Arg Trp
            405                 410                 415

Arg Gln Trp Gln Glu Gly Lys Ala Leu Gln Glu Glu Arg Leu Ala Ser
        420                 425                 430

Ser His Gly Ser His Met Ala Pro Ala Gly Pro Cys His Gly Asp Pro
    435                 440                 445

Cys Glu Lys Leu Gln Leu Met Ser Ala Gly Ser Ser Gly Thr Gly
    450                 455                 460

Cys Val Pro Ser Met Glu Thr Ser Leu Ala Ser Ser Leu Pro Arg Leu
465                 470                 475                 480

Ala Asp Ser Pro Thr
                485

<210> SEQ ID NO 77
<211> LENGTH: 1431
<212> TYPE: DNA
<213> ORGANISM: Homo sapiens

<400> SEQUENCE: 77 atgccccct gccagccaca gcgacccctg ctgctgttgc tgctgctgct ggcctgccag      60
ccacaggtcc cctccgctca ggtgatggac ttcctgtttg agaagtggaa gctctacggt     120
gaccagtgtc accacaacct gagcctgctg ccccctccca cggagctggt gtgcaacaga     180
accttcgaca gtattcctg ctggccgac accccgcca ataccacggc caacatctcc        240
tgcccctggt acctgccttg caccacaaa gtgcaacacc gcttcgtgtt caagagatgc      300
gggcccgacg tcagtgggt gcgtggaccc cgggggcagc cttggcgtga tgcctcccag      360
tgccagatga tggcgagga gattgaggtc cagaaggagg tggccaagat gtacagcagc     420
ttccaggtga tgtacacagt gggctacagc ctgtccctgg ggccctgct cctcgccttg      480 gccatcctgg ggggcctcag caagctgcac tgcaccgca atgccatcca cgcgaatctg      540
tttgcgtcct tcgtgctgaa agccagctcc gtgctggtca ttgatgggct gctcaggacc     600
```

```
cgctacagcc agaaaattgg cgacgacctc agtgtcagca cctggctcag tgatggagcg      660
gtggctggct gccgtgtggc cgcggtgttc atgcaatatg gcatcgtggc caactactgc      720
tggctgctgg tggagggcct gtacctgcac aacctgctgg gcctggccac cctccccgag      780
aggagcttct tcagcctcta cctgggcatc ggctggggtg ccccatgct gttcgtcgtc       840
ccctgggcag tggtcaagtg tctgttcgag aacgtccagt gctggaccag caatgacaac      900
atgggcttct ggtggatcct gcggttcccc gtcttcctgg ccatcctgat caacttcttc      960
atcttcgtcc gcatcgttca gctgctcgtg gccaagctgc gggcacggca gatgcaccac     1020
acagactaca agttccggct ggccaagtcc acgctgaccc tcatccctct gctgggcgtc     1080
cacgaagtgg tcttcgcctt cgtgacggac gagcacgccc agggcaccct cgctccgcc     1140
aagctcttct tcgacctctt cctcagctcc ttccagggcc tgctggtggc tgtcctctac    1200
tgcttcctca caaggaggt gcagtcggag ctgcggcggc gttggcaccg ctggcgcctg     1260
ggcaaagtgc tatgggagga gcggaacacc agcaaccaca gggcctcatc ttcgcccggc    1320
cacggccctc ccagcaagga gctgcagttt gggaggggtg gtggcagcca ggattcatct    1380
gcggagaccc ccttggctgg tggcctccct agattggctg agagccccct c             1431

<210> SEQ ID NO 78
<211> LENGTH: 1473
<212> TYPE: DNA
<213> ORGANISM: Rhesus macaque

<400> SEQUENCE: 78 atgccccct gtcagccacg tcgacccctg ctactgttgc tgctgctgct ggcctgccag        60
ccacaggccc cctccgctca ggtgatggac ttcctgtttg agaagtggaa actctacggt       120
gaccagtgtc accacaacct gagcctgctg ccccctccca cggagctggt ctgtaacaga       180
accttcgaca gtattcctg ctggccagac accccgcca ataccacggc caacatctcc         240
tgccctggt acctgccttg gcaccacaaa gtgcaacacc gcttcgtgtt caagagatgc        300
gggcccgatg gtcagtgggt gcgtggaccc cgggggcagc cttggcgtga cgcctctcag       360
tgccagatgg acggcgagga gcttgaggtc cagaaggagg tggctaagat gtacagcagc       420
ttccaggtga tgtacacggt gggctacagc ctgtccctgg ggccctgct cctcgccttg        480
gccgtcctgg ggggcatcag caagctgcac tgcacccgca acgccatcca cgcgaacctg       540
tttgtgtcct tcgtgctgaa ggccagctcc gtgctggtca tcgatgggct gctcaggacc       600
cgctacagcc agaagattgg cgacgacctc agtgtcagca tctggctcag tgatggagcg      660
gtggccggct gccgtgtggc cgcggtgttc atgcaatatg gcgtcgtggc caactactgc      720
tggctgctgg tggagggcct gtacctgcac aacctgctgg gcctggccac cctccctgag      780
aggagcttct tcagcctcta cctgggcatc ggctggggtg ccccatgct gttcatcatc       840
ccctgggtgg tggtcaggtg tctgttcgag aacatccagt gctggaccag caatgacaac      900
atgggcttct ggtggatcct gcggttcccc gtcttcctgg ccatcctgat caacttcttc      960
atcttcatcc gcattgttca cctgcttgtg gccaagctgc gggcgcggga gatgcaccac     1020
acagactaca agttccgact ggccaagtcc acactgaccc tcatccccct gctgggtgtc     1080
cacgaagtgg tcttcgcctt cgtgacggac gagcacgccc agggcaccct cgcttcgcc      1140
aagctcttct tcgacctctt cctcagctcc ttccagggcc tgctggtggc tgtcctctac    1200
tgcttcctca caaggaggt gcagtcggaa cttggcggc attggcaccg ctggcgcctg      1260
ggcaaagtgc tgcaggagga gcggggcacc agcaaccaca aggcccatc tgcgcctggc     1320
```

| | |
|---|---|
| caaggccttc ctggcaagaa gctgcagtct gggagggatg gtggcagcca ggactcatct | 1380 |
| gcggagatcc ccttggctgg tggcctccct aggttggctg agagcccctt ctcaactctg | 1440 |
| ctgggacccc agctagggct ggactcaggc acc | 1473 |

<210> SEQ ID NO 79
<211> LENGTH: 1455
<212> TYPE: DNA
<213> ORGANISM: Rattus norvegicus

<400> SEQUENCE: 79

| | |
|---|---|
| atgctcctca cccagctcca ctgtccctac ctgctgctgc tgctggtggt gctgtcatgt | 60 |
| ctgccaaagg caccctctgc ccaggtaatg gactttttgt ttgagaagtg gaagctctat | 120 |
| agtgaccagt gccaccacaa cctaagcctg ctgcccccac ctactgagct ggtctgcaac | 180 |
| agaactttcg acaagtactc ctgctggcct gacacccctc ccaacaccac tgccaacatt | 240 |
| tcctgcccct ggtacctacc ttggtaccac aaagtgcagc accgcctagt gttcaagagg | 300 |
| tgtgggcctg atgggcagtg ggttcgaggg ccacggggc agtcatggcg cgacgcctcc | 360 |
| caatgtcaga tggatgatga cgagatcgag gtccagaagg gggtagccaa gatgtatagc | 420 |
| agctaccagg tgatgtacac tgtgggctac agtctgtccc tgggggcctt gctcctggcg | 480 |
| ctggtcatcc tgctgggcct caggaagctg cactgcaccc ggaactacat ccacgggaac | 540 |
| ctgttcgcgt ccttcgtgct caaggctggc tctgtgctgg tcattgattg gctgctcaag | 600 |
| acacgctata gccagaagat ggagatgac ctcagtgtga cgtctggct cagtgatggg | 660 |
| gcggtggctg gctgcagagt ggccacagtg atcatgcagt acggcatcat agccaactac | 720 |
| tgctggttgc tggtggaggg tgtgtacctg tacagcctgc tgagcatcac caccttctcg | 780 |
| gagaagagct tcttctccct ctatctgtgc atcggctggg gatctcccct gctgtttgtc | 840 |
| atcccctggg tggtggtcaa gtgtctgttt gagaatgtcc agtgctggac cagcaatgac | 900 |
| aatatgggat tctggtggat cctgcgtatc cctgtactcc tggccatact gatcaatttt | 960 |
| ttcatctttg tccgcatcat tcatcttctt gtggccaagc tgcgtgccca tcagatgcac | 1020 |
| tatgctgatt acaagttccg gctagccagg tccacgctga ccctcattcc tctgctggga | 1080 |
| gtccacgaag tggtctttgc ctttgtgact gatgagcatg cccagggcac cctgcgctcc | 1140 |
| accaagctct tttttgacct gttcttcagc tccttccagg gtctgctggt ggctgttctc | 1200 |
| tactgtttcc tcaacaagga ggtgcaggca gagctactgc ggcgttggag gcgatggcaa | 1260 |
| gaaggcaaag ctcttcagga ggaaaggatg ccagcagcc atggcagcca catggcccca | 1320 |
| gcagggactt gtcatggtga tccctgtgag aaacttcagc ttatgagtgc aggcagcagc | 1380 |
| agtgggactg gctgtgagcc ctctgcgaag acctcattgg ccagtagtct cccaaggctg | 1440 |
| gctgacagcc ccacc | 1455 |

<210> SEQ ID NO 80
<211> LENGTH: 1455
<212> TYPE: DNA
<213> ORGANISM: Mus musculus

<400> SEQUENCE: 80

| | |
|---|---|
| atgcccctca cccagctcca ctgtccccac ctgctgctgc tgctgttggt gctgtcatgt | 60 |
| ctgccagagg caccctctgc ccaggtaatg gactttttgt ttgagaagtg gaagctctat | 120 |
| agtgaccaat gccaccacaa cctaagcctg ctgcccccac ctactgagct ggtctgtaac | 180 |

```
agaaccttcg acaagtactc ctgctggcct gacacccctc ccaacaccac tgccaacatt      240
tcctgcccct ggtacctacc ttggtaccac aaagtgcagc accgcctagt gttcaagagg      300
tgtgggcccg atgggcagtg ggttcgaggg ccacggggc agccgtggcg caacgcctcc       360
caatgtcagt tggatgatga agagatcgag gtccagaagg gggtggccaa gatgtatagc      420
agccagcagg tgatgtacac cgtgggctac agtctgtccc tgggggcctt gctccttgcg      480
ctggtcatcc tgctgggcct caggaagctg cactgcaccc gaaactacat ccatgggaac      540
ctgtttgcgt cctttgtgct caaggctggc tctgtgttgg tcatcgattg gctgctgaag      600
acacggtaca gccagaagat tggcgatgac ctcagtgtga cgtctggct cagtgacggg       660 gcgatggccg gctgcagagt ggccacagtg atcatgcagt acggcatcat agccaactat      720
tgctggttgc tggtagaggg cgtgtacctg tacagcctgc tgagccttgc caccttctct      780
gagaggagct tcttttccct ctacctgggc attggctggg gtgcgcccct gctgtttgtc      840
atcccctggg tggtggtcaa gtgtctgttt gagaatgttc agtgctggac cagcaatgac      900
aacatgggat tctggtggat cctgcgtatt cctgtcttcc tggccttact gatcaatttt      960
ttcatctttg tccacatcat tcaccttctt gtggccaagc tgcgtgccca tcagatgcac     1020
tatgctgact ataagttccg gctggccagg tccacgctga ccctcatccc tctgctgggg     1080
gtccacgagg tggtctttgc ctttgtgact gacgagcatg cccaaggcac cctgcgctcc     1140
accaagctct tttttgacct gttcctcagc tccttccagg gtctgctggt ggctgttctc     1200
tactgtttcc tcaacaagga ggtgcaggca gagctgatgc ggcgttggag caatggcaa      1260 gaaggcaaag ctcttcagga ggaaaggttg gccagcagcc atggcagcca catggccccca    1320 gcagggcctt gtcatggtga tccctgtgag aaacttcagc ttatgagtgc aggcagcagc    1380
agtgggactg gctgtgtgcc ctctatggag acctcgctgg ccagtagtct cccaaggttg    1440
gctgacagcc ccacc                                                      1455

<210> SEQ ID NO 81
<211> LENGTH: 107
<212> TYPE: PRT
<213> ORGANISM: Mus musculus

<400> SEQUENCE: 81

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ile Tyr Met
                20                  25                  30

Tyr Trp Tyr Gln Gln Lys Pro Gly Ser Ser Pro Arg Leu Trp Ile Tyr
            35                  40                  45

Asp Thr Ser Asn Leu Val Ser Gly Val Pro Ala Arg Phe Ser Gly Ser
        50                  55                  60

Arg Ser Gly Thr Ser Tyr Ser Leu Thr Ile Ser Ser Met Glu Ala Gly
65                  70                  75                  80

Asp Ala Ala Thr Tyr Tyr Cys Gln Gln Tyr Ser Gly Tyr Pro Tyr Thr
                85                  90                  95

Phe Gly Gly Gly Thr Lys Leu Glu Ile Lys Arg
            100                 105

<210> SEQ ID NO 82
<211> LENGTH: 113
<212> TYPE: PRT
<213> ORGANISM: Mus musculus
```

```
<400> SEQUENCE: 82

Asp Ile Leu Leu Thr Gln Thr Pro Leu Ser Leu Pro Val Ser Leu Gly
1               5                   10                  15

Asp Gln Ala Ser Ile Ser Cys Lys Ser Ser Gln Arg Ile Val His Ser
            20                  25                  30

Asp Gly Lys Thr Tyr Leu Glu Trp Tyr Leu Gln Lys Pro Gly Gln Ser
        35                  40                  45

Pro Lys Pro Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Asn Leu Glu Ile Lys
            100                 105                 110

Arg

<210> SEQ ID NO 83
<211> LENGTH: 112
<212> TYPE: PRT
<213> ORGANISM: Mus musculus

<400> SEQUENCE: 83

Asp Ile Val Leu Thr Gln Ser Pro Ala Ser Leu Ala Val Ser Pro Gly
1               5                   10                  15

Gln Arg Ala Thr Ile Ser Cys Arg Ala Ser Glu Ser Val Asp Asn Phe
            20                  25                  30

Gly Phe Ser Phe Met Asn Trp Phe Gln Gln Lys Pro Gly Gln Pro Pro
        35                  40                  45

Lys Leu Leu Ile Tyr Ser Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ser Ala Met Tyr Phe Cys Gln Gln Ser Lys
                85                  90                  95

Glu Ile Pro Phe Thr Phe Gly Ser Gly Thr Lys Leu Glu Ile Lys Arg
            100                 105                 110

<210> SEQ ID NO 84
<211> LENGTH: 108
<212> TYPE: PRT
<213> ORGANISM: Mus musculus

<400> SEQUENCE: 84

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Thr Trp Phe Gln Gln Arg Arg Gly Lys Ser Pro Gln Leu Leu Val
        35                  40                  45

Tyr Asn Ala Lys Ala Leu Ala Asp Gly Val Pro Ser Arg Phe Ser Gly
    50                  55                  60

Ser Gly Ser Gly Thr Glu Tyr Ser Leu Lys Ile Asn Ser Leu Gln Pro
65                  70                  75                  80

Glu Asp Phe Gly Asp Tyr Tyr Cys Leu His Phe Trp Ser Ser Pro Leu
                85                  90                  95
```

```
Thr Phe Gly Ala Gly Thr Lys Leu Glu Leu Lys Arg
            100             105

<210> SEQ ID NO 85
<211> LENGTH: 114
<212> TYPE: PRT
<213> ORGANISM: Mus musculus

<400> SEQUENCE: 85

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly His
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr His Cys Gln Gln
                85                  90                  95

Tyr Tyr Ser Tyr Pro Leu Thr Phe Gly Ala Gly Thr Lys Leu Glu Leu
            100                 105                 110

Lys Arg

<210> SEQ ID NO 86
<211> LENGTH: 108
<212> TYPE: PRT
<213> ORGANISM: Artificial Sequence
<220> FEATURE:
<223> OTHER INFORMATION: Synthetic construct

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Phe Gln Gln Lys Pro Gly Lys Ala Pro Lys Leu Leu Val
        35                  40                  45

Tyr Asn Ala Lys Ala Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu His Phe Trp Ser Ser Pro Leu
                85                  90                  95

Thr Phe Gly Gly Gly Thr Lys Val Glu Ile Lys Arg
            100                 105

<210> SEQ ID NO 87
<211> LENGTH: 114
<212> TYPE: PRT
<213> ORGANISM: Artificial Sequence
<220> FEATURE:
<223> OTHER INFORMATION: Synthetic construct

<400> SEQUENCE: 87

Asp Ile Val Met Ser Gln Ser Pro Asp Ser Leu Ala Val Ser Leu Gly
1               5                   10                  15
```

Glu Arg Ala Thr Ile Asn Cys Lys Ser Ser Gln Ser Leu Tyr Ser
            20                  25                  30

Asn Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Gln
                85                  90                  95

Tyr Tyr Ser Tyr Pro Leu Thr Phe Gly Gly Gly Thr Lys Val Glu Ile
            100                 105                 110

Lys Arg

<210> SEQ ID NO 88
<211> LENGTH: 114
<212> TYPE: PRT
<213> ORGANISM: Homo sapiens

<400> SEQUENCE: 88

Asp Ile Arg Leu Thr Gln Ser Pro Asp Ser Leu Pro Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Thr Pro Leu Thr Phe Gly Gly Gly Thr Lys Val Asp Ile
            100                 105                 110

Lys Arg

<210> SEQ ID NO 89
<211> LENGTH: 114
<212> TYPE: PRT
<213> ORGANISM: Homo sapiens

<400> SEQUENCE: 89

Asp Ile Gln Leu Thr Gln Ser Pro Asp Ser Leu Ala Val Ser Leu Gly
1               5                   10                  15

Glu Arg Ala Ala Ile Asn Cys Lys Ser Ser Gln Ser Val Leu Tyr Thr
            20                  25                  30

Ser Asn Asn Asn Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Thr Pro Ile Thr Phe Gly Gln Gly Thr Lys Leu Glu Ile
            100                 105                 110

Lys Arg

<210> SEQ ID NO 90
<211> LENGTH: 114
<212> TYPE: PRT
<213> ORGANISM: Homo sapiens

<400> SEQUENCE: 90

Asp Ile Gln Val Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Pro Asn Ser Lys Asn Tyr Phe Ala Trp Tyr Gln Gln Lys Pro Gly His
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Ser Thr Leu Thr
65                  70                  75                  80

Ile Ser Ser Leu Gln Ala Glu Asp Val Ala Val Tyr Tyr Cys Gln Gln
                85                  90                  95

Tyr Tyr Ile Thr Pro Tyr Thr Phe Gly Gln Gly Thr Lys Val Glu Ile
            100                 105                 110

Lys Arg

<210> SEQ ID NO 91
<211> LENGTH: 123
<212> TYPE: PRT
<213> ORGANISM: Mus musculus

<400> SEQUENCE: 91

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Val Pro Glu Lys Gly Leu Glu Trp Val
        35                  40                  45

Ala Tyr Ile Ser Arg Gly Ser Ser Asn Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Thr Pro Tyr Asp Tyr Asp Gly Tyr Tyr Tyr Ala Met Asp Tyr
            100                 105                 110

Trp Gly Gln Gly Thr Ser Val Thr Val Ser Ser
        115                 120

<210> SEQ ID NO 92
<211> LENGTH: 116
<212> TYPE: PRT
<213> ORGANISM: Mus musculus

<400> SEQUENCE: 92

Gln Val Gln Leu Gln Gln Ser Gly Ala Glu Leu Val Arg Pro Gly Thr
1               5                   10                  15

Ser Val Lys Met Ser Cys Lys Ala Thr Gly Tyr Ala Leu Thr Asn Tyr
            20                  25                  30

```
Trp Ile Asp Trp Val Arg Gln Arg Pro Gly His Gly Leu Glu Trp Ile
         35                  40                  45

Gly Asn Val Tyr Pro Glu Gly Gly Phe Val Asn Tyr Asn Glu Asn Phe
     50                  55                  60

Lys Gly Lys Ala Lys Leu Thr Ala Asp Thr Ser Ser Lys Thr Ala Tyr
 65              70                  75                  80

Ile Gln Leu Asn Ser Leu Thr Ser Glu Asp Ser Ala Ile Tyr Tyr Cys
                 85                  90                  95

Ala Tyr Asp Tyr Asp Gly Phe Asp Phe Trp Gly Gln Gly Thr Thr Leu
             100                 105                 110

Thr Val Ser Ser
        115
```

<210> SEQ ID NO 93
<211> LENGTH: 120
<212> TYPE: PRT
<213> ORGANISM: Mus musculus

<400> SEQUENCE: 93

```
Gly Val His Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
             20                  25                  30

Ile Met His Trp Val Lys Gln Arg Pro Gly Gln Gly Leu Glu Trp Ile
         35                  40                  45

Gly Tyr Ile Asn Pro Tyr Asn Glu Gly Thr Lys Tyr Asn Glu Ala Phe
     50                  55                  60

Glu Asp Lys Ala Thr Leu Thr Ser Asp Lys Ser Ser Asn Thr Ala Tyr
 65              70                  75                  80

Met Glu Leu Ser Ser Leu Thr Phe Glu Asp Ser Ala Val Tyr Tyr Cys
                 85                  90                  95

Ala Arg Asp Thr Thr Ile Gly Asp Trp Tyr Phe Asp Val Trp Gly Ala
             100                 105                 110

Gly Thr Thr Val Thr Val Ser Ser
        115                 120
```

<210> SEQ ID NO 94
<211> LENGTH: 117
<212> TYPE: PRT
<213> ORGANISM: Mus musculus

<400> SEQUENCE: 94

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
             20                  25                  30

Tyr Ala Trp Thr Trp Ile Arg Gln Phe Pro Gly Asn Lys Leu Glu Trp
         35                  40                  45

Met Gly Tyr Ile Ser Phe Thr Gly Thr Thr Tyr Thr Pro Ser Leu
     50                  55                  60

Lys Ser Arg Ile Ser Ile Thr Arg Asp Thr Ser Lys Asn Gln Phe Phe
 65              70                  75                  80

Leu Tyr Leu Asn Ser Val Thr Ala Glu Asp Thr Ala Thr Tyr Tyr Cys
                 85                  90                  95

Val Arg Ser Val Ile Phe Thr Ile Asp Ser Trp Gly Gln Gly Thr Ser
             100                 105                 110
```

Val Thr Val Ser Ser
        115

<210> SEQ ID NO 95
<211> LENGTH: 119
<212> TYPE: PRT
<213> ORGANISM: Mus musculus

<400> SEQUENCE: 95

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Glu Lys Ser Leu Glu Trp Ile
        35                  40                  45

Gly Gly Ile Asn Pro Asp Asn Gly Gly Pro Ser Tyr Ser Gln Lys Phe
    50                  55                  60

Lys Gly Lys Ala Thr Leu Thr Val Asp Lys Ser Ser Asn Thr Ala Tyr
65                  70                  75                  80

Ile Glu Ile Arg Ser Leu Thr Ser Glu Asp Ser Ala Val Tyr Phe Cys
                85                  90                  95

Ala Glu Glu Thr His Asp Tyr Asp Lys Phe Ala Tyr Trp Gly Gln Gly
            100                 105                 110

Thr Leu Val Thr Val Ser Ala
        115

<210> SEQ ID NO 96
<211> LENGTH: 117
<212> TYPE: PRT
<213> ORGANISM: Artificial Sequence
<220> FEATURE:
<223> OTHER INFORMATION: Synthetic construct

<400> SEQUENCE: 96

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Thr Trp Ile Arg Gln Pro Pro Gly Lys Gly Leu Glu Trp
        35                  40                  45

Met Gly Tyr Ile Ser Phe Thr Gly Thr Thr Tyr Thr Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Lys Ser Val Ile Phe Thr Ile Asp Ser Trp Gly Gln Gly Thr Leu
            100                 105                 110

Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: Synthetic construct

<400> SEQUENCE: 97

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Arg Leu Glu Trp Ile
        35                  40                  45

Gly Gly Ile Asn Pro Asp Asn Gly Gly Pro Ser Tyr Ser Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Glu Glu Thr His Asp Tyr Asp Lys Phe Ala Tyr Trp Gly Gln Gly
            100                 105                 110

Thr Leu Val Thr Val Ser Ser
        115
```

<210> SEQ ID NO 98
<211> LENGTH: 321
<212> TYPE: DNA
<213> ORGANISM: Mus musculus

<400> SEQUENCE: 98

```
caaattgttc tcacccagtc tccagcaatc atgtctgcat ctccagggga aaaggtcacc      60
atgacctgca gtgccagctc aagtgtaatt tacatgtact ggtaccagca gaagccaggc     120
tcctccccca gactctggat ttatgacaca tccaacctgg tttctggagt ccctgctcgc     180
ttcagtggca gtaggtctgg gacctcttat tctctcacaa tcagcagcat ggaggctgga     240
gatgctgcca cttattactg ccagcagtac agtggttacc cgtacacgtt cggagggggg     300
accaagctgg aaataaaacg g                                                321
```

<210> SEQ ID NO 99
<211> LENGTH: 340
<212> TYPE: DNA
<213> ORGANISM: Mus musculus

<400> SEQUENCE: 99

```
gatattttgc tgacccaaac tccactctcc ctgcctgtca gtcttggaga tcaagcctcc      60
atctcttgca atctagtca gaggattgta catagtgatg gaagaccta tttagaatgg      120
tacttgcaga aaccaggcca gtctccaaag cccctgatct acaaagtttc caaccgattt     180
tctggggtcc cagacaggtt cagcggcagt gggtcaggga caaatttcac actcaagatc     240
agcagagtgg aggctgagga tctgggagtt tattattgtt ttcaaggttc acatattccg     300
tggacgttcg gtggaggcac caacctggaa atcaaacggg                            340
```

<210> SEQ ID NO 100
<211> LENGTH: 336
<212> TYPE: DNA
<213> ORGANISM: Mus musculus

<400> SEQUENCE: 100

```
gacattgtac tgacccaatc tccagcttct ttggctgtgt ctccagggca gagggccacc      60
atctcgtgca gagccagcga aagtgttgat aattttggct ttagttttat gaactggttc     120
caacagaaac caggacagcc acccaaactc ctcatctata gtgcatccaa ccaaggatcc     180
```

```
ggggtccctg ccaggtttag tggcagtggg tctgggacag acttcagcct caacatccat    240
cctatggagg aggatgattc tgcaatgtat ttctgtcagc aaagtaagga gattcctttc    300
acgttcggct cggggacaaa gttggaaata aacgg                               336
```

<210> SEQ ID NO 101
<211> LENGTH: 324
<212> TYPE: DNA
<213> ORGANISM: Mus musculus

<400> SEQUENCE: 101

```
gacatccaga tgactcagtc tccagcctcc ctatctgcat ctgtgggaga aactgtcacc     60
atcacatgta gggcctccgg caacatccac aattacctga cctggtttca gcagaggcgg    120
ggaaaatctc ctcagctcct ggtctataat gccaaggccc tggccgatgg tgtgccatca    180
agattcagtg gcagtggatc aggaacagaa tattctctca aaatcaacag cctgcagcct    240
gaagattttg ggattatta ctgtctgcac ttttggagca gccccctgac cttcggtgct    300
gggaccaagc tggagctgaa acgg                                           324
```

<210> SEQ ID NO 102
<211> LENGTH: 342
<212> TYPE: DNA
<213> ORGANISM: Mus musculus

<400> SEQUENCE: 102

```
gacattgtga tgtcacagtc tccatcctcc ctagctgtgt cagttggaga aaggttact     60 atgagctgca gtcctccca gtccctgctg tactccaaca atcagaagaa ttacctggcc    120
tggtaccagc agaaaccagg gcattctcct aaactgctga tctactgggc ctccacaagg    180
gagtccgggg tccctgatcg cttcacaggc agtggatctg gacagattt cactctcacc    240 atcagcagtg tgaaggctga agacctggca gtttatcact gtcagcagta ctacagctac    300
cccctgacct tcggtgctgg gaccaagctg gagctgaaac gg                       342
```

<210> SEQ ID NO 103
<211> LENGTH: 324
<212> TYPE: DNA
<213> ORGANISM: Artificial Sequence
<220> FEATURE:
<223> OTHER INFORMATION: Synthetic construct

<400> SEQUENCE: 103

```
gacatccaga tgacccagtc cccctcctcc ctgagcgcct ctgtgggaga cagggtgacc     60
atcacatgca gggcctccgg caacatccac aattacctga cctggtttca gcagaagcct    120
ggcaaggccc ctaagctgct ggtgtacaat gccaaggccc tggccgatgg cgtgcccagc    180
agattttccg gcagcggctc cggcacagac tacaccctga caatctccag cctgcagccc    240
gaggacttcg ccacctacta ctgtctgcac ttttggagca gccccctgac ctttggcggc    300
ggaacaaagg tggagatcaa gcgt                                           324
```

<210> SEQ ID NO 104
<211> LENGTH: 342
<212> TYPE: DNA
<213> ORGANISM: Artificial Sequence
<220> FEATURE:
<223> OTHER INFORMATION: Synthetic construct

<400> SEQUENCE: 104

```
gatatcgtga tgagccagag ccccgatagc ctggccgtga gcctgggaga gagggctaca     60
```

```
atcaattgta agtcctccca gtccctgctg tactccaaca atcagaagaa ttacctggcc    120
tggtaccagc agaagcccgg ccagccaccc aagctgctga tctactgggc ctccacaagg    180
gagtccggcg tgccagacag gttctccggc agcggatccg gcaccgactt taccctgacc    240
atctcctccc tgcaggccga ggatgtggcc gtgtaccact gccagcagta ctacagctac    300
cccctgacct tcggcggcgg cacaaaggtg gagatcaagc gt                       342
```

<210> SEQ ID NO 105
<211> LENGTH: 342
<212> TYPE: DNA
<213> ORGANISM: Homo sapiens

<400> SEQUENCE: 105

```
gacatccggt tgacccagtc tccagactcc ctgcctgtgt ctctgggcga gagggccacc    60
atcaactgca gtccagccag agtgttttta tatagctcca acaataagaa ctacttagct    120
tggtaccagc agaaaccagg acagcctcct aagctgctca tttactgggc ctccacaagg    180
gagtccgggg tccctgaccg attcagtggc agcgggtctg ggacagattt cactctcacc    240
atcagcagcc tgcaggctga agatgtggca gtttattact gtcagcaatc ttatagtact    300
ccgctcactt tcggcggagg gaccaaagtg gatatcaaac gt                       342
```

<210> SEQ ID NO 106
<211> LENGTH: 342
<212> TYPE: DNA
<213> ORGANISM: Homo sapiens

<400> SEQUENCE: 106

```
gacatccagt tgacccagtc tccagactcc ctggctgtgt ctctgggcga gagggccgcc    60
atcaactgca gtccagccag agtgttttta tacacctcca acaataacaa ctacttagct    120
tggtaccagc agaaaccagg acagcctcct aagctgctca tttactgggc ctccacaagg    180
gagtccgggg tccctgaccg attcagtggc agcgggtctg ggacagattt cactctcacc    240
atcagcagcc tgcaggctga agatgtggca gtttattact gtcagcaata ttttagtact    300
ccgatcacct tcggccaagg gaccaagctg gagatcaaac gt                       342
```

<210> SEQ ID NO 107
<211> LENGTH: 342
<212> TYPE: DNA
<213> ORGANISM: Homo sapiens

<400> SEQUENCE: 107

```
gacatccagg tgacccagtc tccagactcc ctggctgtgt ccctgggcga gagggccacc    60
atcaactgca gtccagccag agtgttttta tacaacccca acagtaagaa ttacttcgct    120
tggtaccagc agaaaccagg acaccctcct aagttactca tttactgggc ctccacaagg    180
gagtccgggg tccctgaccg attcagtggc agcgggtctg ggacagattc cactctcacc    240
atcagcagcc tgcaggctga agatgtggca gtttattact gtcaacaata ttatatcact    300
ccgtacactt ttggccaggg gaccaaggtg gaaatcaaac gt                       342
```

<210> SEQ ID NO 108
<211> LENGTH: 369
<212> TYPE: DNA
<213> ORGANISM: Mus musculus

<400> SEQUENCE: 108

```
gatgtgcagc tggtggagtc tgggggaggc ttagtgcagc tggagggtc ccggaaactc      60 tcctgtgcag cctctggatt cactttcagt aactttggaa tgcactgggt tcgtcaggtt    120
ccagagaagg ggctggagtg ggtcgcatac attagtagag gcagtagcaa catctactat    180
gcagacacag tgaagggccg attcaccatc tccagagaca atcccaagaa caccctgttc    240
ctgcaaatga ccagtctaag gtctgaggac acggccatgt attactgtgc aagaaccccc    300
tatgattacg acggatatta ctatgctatg gactactggg gtcaaggaac ctcagtcacc    360
gtctcctca                                                            369
```

```
<210> SEQ ID NO 109
<211> LENGTH: 348
<212> TYPE: DNA
<213> ORGANISM: Mus musculus

<400> SEQUENCE: 109
```

```
caggtccagc tgcagcagtc tggagctgaa ctggtaaggc ctgggacttc agtgaagatg     60
tcctgcaagg ctactggata cgccctcact aactactgga tagattgggt taggcagagg   120
cctggacatg gccttgagtg gattggaaat gtttaccctg aaggtggttt tgtcaattac   180
aatgagaact ttaagggcaa ggccaaactg actgcagaca tcctccaa aacagcctat     240 atacaactca acagcctgac atctgaggac tctgccatct attactgtgc ctatgattac   300
gacgggtttg acttctgggg ccaaggcacc actctcacag tctcttca                348
```

```
<210> SEQ ID NO 110
<211> LENGTH: 360
<212> TYPE: DNA
<213> ORGANISM: Mus musculus

<400> SEQUENCE: 110
```

```
ggggtccacc tgcagcagtc tggacctgag ctggtaaagc ctggggcttc agttaagatg     60
tcctgcaagg cctctggata cacattcacc agttatatta tgcactgggt taagcagagg   120
cctgggcagg gccttgagtg gattggatat attaatcctt acaatgaagg cactaagtat   180
aatgaggcgt tcgaagacaa ggccacactg acctcagaca atcctccaa tacagcctac     240 atggaactca gcagcctgac cttgaggac tcggcggttt attactgtgc aagagatact    300
acgataggtg actggtactt cgatgtttgg ggcgcaggga ccacggtcac cgtctcctca   360
```

```
<210> SEQ ID NO 111
<211> LENGTH: 351
<212> TYPE: DNA
<213> ORGANISM: Mus musculus

<400> SEQUENCE: 111
```

```
gatgtgcagc ttcaggagtc gggacctggc ctggtgaaac cttctcagtc tctgtccctc     60
acctgcactg tcactggcta ctcaatcacc agtgattatg cctggacctg gatccggcag   120
tttccaggaa acaaactgga gtggatgggc tacataagtt tcactggtac cactagctac   180 acccccatctc tcaaaagtcg aatctctatc actcgagaca catccaagaa ccagttcttc   240
ctgtatttga attctgtgac tgctgaggac acagccacat attactgtgt aagaagtgtg   300 attttttacta tagactcctg gggtcaagga acctcagtca ccgtctcctc a           351
```

```
<210> SEQ ID NO 112
<211> LENGTH: 357
<212> TYPE: DNA
<213> ORGANISM: Mus musculus
```

<400> SEQUENCE: 112

```
gaggtccagc tgcaacagtc tggacctgaa ctggtgaagc tggggcttc agtgaagatt      60
tcctgcaaga cttctggata cacattcact gaatacacca tgcactgggt gaagcagagc     120
catgaaaaga gccttgagtg gattggaggt attaatcctg acaatggtgg tcctagctac     180
agccagaaat tcaagggcaa ggccacattg actgtagaca gtcctccaa cacagcctac      240
atagagatcc gcagcctgac atctgaggat tctgcagtct atttctgtgc agaggaaaca     300
catgattacg acaagtttgc ttactggggc caagggactc tggtcactgt ctctgca       357
```

<210> SEQ ID NO 113
<211> LENGTH: 351
<212> TYPE: DNA
<213> ORGANISM: Artificial Sequence
<220> FEATURE:
<223> OTHER INFORMATION: Synthetic construct

<400> SEQUENCE: 113

```
caggtgcagc tgcaggagtc cggacctggc ctggtgaagc cttcccagac cctgagcctg      60
acctgtacag tgagcggcta ctcaatcacc agtgattatg cctggacctg gatcagacag     120
ccccccggaa agggcctgga gtggatggga tacataagtt tcactggtac cactagctac     180
accccatctc tcaaaagtag aatcacaatc agcagagaca catccaagaa ccagttcagc     240
ctgaagctgt ccagcgtgac agccgccgat acagccgtgt actactgtgt gaagagtgtg     300
atttttacta tagactcctg gggccagggc accctggtga ccgtttcctc c              351
```

<210> SEQ ID NO 114
<211> LENGTH: 357
<212> TYPE: DNA
<213> ORGANISM: Artificial Sequence
<220> FEATURE:
<223> OTHER INFORMATION: Synthetic construct

<400> SEQUENCE: 114

```
caggtgcagc tggtgcagtc cggagctgag gtgaagaagc ccggcgccag cgtgaaggtg      60
tcctgtaagg cgagcggata cacattcact gaatacacca tgcactgggt gaggcaggcc     120
cctggccaga actggagtg gatcggcggt attaatcctg acaatggtgg tcctagctac      180
agccagaaat tcaagggcag ggtgaccatc accaggata cctccgccag caccgcctac      240
atggagctgt cctccctgcg gtccgaggat acagccgtgt actactgtgc gaggaaaca      300
catgattacg acaagtttgc ttactggggc cagggcaccc tggtgacagt gtccagc       357
```

<210> SEQ ID NO 115
<211> LENGTH: 106
<212> TYPE: PRT
<213> ORGANISM: Homo sapiens

<400> SEQUENCE: 115

Ala Asp Ala Ala Pro Thr Val Ser Ile Phe Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

```
Tyr Ser Met Ser Ser Thr Leu Thr Leu Thr Lys Asp Glu Tyr Glu Arg
 65                  70                  75                  80

His Asn Ser Tyr Thr Cys Glu Ala Thr His Lys Thr Ser Thr Ser Pro
                 85                  90                  95

Ile Val Lys Ser Phe Asn Arg Asn Glu Cys
            100                 105
```

<210> SEQ ID NO 116
<211> LENGTH: 105
<212> TYPE: PRT
<213> ORGANISM: Homo sapiens

<400> SEQUENCE: 116

```
Gly Gln Pro Lys Ser Thr Pro Thr Leu Thr Val Phe Pro Pro Ser Ser
 1               5                  10                  15

Glu Glu Leu Lys Glu Asn Lys Ala Thr Leu Val Cys Leu Ile Ser Asn
                20                  25                  30

Phe Ser Pro Ser Gly Val Thr Val Ala Trp Lys Ala Asn Gly Thr Pro
             35                  40                  45

Ile Thr Gln Gly Val Asp Thr Ser Asn Pro Thr Lys Glu Gly Asn Lys
         50                  55                  60

Phe Met Ala Ser Ser Phe Leu His Leu Thr Ser Asp Gln Trp Arg Ser
 65                  70                  75                  80

His Asn Ser Phe Thr Cys Gln Val Thr His Glu Gly Asp Thr Val Glu
                 85                  90                  95

Lys Ser Leu Ser Pro Ala Glu Cys Leu
            100                 105
```

<210> SEQ ID NO 117
<211> LENGTH: 326
<212> TYPE: PRT
<213> ORGANISM: Homo sapiens
<220> FEATURE:
<221> NAME/KEY: MISC_FEATURE
<222> LOCATION: (131)..(131)
<223> OTHER INFORMATION: Xaa at position 131 is Met or Tyr
<220> FEATURE:
<221> NAME/KEY: MISC_FEATURE
<222> LOCATION: (133)..(133)
<223> OTHER INFORMATION: Xaa at position 133 is Ser or Thr
<220> FEATURE:
<221> NAME/KEY: MISC_FEATURE
<222> LOCATION: (135)..(135)
<223> OTHER INFORMATION: Xaa at position 135 is Thr or Glu
<220> FEATURE:
<221> NAME/KEY: MISC_FEATURE
<222> LOCATION: (307)..(307)
<223> OTHER INFORMATION: Xaa at position 307 is Met or Leu
<220> FEATURE:
<221> NAME/KEY: MISC_FEATURE
<222> LOCATION: (313)..(313)
<223> OTHER INFORMATION: Xaa at position 313 is Asn or Ser
<220> FEATURE:
<221> NAME/KEY: MISC_FEATURE
<222> LOCATION: (326)..(326)
<223> OTHER INFORMATION: Xaa at position 326 is Lys or is absent

<400> SEQUENCE: 117

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45
```

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Xaa Ile Xaa Arg Xaa Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Xaa His Glu Ala Leu His Xaa His Tyr Thr Gln Lys Ser Leu
305                 310                 315                 320

Ser Leu Ser Pro Gly Xaa
                325

<210> SEQ ID NO 118
<211> LENGTH: 327
<212> TYPE: PRT
<213> ORGANISM: Homo sapiens
<220> FEATURE:
<221> NAME/KEY: MISC_FEATURE
<222> LOCATION: (132)..(132)
<223> OTHER INFORMATION: Xaa at position 132 is Met or Tyr
<220> FEATURE:
<221> NAME/KEY: MISC_FEATURE
<222> LOCATION: (134)..(134)
<223> OTHER INFORMATION: Xaa at position 134 is Ser or Thr
<220> FEATURE:
<221> NAME/KEY: MISC_FEATURE
<222> LOCATION: (136)..(136)
<223> OTHER INFORMATION: Xaa at position 136 is Thr or Glu
<220> FEATURE:
<221> NAME/KEY: MISC_FEATURE
<222> LOCATION: (308)..(308)
<223> OTHER INFORMATION: Xaa at position 308 is Met or Leu
<220> FEATURE:
<221> NAME/KEY: MISC_FEATURE
<222> LOCATION: (314)..(314)
<223> OTHER INFORMATION: Xaa at position 314 is Asn or Ser
<220> FEATURE:
<221> NAME/KEY: MISC_FEATURE
<222> LOCATION: (327)..(327)
<223> OTHER INFORMATION: Xaa at position 327 is Lys or is absent

<400> SEQUENCE: 118

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Xaa Ile Xaa Arg Xaa Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Xaa His Glu Ala Leu His Xaa His Tyr Thr Gln Lys Ser
305                 310                 315                 320

Leu Ser Leu Ser Leu Gly Xaa
                325
```

<210> SEQ ID NO 119
<211> LENGTH: 29
<212> TYPE: PRT
<213> ORGANISM: Homo sapiens

<400> SEQUENCE: 119

His Ala Glu Gly Thr Phe Thr Ser Asp Val Ser Ser Tyr Leu Glu Gly

Gln Ala Ala Lys Glu Phe Ile Ala Trp Leu Val Lys Gly
            20                  25

<210> SEQ ID NO 120
<211> LENGTH: 29
<212> TYPE: PRT
<213> ORGANISM: Artificial Sequence
<220> FEATURE:
<223> OTHER INFORMATION: Synthetic construct

<400> SEQUENCE: 120

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 121
<211> LENGTH: 22
<212> TYPE: PRT
<213> ORGANISM: Artificial Sequence
<220> FEATURE:
<223> OTHER INFORMATION: Synthetic construct

<400> SEQUENCE: 121

His Gly Glu Gly Thr Phe Thr Ser Asp Val Ser Ser Tyr Leu Glu Gly
1               5                   10                  15

Gln Ala Ala Lys Glu Phe
            20

<210> SEQ ID NO 122
<211> LENGTH: 23
<212> TYPE: PRT
<213> ORGANISM: Artificial Sequence
<220> FEATURE:
<223> OTHER INFORMATION: Synthetic construct

<400> SEQUENCE: 122

His Gly Glu Gly Thr Phe Thr Ser Asp Val Ser Ser Tyr Leu Glu Gly
1               5                   10                  15

Gln Ala Ala Lys Glu Phe Ile
            20

<210> SEQ ID NO 123
<211> LENGTH: 24
<212> TYPE: PRT
<213> ORGANISM: Artificial Sequence
<220> FEATURE:
<223> OTHER INFORMATION: Synthetic construct

<400> SEQUENCE: 123

His Gly Glu Gly Thr Phe Thr Ser Asp Val Ser Ser Tyr Leu Glu Gly
1               5                   10                  15

Gln Ala Ala Lys Glu Phe Ile Ala
            20

<210> SEQ ID NO 124
<211> LENGTH: 5
<212> TYPE: PRT
<213> ORGANISM: Artificial Sequence
<220> FEATURE:
<223> OTHER INFORMATION: Synthetic construct

<400> SEQUENCE: 124

```
Gly Gly Gly Gly Ser
1               5

<210> SEQ ID NO 125
<211> LENGTH: 10
<212> TYPE: PRT
<213> ORGANISM: Artificial Sequence
<220> FEATURE:
<223> OTHER INFORMATION: Synthetic construct

<400> SEQUENCE: 125

Gly Gly Gly Gly Ser Gly Gly Gly Gly Ser
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Synthetic construct

<400> SEQUENCE: 126

Gly Gly Gly Gly Ser Gly Gly Gly Gly Ser Gly Gly Gly Gly Ser
1               5                   10                  15

<210> SEQ ID NO 127
<211> LENGTH: 29
<212> TYPE: PRT
<213> ORGANISM: Artificial Sequence
<220> FEATURE:
<223> OTHER INFORMATION: Synthetic construct

<400> SEQUENCE: 127

Gly Lys Val Leu Trp Ala Ile Phe Glu Lys Ala Ala Gln Gly Glu Leu
1               5                   10                  15

Tyr Ser Ser Val Asp Ser Thr Phe Thr Gly Glu Ala His
            20                  25

<210> SEQ ID NO 128
<211> LENGTH: 29
<212> TYPE: PRT
<213> ORGANISM: Artificial Sequence
<220> FEATURE:
<223> OTHER INFORMATION: Synthetic construct

<400> SEQUENCE: 128

Gly Lys Val Leu Trp Ala Ile Phe Glu Lys Ala Ala Gln Gly Glu Leu
1               5                   10                  15

Tyr Ser Ser Val Asp Ser Thr Phe Thr Gly Glu Gly His
            20                  25

<210> SEQ ID NO 129
<211> LENGTH: 22
<212> TYPE: PRT
<213> ORGANISM: Artificial Sequence
<220> FEATURE:
<223> OTHER INFORMATION: Synthetic construct

<400> SEQUENCE: 129

Phe Glu Lys Ala Ala Gln Gly Glu Leu Tyr Ser Ser Val Asp Ser Thr
1               5                   10                  15

Phe Thr Gly Glu Gly His
            20

<210> SEQ ID NO 130
```

<211> LENGTH: 23
<212> TYPE: PRT
<213> ORGANISM: Artificial Sequence
<220> FEATURE:
<223> OTHER INFORMATION: Synthetic construct

<400> SEQUENCE: 130

Ile Phe Glu Lys Ala Ala Gln Gly Glu Leu Tyr Ser Ser Val Asp Ser
1               5                   10                  15

Thr Phe Thr Gly Glu Gly His
            20

<210> SEQ ID NO 131
<211> LENGTH: 24
<212> TYPE: PRT
<213> ORGANISM: Artificial Sequence
<220> FEATURE:
<223> OTHER INFORMATION: Synthetic construct

<400> SEQUENCE: 131

Ala Ile Phe Glu Lys Ala Ala Gln Gly Glu Leu Tyr Ser Ser Val Asp
1               5                   10                  15

Ser Thr Phe Thr Gly Glu Gly His
            20

<210> SEQ ID NO 132
<211> LENGTH: 106
<212> TYPE: PRT
<213> ORGANISM: Homo sapiens

<400> SEQUENCE: 132

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His His Gly Leu Ser Ser Pro
                85                  90                  95

Val Thr Lys Ser Phe Asn Arg Gly Glu Cys
            100                 105

<210> SEQ ID NO 133
<211> LENGTH: 106
<212> TYPE: PRT
<213> ORGANISM: Homo sapiens

<400> SEQUENCE: 133

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 134
<211> LENGTH: 11
<212> TYPE: PRT
<213> ORGANISM: Mus musculus

<400> SEQUENCE: 134

Arg Ala Ser Gln Asn Ile Asn Asn Leu Leu Ala
1               5                   10

<210> SEQ ID NO 135
<211> LENGTH: 7
<212> TYPE: PRT
<213> ORGANISM: Mus musculus

<400> SEQUENCE: 135

Thr Ala Ser Ser Leu Gln Ser
1               5

<210> SEQ ID NO 136
<211> LENGTH: 9
<212> TYPE: PRT
<213> ORGANISM: Mus musculus

<400> SEQUENCE: 136

Gln Gln Ala His Arg Phe Pro Pro Thr
1               5

<210> SEQ ID NO 137
<211> LENGTH: 10
<212> TYPE: PRT
<213> ORGANISM: Mus musculus

<400> SEQUENCE: 137

Gly Phe Thr Leu Ser Ser Tyr Gly Met His
1               5                   10

<210> SEQ ID NO 138
<211> LENGTH: 17
<212> TYPE: PRT
<213> ORGANISM: Mus musculus

<400> SEQUENCE: 138

Val Ile Trp Tyr Asp Gly Ser Asn Lys Tyr Tyr Ala Asp Ser Val Lys
1               5                   10                  15

Gly

<210> SEQ ID NO 139
<211> LENGTH: 16
<212> TYPE: PRT
<213> ORGANISM: Mus musculus

<400> SEQUENCE: 139

Gly Gly Gly Ser Gly Ser Tyr Arg Tyr Tyr Tyr Gly Leu Asp Val
1               5                   10                  15

<210> SEQ ID NO 140

```
<211> LENGTH: 108
<212> TYPE: PRT
<213> ORGANISM: Homo sapiens

<400> SEQUENCE: 140

Ala Ile Gln Met Thr Gln Ser Pro Ser Ser Val Ser Ala Ser Ile Gly
1               5                   10                  15

Asp Arg Val Thr Ile Thr Cys Arg Ala Ser Gln Asn Ile Asn Asn Leu
            20                  25                  30

Leu Ala Trp Tyr Gln Gln Lys Pro Gly Lys Ala Pro Lys Leu Leu Ile
        35                  40                  45

Tyr Thr Ala Ser Ser Leu Gln Ser Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Cys Cys Gln Gln Ala His Arg Phe Pro Pro
                85                  90                  95

Thr Phe Gly Gln Gly Thr Lys Val Glu Ile Arg Arg
            100                 105

<210> SEQ ID NO 141
<211> LENGTH: 125
<212> TYPE: PRT
<213> ORGANISM: Homo sapiens

<400> SEQUENCE: 141

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Gly Ser Tyr Arg Tyr Tyr Tyr Gly Leu
            100                 105                 110

Asp Val Trp Gly Gln Gly Thr Thr Val Thr Val Ser Ser
            115                 120                 125
```